US012758237B2

(12) United States Patent
Chappuis et al.

(10) Patent No.: US 12,758,237 B2

(45) Date of Patent: Oct. 13, 2026

(54) SYSTEMS AND METHODS FOR FIXATING A NAVIGATION ARRAY

(71) Applicant: GLOBUS MEDICAL, INC., Audubon, PA (US)

(72) Inventors: Olivier Chappuis, Lutry (CH); Szymon Kostrzewski, Lausanne (CH); Peter Eckert, Renens (CH)

(73) Assignee: Globus Medical, Inc., Audubon, PA (US)

( * ) Notice: Subject to any disclaimer, the term of this patent is extended or adjusted under 35 U.S.C. 154(b) by 1142 days.

(21) Appl. No.: 17/060,331

(22) Filed: Oct. 1, 2020

(65) Prior Publication Data

US 2021/0093333 A1 Apr. 1, 2021

Related U.S. Application Data

(63) Continuation-in-part of application No. 16/841,927, filed on Apr. 7, 2020, now Pat. No. 11,426,178, which is a continuation-in-part of application No. 16/737,054, filed on Jan. 8, 2020, which is a continuation-in-part of application No. 16/587,203, filed on Sep. 30, 2019.

(60) Provisional application No. 62/906,831, filed on Sep. 27, 2019.

(51) Int. Cl.

| | |
|---|---|
| ***A61B 17/17*** | (2006.01) |
| ***A61B 34/20*** | (2016.01) |
| ***A61B 90/00*** | (2016.01) |

(52) U.S. Cl.

CPC ...... *A61B 17/1764* (2013.01); *A61B 17/1703* (2013.01); *A61B 34/20* (2016.02); *A61B 90/39* (2016.02); *A61B 2034/2055* (2016.02); *A61B 2090/3937* (2016.02); *A61B 2090/3979* (2016.02)

(58) Field of Classification Search

CPC ........................ A61B 17/1764; A61B 17/1703

See application file for complete search history.

(56) References Cited

U.S. PATENT DOCUMENTS

| | | | |
|---|---|---|---|
| 1,068,626 | A | 7/1913 | Buck |
| 4,150,293 | A | 4/1979 | Franke |
| 4,737,038 | A | 4/1988 | Dostoomian |
| 4,757,710 | A | 7/1988 | Haynes |
| 5,246,010 | A | 9/1993 | Gazzara et al. |
| 5,259,395 | A | 11/1993 | Li |

(Continued)

FOREIGN PATENT DOCUMENTS

| | | | |
|---|---|---|---|
| CN | 1974094 | A | 6/2007 |
| CN | 101160104 | A | 4/2008 |
| CN | 104363826 | A | 2/2015 |

(Continued)

OTHER PUBLICATIONS

US 8,231,638 B2, 07/2012, Swarup et al. (withdrawn)

*Primary Examiner* — Sameh R Boles

(57) ABSTRACT

Systems and methods for resecting a knee joint using a navigated pin guide driver system. The navigated pin guide driver system communicates with a navigation system to aid a user in placing cut block pins into the knee joint. The navigated pin guide driver system may include a handle, a reference element that electronically communicates with the navigation system, one or more pin guide tubes that may correspond to one or more cut blocks, and a distal tip that is configured to attach to the bone.

7 Claims, 49 Drawing Sheets

(56) References Cited

U.S. PATENT DOCUMENTS 5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,203,543 B1 3/2001 Glossop
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,632,170 B1 10/2003 Bohanan et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,685,706 B2 2/2004 Padget et al.
6,701,173 B2 3/2004 Nowinski et al.
6,719,757 B2 4/2004 Neubauer et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,856,828 B2 2/2005 Cossette et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,993,374 B2 1/2006 Sasso
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.

(56) References Cited

U.S. PATENT DOCUMENTS

| | | | |
|---|---|---|---|
| 7,711,083 | B2 | 5/2010 | Heigl et al. |
| 7,711,406 | B2 | 5/2010 | Kuhn et al. |
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,753,910 | B2 | 7/2010 | Ritland |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,885,705 | B2 | 2/2011 | Murphy |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Willliams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de la Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,180,429 | B2 | 5/2012 | Sasso |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jensen |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,263,933 | B2 | 9/2012 | Zeile |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |
| 8,483,434 | B2 | 7/2013 | Buehner et al. |
| 8,483,800 | B2 | 7/2013 | Jensen et al. |
| 8,486,532 | B2 | 7/2013 | Enzerink et al. |
| 8,489,235 | B2 | 7/2013 | Moll et al. |

(56) References Cited

U.S. PATENT DOCUMENTS

| | | | |
|---|---|---|---|
| 8,500,722 B2 | 8/2013 | Cooper | |
| 8,500,728 B2 | 8/2013 | Newton et al. | |
| 8,504,201 B2 | 8/2013 | Moll et al. | |
| 8,506,555 B2 | 8/2013 | Ruiz Morales | |
| 8,506,556 B2 | 8/2013 | Schena | |
| 8,508,173 B2 | 8/2013 | Goldberg et al. | |
| 8,512,318 B2 | 8/2013 | Tovey et al. | |
| 8,515,576 B2 | 8/2013 | Lipow et al. | |
| 8,518,120 B2 | 8/2013 | Glerum et al. | |
| 8,521,331 B2 | 8/2013 | Itkowitz | |
| 8,526,688 B2 | 9/2013 | Groszmann et al. | |
| 8,526,700 B2 | 9/2013 | Isaacs | |
| 8,527,094 B2 | 9/2013 | Kumar et al. | |
| 8,528,440 B2 | 9/2013 | Morley et al. | |
| 8,532,741 B2 | 9/2013 | Heruth et al. | |
| 8,535,329 B2 | 9/2013 | Sarin et al. | |
| 8,541,970 B2 | 9/2013 | Nowlin et al. | |
| 8,548,563 B2 | 10/2013 | Simon et al. | |
| 8,549,732 B2 | 10/2013 | Burg et al. | |
| 8,551,114 B2 | 10/2013 | Ramos de la Pena | |
| 8,551,116 B2 | 10/2013 | Julian et al. | |
| 8,556,807 B2 | 10/2013 | Scott et al. | |
| 8,556,979 B2 | 10/2013 | Glerum et al. | |
| 8,560,118 B2 | 10/2013 | Green et al. | |
| 8,561,473 B2 | 10/2013 | Blumenkranz | |
| 8,562,594 B2 | 10/2013 | Cooper et al. | |
| 8,571,638 B2 | 10/2013 | Shoham | |
| 8,571,710 B2 | 10/2013 | Coste-Maniere et al. | |
| 8,573,465 B2 | 11/2013 | Shelton, IV | |
| 8,574,303 B2 | 11/2013 | Sharkey et al. | |
| 8,585,420 B2 | 11/2013 | Burbank et al. | |
| 8,594,841 B2 | 11/2013 | Zhao et al. | |
| 8,597,198 B2 | 12/2013 | Sanborn et al. | |
| 8,600,478 B2 | 12/2013 | Verard et al. | |
| 8,603,077 B2 | 12/2013 | Cooper et al. | |
| 8,611,985 B2 | 12/2013 | Lavallee et al. | |
| 8,613,230 B2 | 12/2013 | Blumenkranz et al. | |
| 8,621,939 B2 | 1/2014 | Blumenkranz et al. | |
| 8,624,537 B2 | 1/2014 | Nowlin et al. | |
| 8,630,389 B2 | 1/2014 | Kato | |
| 8,634,897 B2 | 1/2014 | Simon et al. | |
| 8,634,957 B2 | 1/2014 | Toth et al. | |
| 8,638,056 B2 | 1/2014 | Goldberg et al. | |
| 8,638,057 B2 | 1/2014 | Goldberg et al. | |
| 8,639,000 B2 | 1/2014 | Zhao et al. | |
| 8,641,726 B2 | 2/2014 | Bonutti | |
| 8,644,907 B2 | 2/2014 | Hartmann et al. | |
| 8,657,809 B2 | 2/2014 | Schoepp | |
| 8,660,635 B2 | 2/2014 | Simon et al. | |
| 8,666,544 B2 | 3/2014 | Moll et al. | |
| 8,675,939 B2 | 3/2014 | Moctezuma de la Barrera | |
| 8,678,647 B2 | 3/2014 | Gregerson et al. | |
| 8,679,125 B2 | 3/2014 | Smith et al. | |
| 8,679,183 B2 | 3/2014 | Glerum et al. | |
| 8,682,413 B2 | 3/2014 | Lloyd | |
| 8,684,253 B2 | 4/2014 | Giordano et al. | |
| 8,685,098 B2 | 4/2014 | Glerum et al. | |
| 8,693,730 B2 | 4/2014 | Umasuthan et al. | |
| 8,694,075 B2 | 4/2014 | Groszmann et al. | |
| 8,696,458 B2 | 4/2014 | Foxlin et al. | |
| 8,700,123 B2 | 4/2014 | Okamura et al. | |
| 8,706,086 B2 | 4/2014 | Glerum | |
| 8,706,185 B2 | 4/2014 | Foley et al. | |
| 8,706,301 B2 | 4/2014 | Zhao et al. | |
| 8,717,430 B2 | 5/2014 | Simon et al. | |
| 8,727,618 B2 | 5/2014 | Maschke et al. | |
| 8,734,432 B2 * | 5/2014 | Tuma | A61B 34/20 606/1 |
| 8,738,115 B2 | 5/2014 | Amberg et al. | |
| 8,738,181 B2 | 5/2014 | Greer et al. | |
| 8,740,882 B2 | 6/2014 | Jun et al. | |
| 8,746,252 B2 | 6/2014 | McGrogan et al. | |
| 8,749,189 B2 | 6/2014 | Nowlin et al. | |
| 8,749,190 B2 | 6/2014 | Nowlin et al. | |
| 8,761,930 B2 | 6/2014 | Nixon | |
| 8,764,448 B2 | 7/2014 | Yang et al. | |
| 8,771,170 B2 | 7/2014 | Mesallum et al. | |
| 8,781,186 B2 | 7/2014 | Clements et al. | |
| 8,781,630 B2 | 7/2014 | Banks et al. | |
| 8,784,385 B2 | 7/2014 | Boyden et al. | |
| 8,786,241 B2 | 7/2014 | Nowlin et al. | |
| 8,787,520 B2 | 7/2014 | Baba | |
| 8,792,704 B2 | 7/2014 | Isaacs | |
| 8,798,231 B2 | 8/2014 | Notohara et al. | |
| 8,800,838 B2 | 8/2014 | Shelton, IV | |
| 8,808,164 B2 | 8/2014 | Hoffman et al. | |
| 8,812,077 B2 | 8/2014 | Dempsey | |
| 8,814,793 B2 | 8/2014 | Brabrand | |
| 8,816,628 B2 | 8/2014 | Nowlin et al. | |
| 8,818,105 B2 | 8/2014 | Myronenko et al. | |
| 8,820,605 B2 | 9/2014 | Shelton, IV | |
| 8,821,511 B2 | 9/2014 | Von Jako et al. | |
| 8,823,308 B2 | 9/2014 | Nowlin et al. | |
| 8,827,996 B2 | 9/2014 | Scott et al. | |
| 8,828,024 B2 | 9/2014 | Farritor et al. | |
| 8,830,224 B2 | 9/2014 | Zhao et al. | |
| 8,834,489 B2 | 9/2014 | Cooper et al. | |
| 8,834,490 B2 | 9/2014 | Bonutti | |
| 8,838,270 B2 | 9/2014 | Druke et al. | |
| 8,844,789 B2 | 9/2014 | Shelton, IV et al. | |
| 8,855,822 B2 | 10/2014 | Bartol et al. | |
| 8,858,598 B2 | 10/2014 | Seifert et al. | |
| 8,860,753 B2 | 10/2014 | Bhandarkar et al. | |
| 8,864,751 B2 | 10/2014 | Prisco et al. | |
| 8,864,798 B2 | 10/2014 | Weiman et al. | |
| 8,864,833 B2 | 10/2014 | Glerum et al. | |
| 8,867,703 B2 | 10/2014 | Shapiro et al. | |
| 8,870,880 B2 | 10/2014 | Himmelberger et al. | |
| 8,876,866 B2 | 11/2014 | Zappacosta et al. | |
| 8,880,223 B2 | 11/2014 | Raj et al. | |
| 8,882,803 B2 | 11/2014 | Iott et al. | |
| 8,883,210 B1 | 11/2014 | Truncale et al. | |
| 8,888,821 B2 | 11/2014 | Rezach et al. | |
| 8,888,853 B2 | 11/2014 | Glerum et al. | |
| 8,888,854 B2 | 11/2014 | Glerum et al. | |
| 8,894,652 B2 | 11/2014 | Seifert et al. | |
| 8,894,688 B2 | 11/2014 | Suh | |
| 8,894,691 B2 | 11/2014 | Iott et al. | |
| 8,906,069 B2 | 12/2014 | Hansell et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,005,113 B2 | 4/2015 | Scott et al. | |
| 9,044,190 B2 | 6/2015 | Rubner et al. | |
| 9,066,751 B2 | 6/2015 | Sasso | |
| 9,095,376 B2 | 8/2015 | Plabky et al. | |
| 9,107,683 B2 | 8/2015 | Hourtash et al. | |
| 9,125,556 B2 | 9/2015 | Zehavi et al. | |
| 9,131,986 B2 | 9/2015 | Greer et al. | |
| 9,215,968 B2 | 12/2015 | Schostek et al. | |
| 9,271,633 B2 | 3/2016 | Scott et al. | |
| 9,271,847 B2 | 3/2016 | Murphy | |
| 9,308,050 B2 | 4/2016 | Kostrzewski et al. | |
| 9,339,277 B2 | 5/2016 | Jansen et al. | |
| 9,380,984 B2 | 7/2016 | Ll et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,565,997 B2 | 2/2017 | Scott et al. | |
| 9,566,120 B2 | 2/2017 | Malackowski et al. | |
| 9,592,096 B2 | 3/2017 | Maillet et al. | |
| 9,603,621 B2 | 3/2017 | Zhou | |
| 9,713,506 B2 | 7/2017 | Fanson et al. | |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 12/2017 | Donner et al. | |

(56) References Cited

U.S. PATENT DOCUMENTS 9,848,922 B2 12/2017 Tohmeh et al.
9,925,011 B2 3/2018 Gombert et al.
9,931,025 B1 4/2018 Graetzel et al.
9,962,069 B2 5/2018 Scott et al.
9,993,273 B2 6/2018 Moctezuma de la Barrera et al.
10,034,717 B2 7/2018 Miller et al.
10,219,865 B2 3/2019 Jansen et al.
2001/0036302 A1 11/2001 Miller
2002/0035321 A1 3/2002 Bucholz et al.
2002/0107518 A1 8/2002 Neubauer et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0069324 A1* 3/2006 Block .................. A61B 17/864 600/595
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Loyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0165706 A1 6/2012 Lavallee
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0172682 A1 7/2013 Ransden et al.
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0218163 A1 8/2013 Frey
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0267836 A1* 10/2013 Mauldin ............ A61B 17/1671 606/96
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.

(56) References Cited

U.S. PATENT DOCUMENTS

| | | | |
|---|---|---|---|
| 2013/0317521 | A1 | 11/2013 | Choi et al. |
| 2013/0325033 | A1 | 12/2013 | Schena et al. |
| 2013/0325035 | A1 | 12/2013 | Hauck et al. |
| 2013/0331686 | A1 | 12/2013 | Freysinger et al. |
| 2013/0331858 | A1 | 12/2013 | Devengenzo et al. |
| 2013/0331861 | A1 | 12/2013 | Yoon |
| 2013/0342578 | A1 | 12/2013 | Isaacs |
| 2013/0345717 | A1 | 12/2013 | Markvicka et al. |
| 2013/0345757 | A1 | 12/2013 | Stad |
| 2014/0001235 | A1 | 1/2014 | Shelton, IV |
| 2014/0012131 | A1 | 1/2014 | Heruth et al. |
| 2014/0031664 | A1 | 1/2014 | Kang et al. |
| 2014/0046128 | A1 | 2/2014 | Lee et al. |
| 2014/0046132 | A1 | 2/2014 | Hoeg et al. |
| 2014/0046340 | A1 | 2/2014 | Wilson et al. |
| 2014/0049629 | A1 | 2/2014 | Siewerdsen et al. |
| 2014/0052149 | A1 | 2/2014 | van der Walt et al. |
| 2014/0058406 | A1 | 2/2014 | Tsekos |
| 2014/0073914 | A1 | 3/2014 | Lavallee et al. |
| 2014/0080086 | A1 | 3/2014 | Chen |
| 2014/0081128 | A1 | 3/2014 | Verard et al. |
| 2014/0088612 | A1 | 3/2014 | Bartol et al. |
| 2014/0094694 | A1 | 4/2014 | Moctezuma de la Barrera |
| 2014/0094851 | A1 | 4/2014 | Gordon |
| 2014/0096369 | A1 | 4/2014 | Matsumoto et al. |
| 2014/0100587 | A1 | 4/2014 | Farritor et al. |
| 2014/0121676 | A1 | 5/2014 | Kostrzewski et al. |
| 2014/0128882 | A1 | 5/2014 | Kwak et al. |
| 2014/0130810 | A1 | 5/2014 | Azizian et al. |
| 2014/0135796 | A1 | 5/2014 | Simon et al. |
| 2014/0142591 | A1 | 5/2014 | Alvarez et al. |
| 2014/0142592 | A1 | 5/2014 | Moon et al. |
| 2014/0148692 | A1 | 5/2014 | Hartmann et al. |
| 2014/0163581 | A1 | 6/2014 | Devengenzo et al. |
| 2014/0171781 | A1 | 6/2014 | Stiles |
| 2014/0171900 | A1 | 6/2014 | Stiles |
| 2014/0171965 | A1 | 6/2014 | Loh et al. |
| 2014/0180308 | A1 | 6/2014 | von Grunberg |
| 2014/0180309 | A1 | 6/2014 | Seeber et al. |
| 2014/0187915 | A1 | 7/2014 | Yaroshenko et al. |
| 2014/0188132 | A1 | 7/2014 | Kang |
| 2014/0194699 | A1 | 7/2014 | Roh et al. |
| 2014/0221819 | A1 | 8/2014 | Sarment |
| 2014/0222023 | A1 | 8/2014 | Kim et al. |
| 2014/0228631 | A1 | 8/2014 | Kwak et al. |
| 2014/0234804 | A1 | 8/2014 | Huang et al. |
| 2014/0257328 | A1 | 9/2014 | Kim et al. |
| 2014/0257329 | A1 | 9/2014 | Jang et al. |
| 2014/0257330 | A1 | 9/2014 | Choi et al. |
| 2014/0275760 | A1 | 9/2014 | Lee et al. |
| 2014/0275985 | A1 | 9/2014 | Walker et al. |
| 2014/0276931 | A1 | 9/2014 | Parihar et al. |
| 2014/0276940 | A1 | 9/2014 | Seo |
| 2014/0276944 | A1 | 9/2014 | Farritor et al. |
| 2014/0288413 | A1 | 9/2014 | Hwang et al. |
| 2014/0299648 | A1 | 10/2014 | Shelton, IV et al. |
| 2014/0303434 | A1 | 10/2014 | Farritor et al. |
| 2014/0303643 | A1 | 10/2014 | Ha et al. |
| 2014/0305995 | A1 | 10/2014 | Shelton, IV et al. |
| 2014/0309659 | A1 | 10/2014 | Roh et al. |
| 2014/0316436 | A1 | 10/2014 | Bar et al. |
| 2014/0323803 | A1 | 10/2014 | Hoffman et al. |
| 2014/0324070 | A1 | 10/2014 | Min et al. |
| 2014/0330288 | A1 | 11/2014 | Date et al. |
| 2014/0364720 | A1 | 12/2014 | Darrow et al. |
| 2014/0371577 | A1 | 12/2014 | Maillet et al. |
| 2015/0039034 | A1 | 2/2015 | Frankel et al. |
| 2015/0085970 | A1 | 3/2015 | Bouhnik et al. |
| 2015/0146847 | A1 | 5/2015 | Liu |
| 2015/0150524 | A1 | 6/2015 | Yorkston et al. |
| 2015/0196261 | A1 | 7/2015 | Funk |
| 2015/0213633 | A1 | 7/2015 | Chang et al. |
| 2015/0335480 | A1 | 11/2015 | Alvarez et al. |
| 2015/0342647 | A1 | 12/2015 | Frankel et al. |
| 2015/0366556 | A1 | 12/2015 | Khairkhahan et al. |
| 2016/0005194 | A1 | 1/2016 | Schretter et al. |
| 2016/0166329 | A1 | 6/2016 | Langan et al. |
| 2016/0192949 | A1 | 7/2016 | Robichaud et al. |
| 2016/0235480 | A1 | 8/2016 | Scholl et al. |
| 2016/0249990 | A1 | 9/2016 | Glozman et al. |
| 2016/0302871 | A1 | 10/2016 | Gregerson et al. |
| 2016/0320322 | A1 | 11/2016 | Suzuki |
| 2016/0331335 | A1 | 11/2016 | Gregerson et al. |
| 2017/0128142 | A1 | 5/2017 | Still et al. |
| 2017/0135770 | A1 | 5/2017 | Scholl et al. |
| 2017/0143284 | A1 | 5/2017 | Sehnert et al. |
| 2017/0143426 | A1 | 5/2017 | Isaacs et al. |
| 2017/0156816 | A1 | 6/2017 | Ibrahim |
| 2017/0202629 | A1 | 7/2017 | Maillet et al. |
| 2017/0212723 | A1 | 7/2017 | Atarot et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2017/0231710 | A1 | 8/2017 | Scholl et al. |
| 2017/0258426 | A1 | 9/2017 | Risher-Kelly et al. |
| 2017/0273748 | A1 | 9/2017 | Hourtash et al. |
| 2017/0296277 | A1 | 10/2017 | Hourtash et al. |
| 2017/0348007 | A1 | 12/2017 | Shiels |
| 2017/0360493 | A1 | 12/2017 | Zucher et al. |
| 2018/0132839 | A1 | 5/2018 | Friedrich et al. |
| 2018/0228351 | A1 | 8/2018 | Scott et al. |
| 2019/0083191 | A1 | 3/2019 | Gilhooley et al. |
| 2019/0307509 | A1 | 10/2019 | Jansen et al. |
| 2020/0155238 | A1* | 5/2020 | Tillett ................ A61B 17/3472 |
| 2020/0170723 | A1* | 6/2020 | Crawford ............... A61B 34/10 |
| 2021/0156409 | A1* | 5/2021 | Lindenmann .......... A61B 34/20 |

FOREIGN PATENT DOCUMENTS

| | | | |
|---|---|---|---|
| CN | 107072784 | A | 8/2017 |
| CN | 209723817 | U | 12/2019 |
| JP | 2002523170 | A | 7/2002 |
| JP | 2002535068 | A | 10/2002 |
| JP | 2004500916 | A | 1/2004 |
| JP | 2004512136 | A | 4/2004 |
| JP | 2005013737 | A | 1/2005 |
| JP | 2006509609 | A | 3/2006 |
| JP | 2006102501 | A | 4/2006 |
| JP | 2008538184 | A | 10/2008 |
| JP | 2009515650 | A | 4/2009 |
| JP | 2010540180 | A | 12/2010 |
| JP | 2011172920 | A | 9/2011 |
| JP | 2013541966 | A | 11/2013 |
| JP | 2018509277 | A | 4/2018 |
| JP | 2019088781 | A | 6/2019 |
| WO | 2007096322 | A2 | 8/2007 |
| WO | 2014045165 | A1 | 3/2014 |
| WO | 2018104523 | A1 | 6/2018 |
| WO | 2019032849 | A2 | 2/2019 |

* cited by examiner

2200

2100

2214

SYSTEMS AND METHODS FOR FIXATING A NAVIGATION ARRAY

CROSS-REFERENCE TO RELATED APPLICATIONS

The present application is a continuation-in-part of U.S. application Ser. No. 16/841,927, filed on Apr. 7, 2020, which is a continuation-in-part of U.S. application Ser. No. 16/737,054, filed on Jan. 8, 2020, which is a continuation-in-part of U.S. application Ser. No. 16/587,203, filed on Sep. 30, 2019. U.S. application Ser. No. 16/737,054 also claims the benefit of U.S. Provisional Application No. 62/906,831, filed on Sep. 27, 2019. The contents of each of these applications are incorporated herein by reference in their entirety for all purposes.

FIELD

The present disclosure relates to medical devices and systems, and more particularly, robotic systems and related end effectors for controlling cutting of anatomical structures of a patient, and related methods and devices.

BACKGROUND

Total Knee Arthroplasty (TKA) involves placing implants on resected surfaces on the distal femur and proximal tibia. The location and orientation of the resection plans defines the location and orientation of the implant which in turn impacts patient outcomes. There is a desire among surgeons to place implants using navigation techniques, which enables them to precisely plan and place the implant more in accordance with the patient's existing anatomy.

In cases where navigation is used, some kind of reference to the human anatomy is needed to allow the robotic system to orient, align and perform surgical actions correctly. Although a wide range of methods can be employed, one method includes placing optical reference/tracking arrays (further referred to as an "array") rigidly to the anatomy and referencing them to a global coordinate system. To guarantee a rigid connection, especially in the case of orthopedic surgery, cortical pins may be placed into the bone and the array may be connected to the cortical pins.

Some requirements for the placement and function of the pins may be (1) a rigid connection between anatomical structure (bone) and array; (2) no undesired rotation of the array in relation to the referenced anatomical structure; (3) no undesired translation/bending of the array in relation to the referenced anatomical structure; (4) as little soft tissue damage as possible; (5) as little bone damage as possible; (6) as little risk for nerve/vascular damage as possible; (7) as much minimally invasive as possible; and (8) placement by one person, manually without requirement of navigation.

Using cortical pins to place navigation arrays on femur and tibia, however, may have some disadvantages. For example, two incisions may be needed to place the pins, increasing risk of infection and time for the procedure. Unintentional piercing through the bone may result in a less stable bone at the end of the procedure and increases spots for the patient's body to heal. Placing the pins in the right orientation and pattern/distance is only possible with a jig, or (after many procedures) by experience, hence difficult for unexperienced surgeons. The piercing depth and angular orientation and position may arbitrary and thus depended on experience. The risk of breaking bone increases with number of implanted pins and holes in cortical walls.

What is needed, therefore, is a device and/or method fulfilling the above-mentioned eight requirements to rigidly connect an optical navigation array to a human anatomical structure, especially bones, such as the tibia and femur. Other fields of applications such as use with other bony structures, use in animals, use to rigidly connect broken bones, or use for fixation of structures other than optical tracking arrays, may also be included.

SUMMARY

Some embodiments of the present disclosure are directed to a fixation device for securing a navigation array to a bony structure for use in a robotic-assisted surgery. The fixation device includes a trocar, a cortical pin configured to be inserted into the trocar, and a dowel configured to be attached to the cortical pin. The dowel is configured to prevent rotation of the cortical pin in the bony structure. The fixation device includes a navigation array configured to be removably attached to the cortical pin.

Some embodiments of the present disclosure are directed to a method for performing a knee arthroplasty surgery, using a fixation device for securing a navigation array to a bony structure, for use in a robotic-assisted surgery. The method includes inserting a trocar through an incision in soft tissue of a patient, inserting a cortical pin through the trocar into bone of the patient, and deploying a dowel into the bone. The dowel is disposed at a tip of the cortical pin and configured to be disposed in the bone in a manner to prevent rotation of the fixation device. The method includes attaching a navigation array to the cortical pin and registering a patient to a navigation system.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Figure 1:
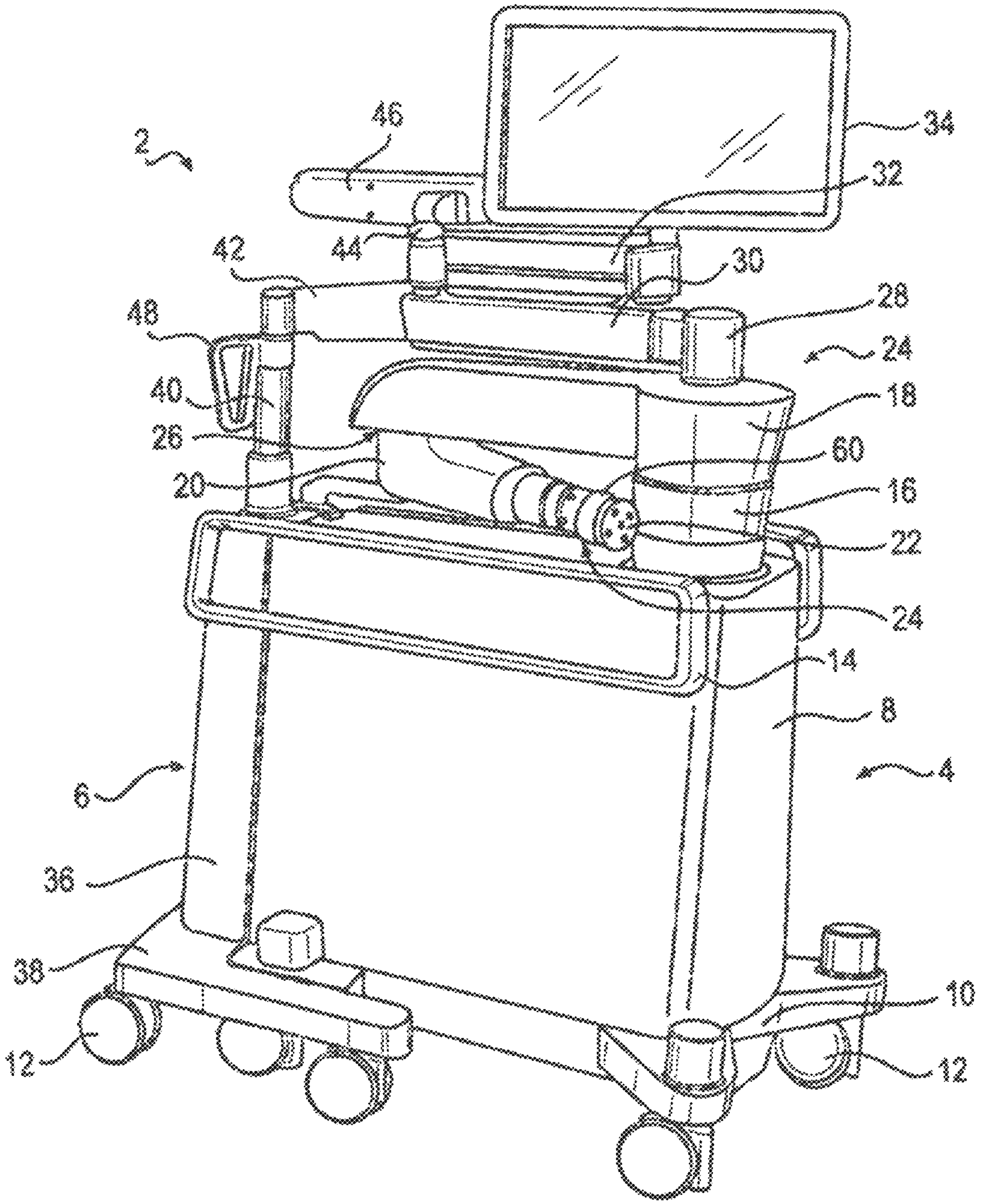
FIG. 1 illustrates an embodiment of a surgical system according to some embodiments of the present disclosure.

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in operation of a surgical system when performing surgical interventions requiring osteotomy. Passive end effectors are disclosed that are connectable to a robot arm positioned by a surgical robot. The passive end effectors have pairs of mechanisms that constrain movement of a tool attachment mechanism to a range of movement. The tool attachment is connectable to a surgical saw for cutting, such as a sagittal saw having an oscillating saw blade. The mechanisms may be configured to constrain a cutting plane of the saw blade to be parallel to the working plane. The surgical robot can determine a pose of the target plane based on a surgical plan defining where an anatomical structure is to be cut and based on a pose of the anatomical structure, and can generate steering information based on comparison of the pose of the target plane and the pose of the surgical saw. The steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

These and other related embodiments can operate to improve the precision of the guidance of the saw blade compared to other robotic and manual (e.g., jigs) solutions for surgeries. The mechanisms of the passive end effector can allow the surgeon to concentrate on interpreting the direct force feedback while cutting bones using a surgical saw that is guided by the passive end effector. The mechanisms may be planar mechanism, e.g., having 1 to 3 adequately selected degrees of freedom (e.g. one translation or rotation, two rotations, three rotations, or other combinations, etc.) end joint that is configured to constrain the cutting plane to be aligned with the target plane. The surgeon may also more accurately monitor and control the speed of bone removal based on audio and/or visual notification feedback provided through the surgical robot.

These embodiments can provide guidance during joint surgeries and especially knee surgery with high precision, high rigidity, sufficient workspace and direct force feedback. As will be explained in detail below, a tracking system can be used to precisely align the cutting plane with the target plane for cutting a bone. High precision cuts may be achieved by the planar mechanisms constraining the cutting plane to remaining aligned with the target plane while a surgeon moves the saw blade along the cutting plane and directly senses force feedback of the saw blade cutting bone. Moreover, these embodiments can be rapidly deployed into surgical practices through defined changes in existing accepted surgery workflows.

FIG. 1 illustrates an embodiment of a surgical system 2 according to some embodiments of the present disclosure. Prior to performance of an orthopedic surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or Mill. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the surgical system computer platform 900 of FIG. 9 which includes the surgical robot 800 (e.g., robot 2 in FIG. 1) and a surgical planning computer 910. A surgeon reviewing the image scan(s) on a display device of the surgical planning computer 910 (FIG. 9) generates a surgical plan defining a target plane where an anatomical structure of the patient is to be cut. This plane is a function of patient anatomy constraints, selected implant and its size. In some embodiments, the surgical plan defining the target plane is planned on the 3D image scan displayed on a display device.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system 6. Both systems may be mechanically coupled together by any various mechanisms. Suitable mechanisms can include, but are not limited to, mechanical latches, ties, clamps, or buttresses, or magnetic or magnetized surfaces. The ability to mechanically couple surgical robot 4 and camera tracking system 6 can allow for surgical system 2 to maneuver and move as a single unit, and allow surgical system 2 to have a small footprint in an area, allow easier movement through narrow passages and around turns, and allow storage within a smaller area.

An orthopedic surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system 6. Surgical robot 4 may be positioned adjacent the patient at any suitable location to properly assist medical personnel. Camera tracking system 6 may be positioned at the base of the patient, at patient shoulders or any other location suitable to track the present pose and movement of the pose of tracks portions of the surgical robot 4 and the patient. Surgical robot 4 and camera tracking system 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support arm 16. In some embodiments, robot body 8 may be made of any suitable material. Suitable material may be, but is not limited to, metal such as titanium, aluminum, or stainless steel, carbon fiber, fiberglass, or heavy-duty plastic. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may be made of any suitable material. Suitable material may be, but is not limited to, metal such as titanium, aluminum, or stainless steel, carbon fiber, fiberglass, or heavy-duty plastic or resin. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. Suitable metal may be, but is not limited to, stainless steel, aluminum, or titanium. Additionally, the rod may comprise at the contact-surface-side end a buffer, not pictured, which may prevent the rod from slipping and/or create a suitable contact surface. The material may be any suitable material to act as a buffer. Suitable material may be, but is not limited to, a plastic, neoprene, rubber, or textured metal. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may be made of any suitable material. Suitable material may be, but is not limited to, metal such as titanium, aluminum, or stainless steel, carbon fiber, fiberglass, or heavy-duty plastic. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. Robot telescoping support 16 may be made of any suitable material. Suitable material may be, but is not limited to, metal such as titanium or stainless steel, carbon fiber, fiberglass, or heavy-duty plastic. The body of robot telescoping support 16 may be any width and/or height in which to support the stress and weight placed upon it.

In some embodiments, medical personnel may move SCARA 24 through a command submitted by the medical personnel. The command may originate from input received on display 34 and/or a tablet. The command may come from the depression of a switch and/or the depression of a plurality of switches. Best illustrated in FIGS. 4 and 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 easily. Additionally, when the SCARA 24 is not receiving a command to move, the SCARA 24 may lock in place to prevent accidental movement by personnel and/or other objects. By locking in place, the SCARA 24 provides a solid platform upon which a passive end effector 1100 and connected surgical saw 1140, shown in FIGS. 4 and 5, are ready for use in a medical operation.

Robot support arm 18 may be disposed on robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location. Robot arm 20 may attach to robot support arm 16 by various mechanisms. Suitable mechanisms may be, but is not limited to, nuts and bolts, ball and socket fitting, press fitting, weld, adhesion, screws, rivets, clamps, latches, and/or any combination thereof. Robot arm 20 may rotate in any direction in regards to robot support arm 18, in embodiments, robot arm 20 may rotate three hundred and sixty degrees in regards to robot support arm 18. This free rotation may allow an operator to position robot arm 20 as planned.

Figure 4:
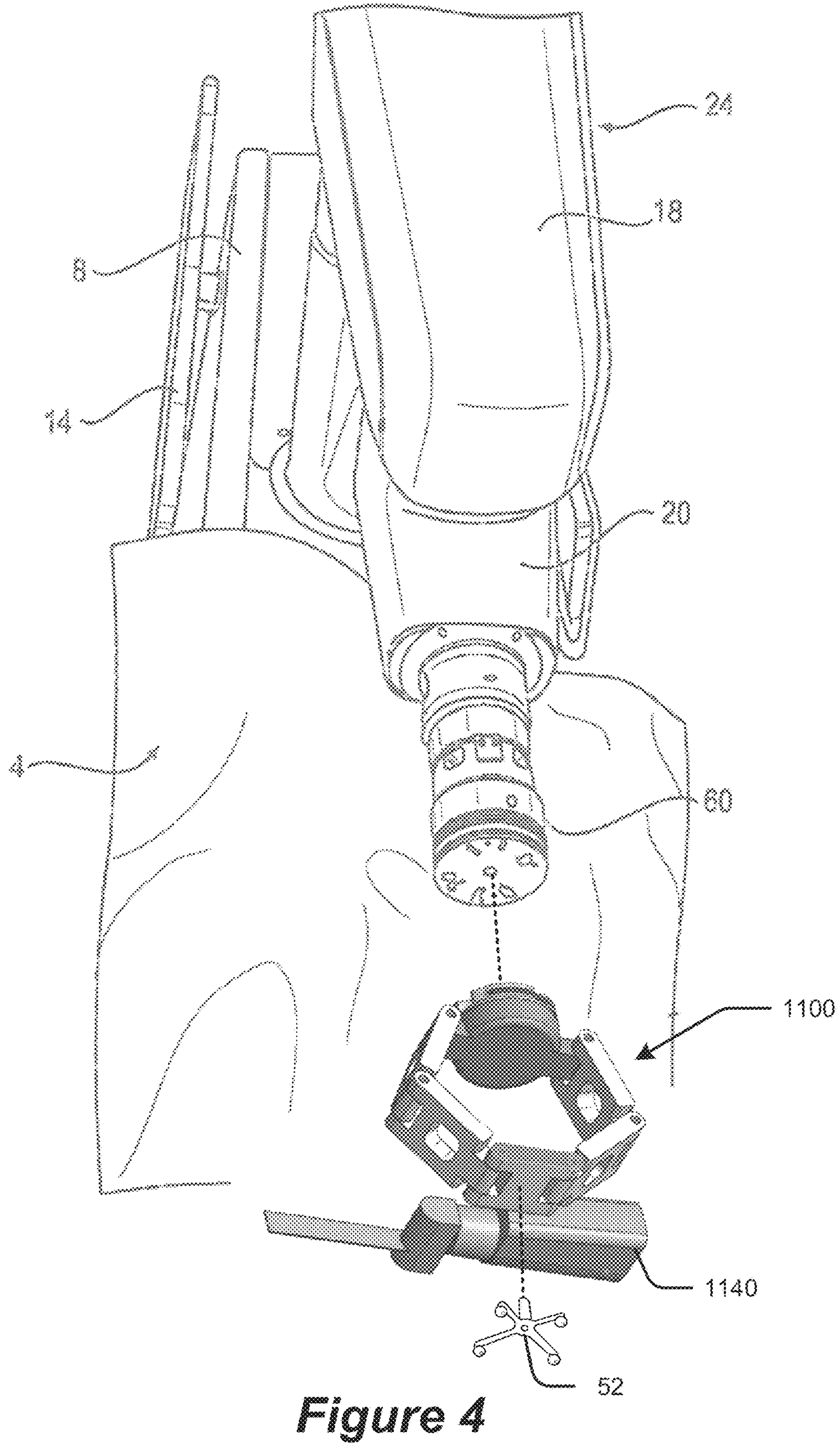
FIG. 4 illustrates an embodiment of a passive end effector that is connectable to a robot arm and configured according to some embodiments of the present disclosure.
Figure 5:
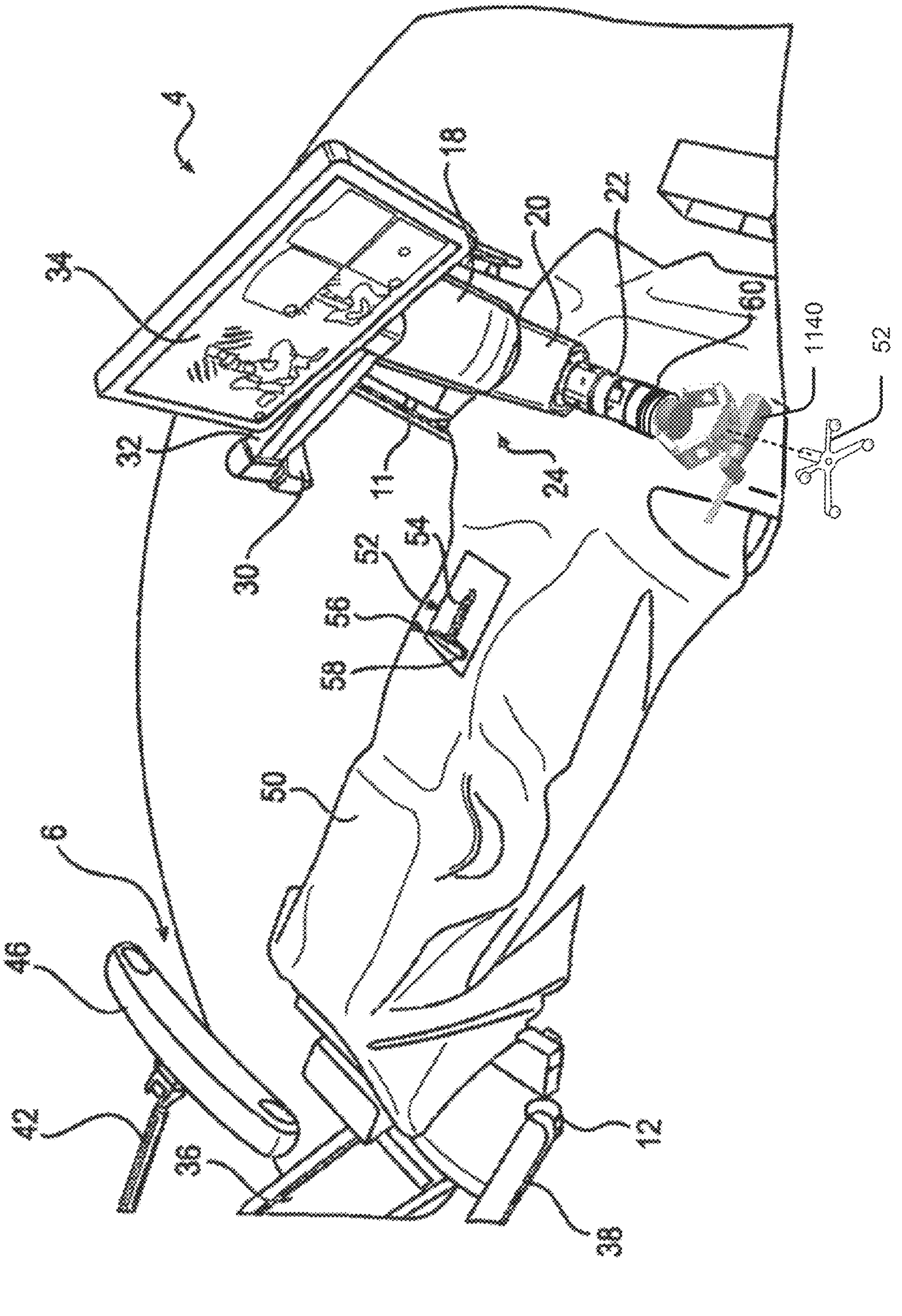
FIG. 5 illustrates a medical operation in which a surgical robot and a camera system are disposed around a patient.

The passive end effector 1100 in FIGS. 4 and 5 may attach to robot arm 20 in any suitable location. As will be explained in further detail below, the passive end effector 1100 includes a base, a first mechanism, and a second mechanism. The base is configured to attach to an end effector coupler 22 of the robot arm 20 positioned by the surgical robot 4. Various mechanisms by which the base can attach to the end effector coupler 22 can include, but are not limited to, latch, clamp, nuts and bolts, ball and socket fitting, press fitting, weld, adhesion, screws, rivets, and/or any combination thereof. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections, and may be configured to constrain movement of the tool attachment mechanism to a range of movement within a working plane. The rotatable connections may be pivot joints allowing 1 degree-of-freedom (DOF) motion, universal joints allowing 2 DOF motions, or ball joints allowing 3 DOF motions. The tool attachment mechanism is configured to connect to a surgical saw 1140 having a saw blade or saw blade directly. The surgical saw 1140 may be configured to oscillate the saw blade for cutting. The first and second mechanisms may be configured to constrain a cutting plane of the saw blade to be parallel to the working plane. Pivot joints may be preferably used for connecting the planar mechanisms when the passive end effector is to be configured to constrain motion of the saw blade to the cutting plane.

The tool attachment mechanism may connect to the surgical saw 1140 or saw blade through various mechanisms that can include, but are not limited to, a screw, nut and bolt, clamp, latch, tie, press fit, or magnet. In some embodiments, a dynamic reference array 52 is attached to the passive end effector 1100, e.g., to the tool attachment mechanism, and/or is attached to the surgical saw 1140. Dynamic reference arrays, also referred to as "DRAs" herein, are rigid bodies which may be disposed on a patient, the surgical robot, the passive end effector, and/or the surgical saw in a navigated surgical procedure. The camera tracking system 6 or other 3D localization system is configured to track in real-time the pose (e.g., positions and rotational orientations) of tracking markers of the DRA. The tracking markers may include the illustrated arrangement of balls or other optical markers. This tracking of 3D coordinates of tracking markers can allow the surgical system 2 to determine the pose of the DRA 52 in any space in relation to the target anatomical structure of the patient 50 in FIG. 5.

As illustrated in FIG. 1, a light indicator 28 may be positioned on top of the SCARA 24. Light indicator 28 may illuminate as any type of light to indicate "conditions" in which surgical system 2 is currently operating. For example, the illumination of green may indicate that all systems are normal. Illuminating red may indicate that surgical system 2 is not operating normally. A pulsating light may mean surgical system 2 is performing a function. Combinations of light and pulsation may create a nearly limitless amount of combinations in which to communicate the current operating conditions, states, or other operational indications. In some embodiments, the light may be produced by LED bulbs, which may form a ring around light indicator 28. Light indicator 28 may comprise a fully permeable material that may let light shine through the entirety of light indicator 28.

Figure 2:
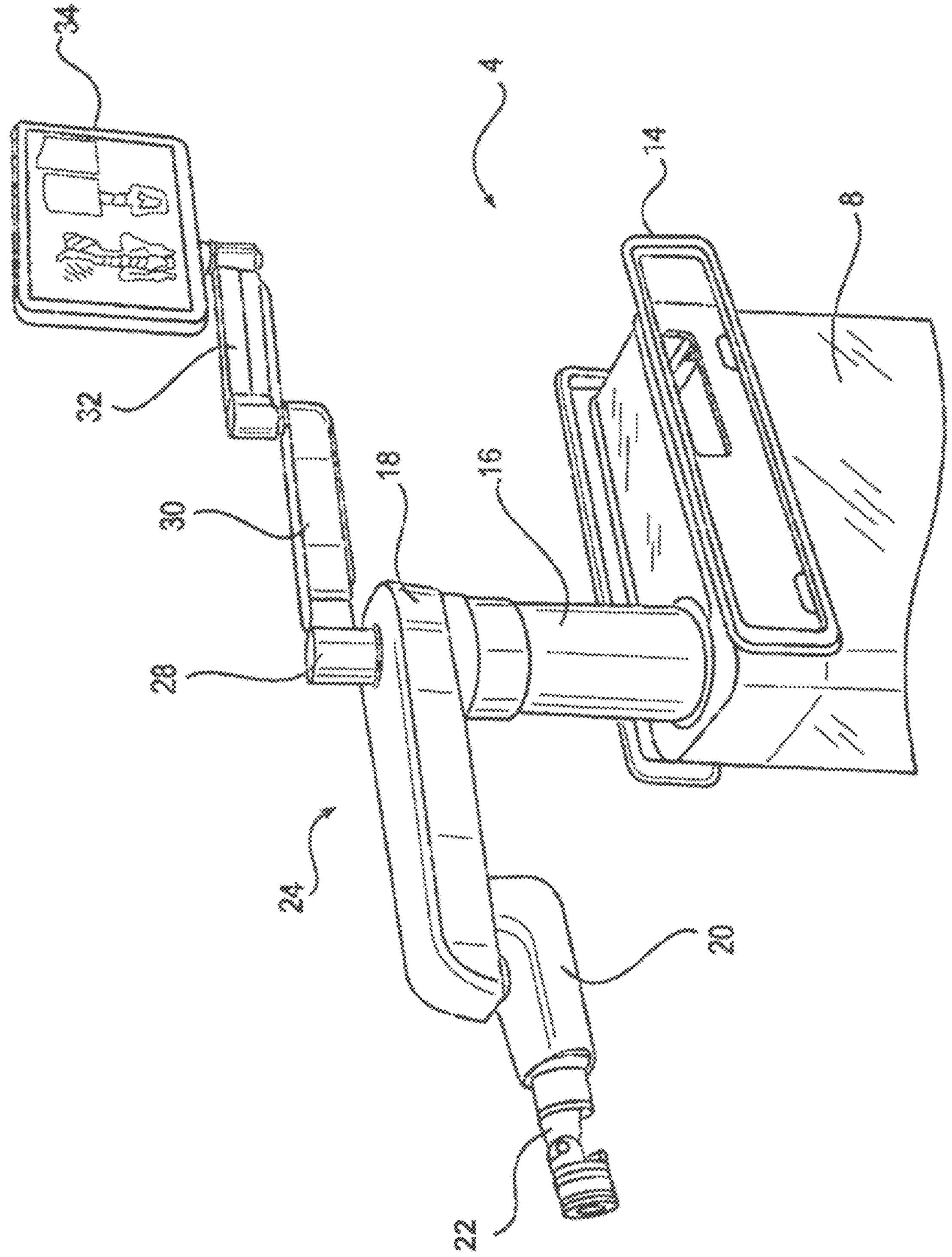
FIG. 2 illustrates a surgical robot component of the surgical system of FIG. 1 according to some embodiments of the present disclosure.

Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In embodiments, lower display support 30 may rotate about light indicator 28. In embodiments, lower display support 30 may attach rigidly to light indicator 28. Light indicator 28 may then rotate three hundred and sixty degrees about robot support arm 18. Lower display support 30 may be of any suitable length, a suitable length may be about eight inches to about thirty four inches. Lower display support 30 may act as a base for upper display support 32.

Upper display support 32 may attach to lower display support 30 by any suitable mechanism. Upper display support 32 may be of any suitable length, a suitable length may be about eight inches to about thirty four inches. In embodiments, as illustrated in FIG. 1, upper display support 32 may allow display 34 to rotate three hundred and sixty degrees in relation to upper display support 32. Likewise, upper display support 32 may rotate three hundred and sixty degrees in relation to lower display support 30.

Display 34 may be any device which may be supported by upper display support 32. In embodiments, as illustrated in FIG. 2, display 34 may produce color and/or black and white images. The width of display 34 may be about eight inches to about thirty inches wide. The height of display 34 may be about six inches to about twenty two inches tall. The depth of display 34 may be about one-half inch to about four inches.

In embodiments, a tablet may be used in conjunction with display 34 and/or without display 34. In embodiments, the table may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As illustrated in FIG. 5, camera tracking system 6 works in conjunction with surgical robot 4 through wired or wireless communication networks. Referring to FIGS. 1 and 5, camera tracking system 6 can include some similar components to the surgical robot 4. For example, camera body 36 may provide the functionality found in robot body 8. Robot body 8 may provide the structure upon which camera 46 is mounted. The structure within robot body 8 may also provide support for the electronics, communication devices, and power supplies used to operate camera tracking system 6. Camera body 36 may be made of the same material as robot body 8. Camera tracking system 6 may communicate directly to the tablet and/or display 34 by a wireless and/or wired network to enable the tablet and/or display 34 to control the functions of camera tracking system 6.

Camera body 36 is supported by camera base 38. Camera base 38 may function as robot base 10. In the embodiment of FIG. 1, camera base 38 may be wider than robot base 10. The width of camera base 38 may allow for camera tracking system 6 to connect with surgical robot 4. As illustrated in FIG. 1, the width of camera base 38 may be large enough to fit outside robot base 10. When camera tracking system 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system 6 to stabilize and level or set fixed orientation in regards to patient 50, similar to the operation of robot base 10 and powered wheels 12. This stabilization may prevent camera tracking system 6 from moving during a medical procedure and may keep camera 46 from losing track of one or more DRAs 52 connected to an anatomical structure 54 and/or tool 58 within a designated area 56 as shown in FIG. 5. This stability and maintenance of tracking enhances the ability of surgical robot 4 to operate effectively with camera tracking system 6. Additionally, the wide camera base 38 may provide additional support to camera tracking system 6. Specifically, a wide camera base 38 may prevent camera tracking system 6 from tipping over when camera 46 is disposed over a patient, as illustrated in FIG. 5. Without the wide camera base 38, the outstretched camera 46 may unbalance camera tracking system 6, which may result in camera tracking system 6 falling over.

Camera telescoping support 40 may support camera 46. In embodiments, telescoping support 40 may move camera 46 higher or lower in the vertical direction. Telescoping support 40 may be made of any suitable material in which to support camera 46. Suitable material may be, but is not limited to, metal such as titanium, aluminum, or stainless steel, carbon fiber, fiberglass, or heavy-duty plastic. Camera handle 48 may be attached to camera telescoping support 40 at any suitable location. Cameral handle 48 may be any suitable handle configuration. A suitable configuration may be, but is not limited to, a bar, circular, triangular, square, and/or any combination thereof. As illustrated in FIG. 1, camera handle 48 may be triangular, allowing an operator to move camera tracking system 6 into a planned position before a medical operation. In embodiments, camera handle 48 may be used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position camera 46 in any suitable location. Lower camera support arm 42 may be made of any suitable material in which to support camera 46. Suitable material may be, but is not limited to, metal such as titanium, aluminum, or stainless steel, carbon fiber, fiberglass, or heavy-duty plastic. Cross-section of lower camera support arm 42 may be any suitable shape. Suitable cross-sectional shape may be, but is not limited to, circle, square, rectangle, hexagon, octagon, or i-beam. The cross-sectional length and width may be about one to ten inches. Length of the lower camera support arm may be about four inches to about thirty-six inches. Lower camera support arm 42 may connect to telescoping support 40 by any suitable mechanism. Suitable mechanism may be, but is not limited to, nuts and bolts, ball and socket fitting, press fitting, weld, adhesion, screws, rivets, clamps, latches, and/or any combination thereof. Lower camera support arm 42 may be used to provide support for camera 46. Camera 46 may be attached to lower camera support arm 42 by any suitable mechanism. Suitable mechanism may be, but is not limited to, nuts and bolts, ball and socket fitting, press fitting, weld, adhesion, screws, rivets, and/or any combination thereof. Camera 46 may pivot in any direction at the attachment area between camera 46 and lower camera support arm 42. In embodiments a curved rail 44 may be disposed on lower camera support arm 42.

Figure 3:
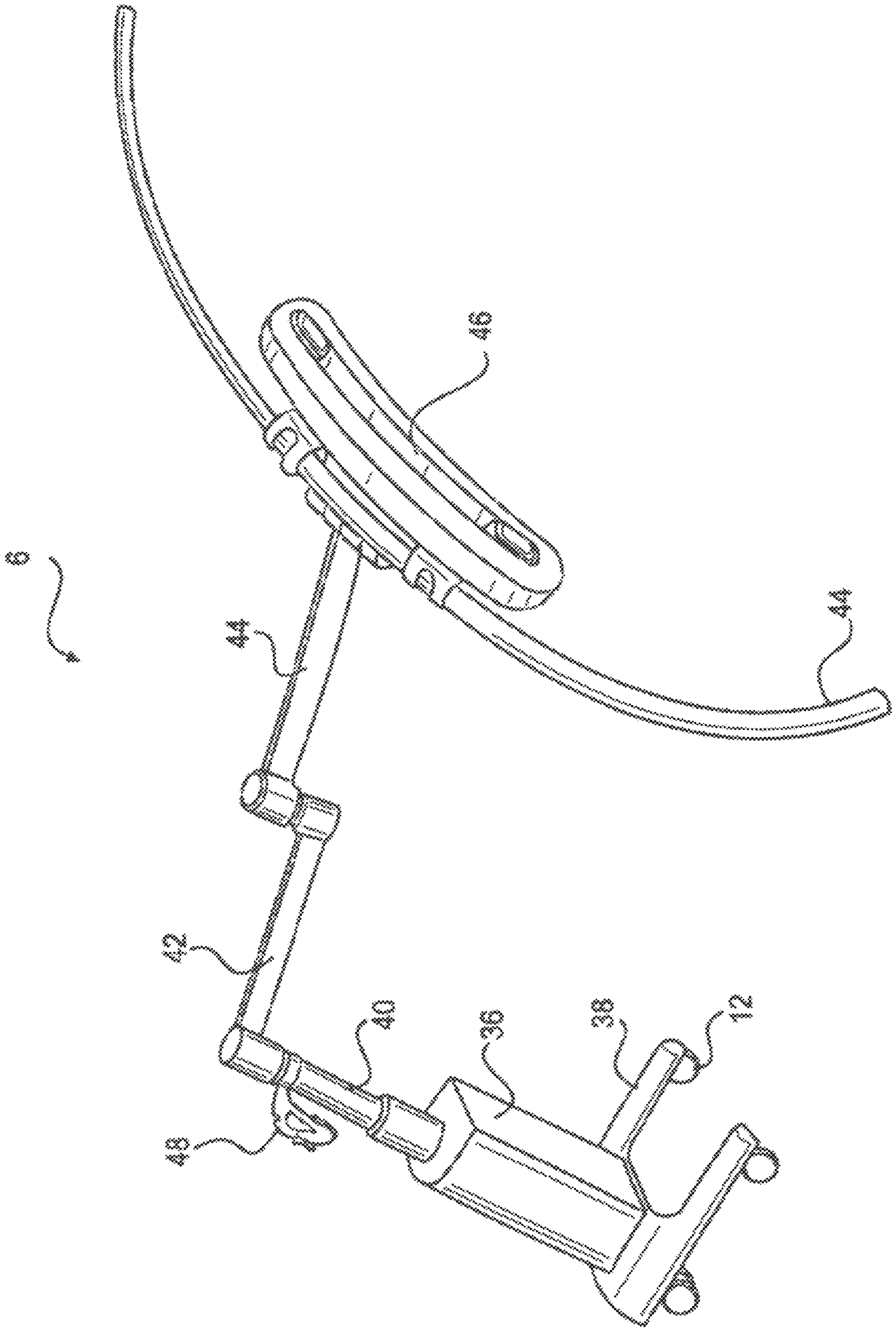
FIG. 3 illustrates a camera tracking system component of the surgical system of FIG. 1 according to some embodiments of the present disclosure.

Curved rail 44 may be disposed at any suitable location on lower camera support arm 42. As illustrated in FIG. 3, curved rail 44 may attach to lower camera support arm 42 by any suitable mechanism. Suitable mechanism may be, but are not limited to nuts and bolts, ball and socket fitting, press fitting, weld, adhesion, screws, rivets, clamps, latches, and/or any combination thereof. Curved rail 44 may be of any suitable shape, a suitable shape may be a crescent, circular, oval, elliptical, and/or any combination thereof. In embodiments, curved rail 44 may be any appropriate length. An appropriate length may be about one foot to about six feet. Camera 46 may be moveably disposed along curved rail 44. Camera 46 may attach to curved rail 44 by any suitable mechanism. Suitable mechanism may be, but are not limited to rollers, brackets, braces, motors, and/or any combination thereof. Motors and rollers, not illustrated, may be used to move camera 46 along curved rail 44. As illustrated in FIG. 3, during a medical procedure, if an object prevents camera 46 from viewing one or more DRAs 52, the motors may move camera 46 along curved rail 44 using rollers. This motorized movement may allow camera 46 to move to a new position that is no longer obstructed by the object without moving camera tracking system 6. While camera 46 is obstructed from viewing DRAs 52, camera tracking system 6 may send a stop signal to surgical robot 4, display 34, and/or a tablet. The stop signal may prevent SCARA 24 from moving until camera 46 has reacquired DRAs 52. This stoppage may prevent SCARA 24 and/or end effector coupler 22 from moving and/or using medical tools without being tracked by surgical system 2.

Figure 6:
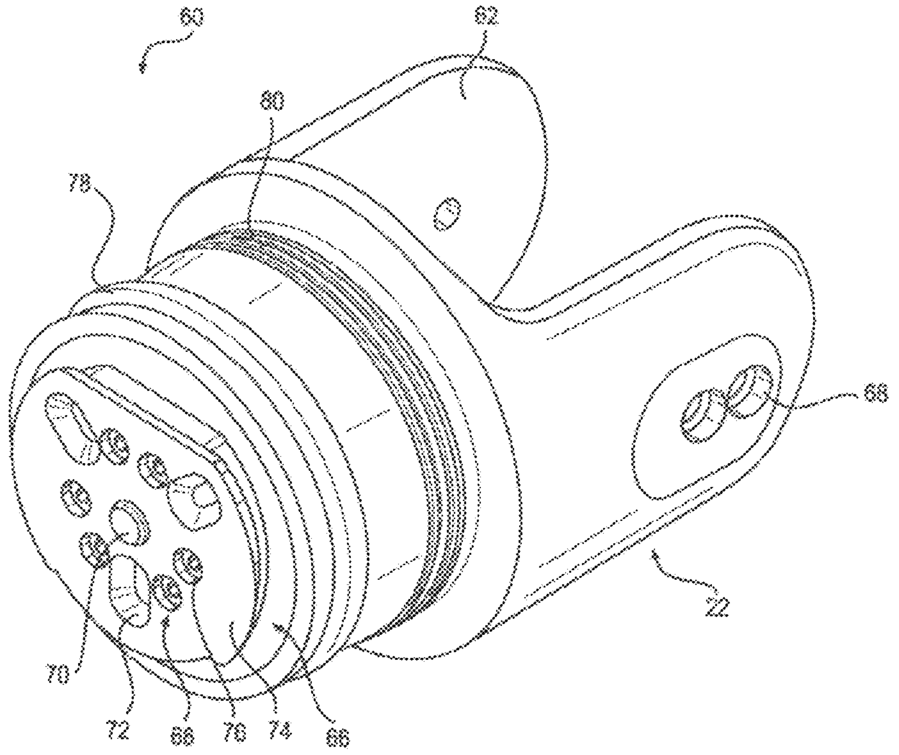
FIG. 6 illustrates an embodiment of an end effector coupler of a robot arm configured for connection to a passive end effector according to some embodiments of the present disclosure.

End effector coupler 22, as illustrated in FIG. 6, is configured to connect various types of passive end effectors to surgical robot 4. End effector coupler 22 can include a saddle joint 62, an activation assembly 60, a load cell 64 (FIG. 7), and a connector 66. Saddle joint 62 may attach end effector coupler 22 to SCARA 24. Saddle joint 62 may be made of any suitable material. Suitable material may be, but is not limited to metal such as titanium, aluminum, or stainless steel, carbon fiber, fiberglass, or heavy-duty plastic. Saddle joint 62 may be made of a single piece of metal which may provide end effector with additional strength and durability. The saddle joint 62 may attach to SCARA 24 by an attachment point 68. There may be a plurality of attachment points 68 disposed about saddle joint 62. Attachment points 68 may be sunk, flush, and/or disposed upon saddle joint 62. In some examples, screws, nuts and bolts, and/or any combination thereof may pass through attachment point 68 and secure saddle joint 62 to SCARA 24. The nuts and bolts may connect saddle joint 62 to a motor, not illustrated, within SCARA 24. The motor may move saddle joint 62 in any direction. The motor may further prevent saddle joint 62 from moving from accidental bumps and/or accidental touches by actively servoing at the current location or passively by applying spring actuated brakes.

Figure 7:
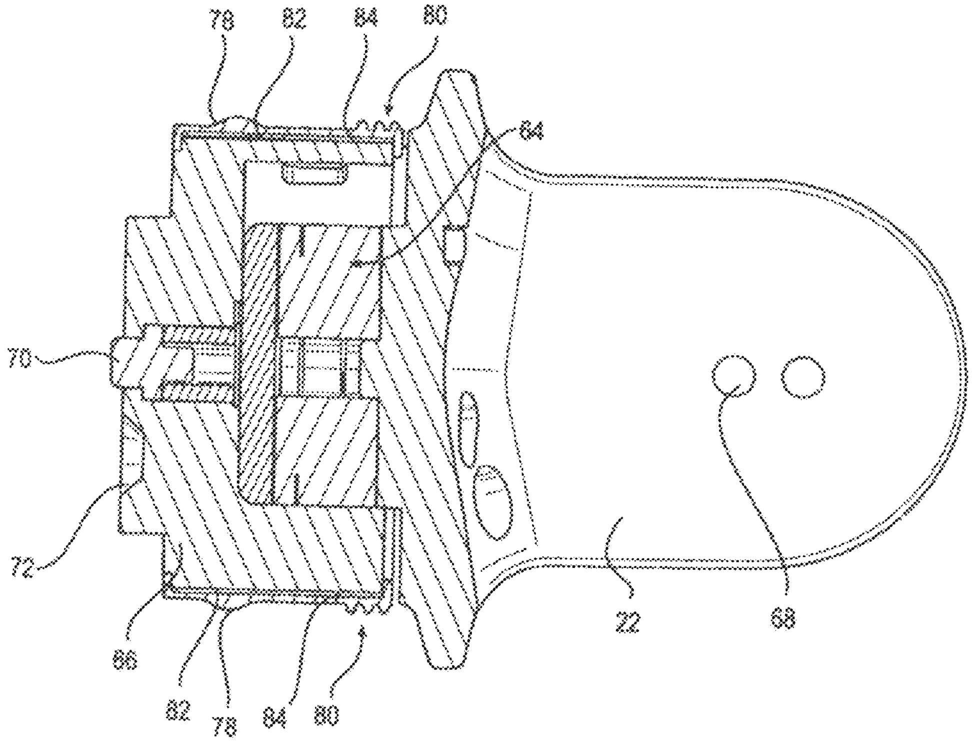
FIG. 7 illustrates an embodiment of a cut away of the end effector coupler of FIG. 6.

The end effector coupler 22 can include a load cell 64 interposed between the saddle join 62 and a connected passive end effector. Load cell 64, as illustrated in FIG. 7 may attach to saddle joint 62 by any suitable mechanism. Suitable mechanism may be, but is not limited to, screws, nuts and bolts, threading, press fitting, and/or any combination thereof.

Figure 8:
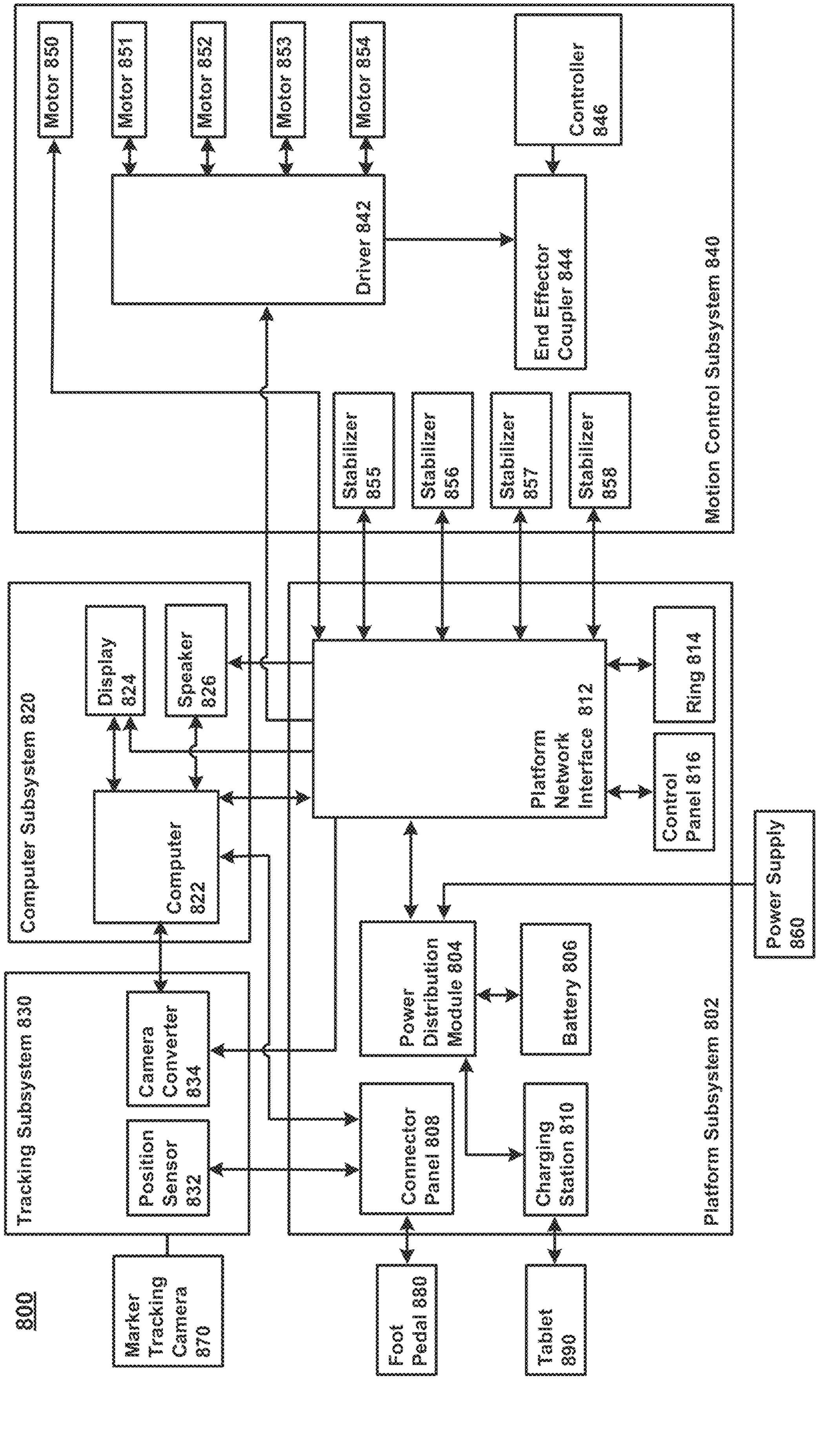
FIG. 8 illustrates a block diagram of components of a surgical system according to some embodiments of the present disclosure.

FIG. 8 illustrates a block diagram of components of a surgical system 800 according to some embodiments of the present disclosure. Referring to FIGS. 7 and 8, load cell 64 may be any suitable instrument used to detect and measure forces. In some examples, load cell 64 may be a six axis load cell, a three-axis load cell or a uniaxial load cell. Load cell 64 may be used to track the force applied to end effector coupler 22. In some embodiments the load cell 64 may communicate with a plurality of motors 850, 851, 852, 853, and/or 854. As load cell 64 senses force, information as to the amount of force applied may be distributed from a switch array and/or a plurality of switch arrays to a controller 846. Controller 846 may take the force information from load cell 64 and process it with a switch algorithm. The switch algorithm is used by the controller 846 to control a motor driver 842. The motor driver 842 controls operation of one or more of the motors. Motor driver 842 may direct a specific motor to produce, for example, an equal amount of force measured by load cell 64 through the motor. In some embodiments, the force produced may come from a plurality of motors, e.g., 850-854, as directed by controller 846. Additionally, motor driver 842 may receive input from controller 846. Controller 846 may receive information from load cell 64 as to the direction of force sensed by load cell 64. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of passive end effector 1100 in the direction of force sensed by load cell 64. This force-controlled motion may allow an operator to move SCARA 24 and passive end effector 1100 effortlessly and/or with very little resistance. Movement of passive end effector 1100 can be performed to position passive end effector 1100 in any suitable pose (i.e., location and angular orientation relative to defined three-dimensional (3D) orthogonal reference axes) for use by medical personnel.

Connector 66 is configured to be connectable to the base of the passive end effector 1100 and is connected to load cell 64. Connector 66 can include attachment points 68, a sensory button 70, tool guides 72, and/or tool connections 74. Best illustrated in FIGS. 6 and 8, there may be a plurality of attachment points 68. Attachment points 68 may connect connector 66 to load cell 64. Attachment points 68 may be sunk, flush, and/or disposed upon connector 66. Attachment points 68 and 76 can be used to attach connector 66 to load cell 64 and/or to passive end effector 1100. In some examples, Attachment points 68 and 76 may include screws, nuts and bolts, press fittings, magnetic attachments, and/or any combination thereof.

As illustrated in FIG. 6, a sensory button 70 may be disposed about center of connector 66. Sensory button 70 may be depressed when a passive end effector 1100 is connected to SCARA 24. Depression of sensory button 70 may alert surgical robot 4, and in turn medical personnel, that a passive end effector 1100 has been attached to SCARA 24. As illustrated in FIG. 6, guides 72 may be used to facilitate proper attachment of passive end effector 1100 to SCARA 24. Guides 72 may be sunk, flush, and/or disposed upon connector 66. In some examples there may be a plurality of guides 72 and may have any suitable patterns and may be oriented in any suitable direction. Guides 72 may be any suitable shape to facilitate attachment of passive end effector 1100 to SCARA 24. A suitable shape may be, but is not limited to, circular, oval, square, polyhedral, and/or any combination thereof. Additionally, guides 72 may be cut with a bevel, straight, and/or any combination thereof.

Connector 66 may have attachment points 74. As illustrated in FIG. 6, attachment points 74 may form a ledge and/or a plurality of ledges. Attachment points 74 may provide connector 66 a surface upon which passive end effector 1100 may clamp. In some embodiments, attachment points 74 are disposed about any surface of connector 66 and oriented in any suitable manner in relation to connector 66.

Activation assembly 60, best illustrated in FIGS. 6 and 7, may encircle connector 66. In some embodiments, activation assembly 60 may take the form of a bracelet that wraps around connector 66. In some embodiments, activation assembly 60, may be located in any suitable area within surgical system 2. In some examples, activation assembly 60 may be located on any part of SCARA 24, any part of end effector coupler 22, may be worn by medical personnel (and communicate wirelessly), and/or any combination thereof. Activation assembly 60 may be made of any suitable material. Suitable material may be, but is not limited to neoprene, plastic, rubber, gel, carbon fiber, fabric, and/or any combination thereof. Activation assembly 60 may comprise of a primary button 78 and a secondary button 80. Primary button 78 and secondary button 80 may encircle the entirety of connector 66.

Primary button 78 may be a single ridge, as illustrated in FIG. 6, which may encircle connector 66. In some examples, primary button 78 may be disposed upon activation assembly 60 along the end farthest away from saddle joint 62. Primary button 78 may be disposed upon primary activation switch 82, best illustrated on FIG. 7. Primary activation switch 82 may be disposed between connector 66 and activation assembly 60. In some examples, there may be a plurality of primary activation switches 82, which may be disposed adjacent and beneath primary button 78 along the entire length of primary button 78. Depressing primary button 78 upon primary activation switch 82 may allow an operator to move SCARA 24 and end effector coupler 22. As discussed above, once set in place, SCARA 24 and end effector coupler 22 may not move until an operator programs surgical robot 4 to move SCARA 24 and end effector coupler 22, or is moved using primary button 78 and primary activation switch 82. In some examples, it may require the depression of at least two non-adjacent primary activation switches 82 before SCARA 24 and end effector coupler 22 will respond to operator commands. Depression of at least two primary activation switches 82 may prevent the accidental movement of SCARA 24 and end effector coupler 22 during a medical procedure.

Activated by primary button 78 and primary activation switch 82, load cell 64 may measure the force magnitude and/or direction exerted upon end effector coupler 22 by an operator, i.e. medical personnel. This information may be transferred to motors within SCARA 24 that may be used to move SCARA 24 and end effector coupler 22. Information as to the magnitude and direction of force measured by load cell 64 may cause the motors to move SCARA 24 and end effector coupler 22 in the same direction as sensed by load cell 64. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

Secondary button 80, as illustrated in FIG. 6, may be disposed upon the end of activation assembly 60 closest to saddle joint 62. In some examples secondary button 80 may comprise a plurality of ridges. The plurality of ridges may be disposed adjacent to each other and may encircle connector 66. Additionally, secondary button 80 may be disposed upon secondary activation switch 84. Secondary activation switch 84, as illustrated in FIG. 7, may be disposed between secondary button 80 and connector 66. In some examples, secondary button 80 may be used by an operator as a "selection" device. During a medical operation, surgical robot 4 may notify medical personnel to certain conditions by display 34 and/or light indicator 28. Medical personnel may be prompted by surgical robot 4 to select a function, mode, and/or assess the condition of surgical system 2. Depressing secondary button 80 upon secondary activation switch 84 a single time may activate certain functions, modes, and/or acknowledge information communicated to medical personnel through display 34 and/or light indicator 28. Additionally, depressing secondary button 80 upon secondary activation switch 84 multiple times in rapid succession may activate additional functions, modes, and/or select information communicated to medical personnel through display 34 and/or light indicator 28. In some examples, at least two non-adjacent secondary activation switches 84 may be depressed before secondary button 80 may function properly. This requirement may prevent unintended use of secondary button 80 from accidental bumping by medical personnel upon activation assembly 60. Primary button 78 and secondary button 80 may use software architecture 86 to communicate commands of medical personnel to surgical system 2.

FIG. 8 illustrates a block diagram of components of a surgical system 800 configured according to some embodiments of the present disclosure, and which may correspond to the surgical system 2 above. Surgical system 800 includes platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical system 800 may also include a removable foot pedal 880 and removable tablet computer 890.

Input power is supplied to surgical system 800 via a power source which may be provided to power distribution module 804. Power distribution module 804 receives input power and is configured to generate different power supply voltages that are provided to other modules, components, and subsystems of surgical system 800. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical system 800. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical system 800 and/or associated components and modules. Connector panel 808 may contain one or more ports that receive lines or connections from different components. For example, connector panel 808 may have a ground terminal port that may ground surgical system 800 to other equipment, a port to connect foot pedal 880, a port to connect to tracking subsystem 830, which may include position sensor 832, camera converter 834, and marker tracking cameras 870. Connector panel 808 may also include other ports to allow USB, Ethernet, HDMI communications to other components, such as computer 822.

Control panel 816 may provide various buttons or indicators that control operation of surgical system 800 and/or provide information from surgical system 800 for observation by an operator. For example, control panel 816 may include buttons to power on or off surgical system 800, lift or lower vertical column 16, and lift or lower stabilizers 855-858 that may be designed to engage casters 12 to lock surgical system 800 from physically moving. Other buttons may stop surgical system 800 in the event of an emergency, which may remove all motor power and apply mechanical brakes to stop all motion from occurring. Control panel 816 may also have indicators notifying the operator of certain system conditions such as a line power indicator or status of charge for battery 806.

Computer 822 of computer subsystem 820 includes an operating system and software to operate assigned functions of surgical system 800. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of a head-mounted display component, or within another component of the surgical system 2. The display 824 may correspond to the display 34 shown in FIGS. 1 and 2, or may be a head-mounted display which projects images onto a see-through display screen which forms an augmented reality (AR) image that is overlaid on real-world objects viewable through the see-through display screen.

Tracking subsystem 830 may include position sensor 832 and camera converter 834. Tracking subsystem 830 may correspond to the camera tracking system 6 of FIG. 3. The marker tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective markers, respectively. The location, orientation, and position of structures having these types of markers, such as DRAs 52, is provided to computer 822 and which may be shown to an operator on display 824. For example, as shown in FIGS. 4 and 5, a surgical saw 1240 having a DRA 52 or which is connected to an end effector coupler 22 having a DRA 52 tracked in this manner (which may be referred to as a navigational space) may be shown to an operator in relation to a three dimensional image of a patient's anatomical structure.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The surgical planning computer 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be cut during a surgical procedure. Motion control subsystem 840 may be configured to measure position of the passive end effector structure using integrated position sensors (e.g. encoders). In one of the embodiments, position sensors are directly connected to at least one joint of the passive end effector structure, but may also be positioned in another location in the structure and remotely measure the joint position by interconnection of a timing belt, a wire, or any other synchronous transmission interconnection.

Figure 9:
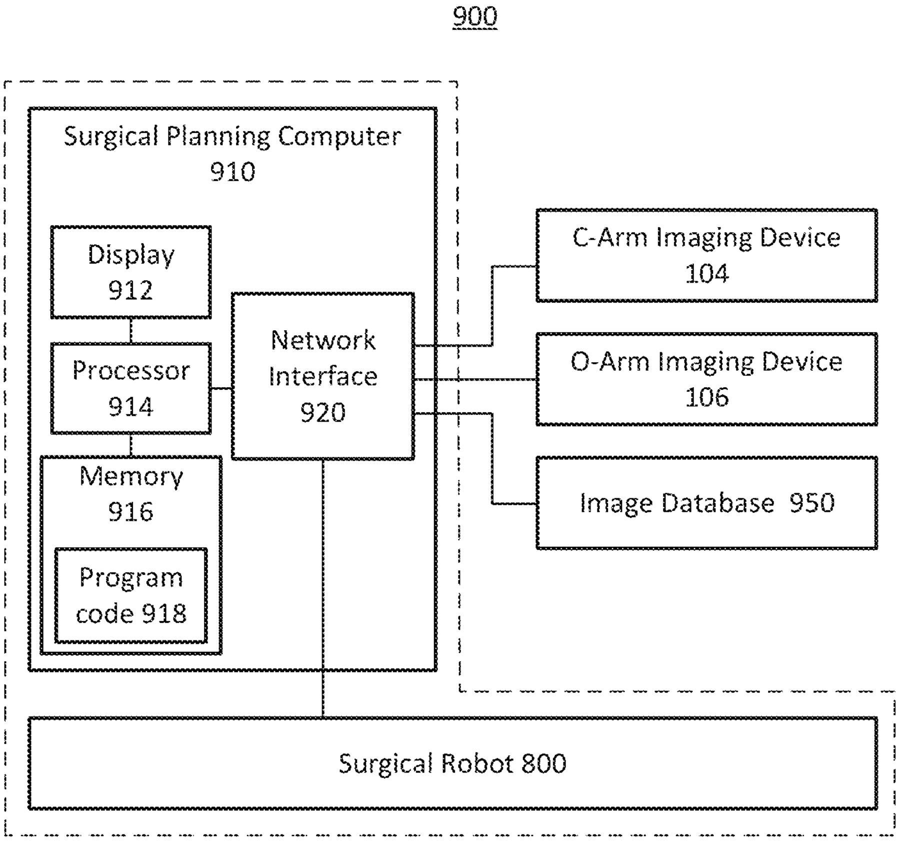
FIG. 9 illustrates a block diagram of a surgical system computer platform that includes a surgical planning computer which may be separate from and operationally connected to a surgical robot or at least partially incorporated therein according to some embodiments of the present disclosure.

FIG. 9 illustrates a block diagram of a surgical system computer platform 900 that includes a surgical planning computer 910 which may be separate from and operationally connected to a surgical robot 800 or at least partially incorporated therein according to some embodiments of the present disclosure. Alternatively, at least a portion of operations disclosed herein for the surgical planning computer 910 may be performed by components of the surgical robot 800 such as by the computer subsystem 820.

Referring to FIG. 9, the surgical planning computer 910 includes a display 912, at least one processor circuit 914 (also referred to as a processor for brevity), at least one memory circuit 916 (also referred to as a memory for brevity) containing computer readable program code 918, and at least one network interface 920 (also referred to as a network interface for brevity). The network interface 920 can be configured to connect to a C-Arm imaging device 104 in FIG. 10, an O-Arm imaging device 106 in FIG. 11, another medical imaging device, an image database 950 of medical images, components of the surgical robot 800, and/or other electronic equipment.

When the surgical planning computer 910 is at least partially integrated within the surgical robot 800, the display 912 may correspond to the display 34 of FIG. 2 and/or the tablet 890 of FIG. 8 and/or a head-mounted display, the network interface 920 may correspond to the platform network interface 812 of FIG. 8, and the processor 914 may correspond to the computer 822 of FIG. 8.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed by a surgical planning computer.

The processor 914 can operate to display on the display device 912 an image of a bone that is received from one of the imaging devices 104 and 106 and/or from the image database 950 through the network interface 920. The processor 914 receives an operator's definition of where an anatomical structure, i.e. one or more bones, shown in one or more images is to be cut, such as by an operator touch selecting locations on the display 912 for planned surgical cuts or using a mouse-based cursor to define locations for planned surgical cuts.

The surgical planning computer 910 enables anatomy measurement, useful for knee surgery, like measurement of various angles determining center of hip, center of angles, natural landmarks (e.g. transepicondylar line, Whitesides line, posterior condylar line etc.), etc. Some measurements can be automatic while some others involve human input or assistance. This surgical planning computer 910 allows an operator to choose the correct implant for a patient, including choice of size and alignment. The surgical planning computer 910 enables automatic or semi-automatic (involving human input) segmentation (image processing) for CT images or other medical images. The surgical plan for a patient may be stored in a cloud-based server for retrieval by the surgical robot 800. During the surgery, the surgeon will choose which cut to make (e.g. posterior femur, proximal tibia etc.) using a computer screen (e.g. touchscreen) or augmented reality interaction via, e.g., a head-mounted display. The surgical robot 4 may automatically move the surgical saw blade to a planned position so that a target plane of planned cut is optimally placed within a workspace of the passive end effector interconnecting the surgical saw blade and the robot arm 20. Command enabling movement can be given by user using various modalities, e.g. foot pedal.

In some embodiments, the surgical system computer platform 900 can use two DRAs to tracking patient anatomy position: one on patient tibia and one on patient femur. The platform 900 may use standard navigated instruments for the registration and checks (e.g., a pointer similar to the one used in Globus ExcelsiusGPS system for spine surgery). Tracking markers allowing for detection of DRAs movement in reference to tracked anatomy can be used as well.

An important difficulty in knee surgery is how to plan the position of the implant in the knee and many surgeons struggle with to do it on a computer screen which is a 2D representation of 3D anatomy. The platform 900 could address this problem by using an augmented reality (AR) head-mounted display to generate an implant overlay around the actual patient knee. For example, the surgeon can be operationally displayed a virtual handle to grab and move the implant to a desired pose and adjust planned implant placement. Afterward, during surgery, the platform 900 could render the navigation through the AR head-mounted display to show surgeon what is not directly visible. Also, the progress of bone removal, e.g., depth or cut, can be displayed in real-time. Other features that may be displayed through AR can include, without limitation, gap or ligament balance along a range of joint motion, contact line on the implant along the range of joint motion, ligament tension and/or laxity through color or other graphical overlays, etc.

The surgical planning computer 910, in some embodiments, can allow planning for use of standard implants, e.g., posterior stabilized implants and cruciate retaining implants, cemented and cementless implants, revision systems for surgeries related to, for example, total or partial knee and/or hip replacement and/or trauma.

The processor 912 may graphically illustrate on the display 912 one or more cutting planes intersecting the displayed anatomical structure at the locations selected by the operator for cutting the anatomical structure. The processor 912 also determines one or more sets of angular orientations and locations where the end effector coupler 22 must be positioned so a cutting plane of the surgical saw blade will be aligned with a target plane to perform the operator defined cuts, and stores the sets of angular orientations and locations as data in a surgical plan data structure. The processor 912 uses the known range of movement of the tool attachment mechanism of the passive end effector to determine where the end effector coupler 22 attached to the robot arm 20 needs to be positioned.

The computer subsystem 820 of the surgical robot 800 receives data from the surgical plan data structure and receives information from the camera tracking system 6 indicating a present pose of an anatomical structure that is to be cut and indicating a present pose of the passive end effector and/or surgical saw tracked through DRAs. The computer subsystem 820 determines a pose of the target plane based on the surgical plan defining where the anatomical structure is to be cut and based on the pose of the anatomical structure. The computer subsystem 820 generates steering information based on comparison of the pose of the target plane and the pose of the surgical saw. The steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

As explained above, a surgical robot includes a robot base, a robot arm connected to the robot base, and at least one motor operatively connected to move the robot arm relative to the robot base. The surgical robot also includes at least one controller, e.g. the computer subsystem 820 and the motion control subsystem 840, connected to the at least one motor and configured to perform operations.

As will be explained in further detail below with regard to FIGS. 12-19, a passive end effector includes a base configured to attach to an activation assembly of the robot arm, a first mechanism, and a second mechanism. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections which may be configured to constrain movement of the tool attachment mechanism to a range of movement within a working plane. The rotatable connections may be pivot joints allowing 1 degree-of-freedom (DOF) motion, universal joints allowing 2 DOF motions, or ball joints allowing 3 DOF motions. The tool attachment mechanism is configured to connect to the surgical saw comprising a saw blade for cutting. The first and second mechanisms may be configured to constrain a cutting plane of the saw blade to be parallel to the working plane.

In some embodiments, the operations performed by the at least one controller of the surgical robot also includes controlling movement of the at least one motor based on the steering information to reposition the passive end effector so the cutting plane of the saw blade becomes aligned with the target plane and the saw blade becomes positioned the distance from the anatomical structure to be cut that is within the range of movement of the tool attachment mechanism of the passive end effector. The steering information may be displayed to guide an operator's movement of the surgical saw and/or may be used by the at least one controller to automatically move the surgical saw.

In one embodiment, the operations performed by the at least one controller of the surgical robot also includes providing the steering information to a display device for display to guide operator movement of the passive end effector so the cutting plane of the saw blade becomes aligned with the target plane and so the saw blade becomes positioned the distance from the anatomical structure, which is to be cut, that is within the range of movement of the tool attachment mechanism of the passive end effector. The display device may correspond to the display 824 (FIG. 8), the display 34 of FIG. 1, and/or a head-mounted display.

For example, the steering information may be displayed on a head-mounted display which projects images onto a see-through display screen which forms an augmented reality image that is overlaid on real-world objects viewable through the see-through display screen. The operations may display a graphical representation of the target plane with a pose overlaid on a bone and with a relative orientation there between corresponding to the surgical plan for how the bone is planned to be cut. The operations may alternatively or additionally display a graphical representation of the cutting plane of the saw blade so that an operator may more easily align the cutting plane with the planned target plane for cutting the bone. The operator may thereby visually observe and perform movements to align the cutting plane of the saw blade with the target plane so the saw blade becomes positioned at the planned pose relative to the bone and within a range of movement of the tool attachment mechanism of the passive end effector.

Figure 10:
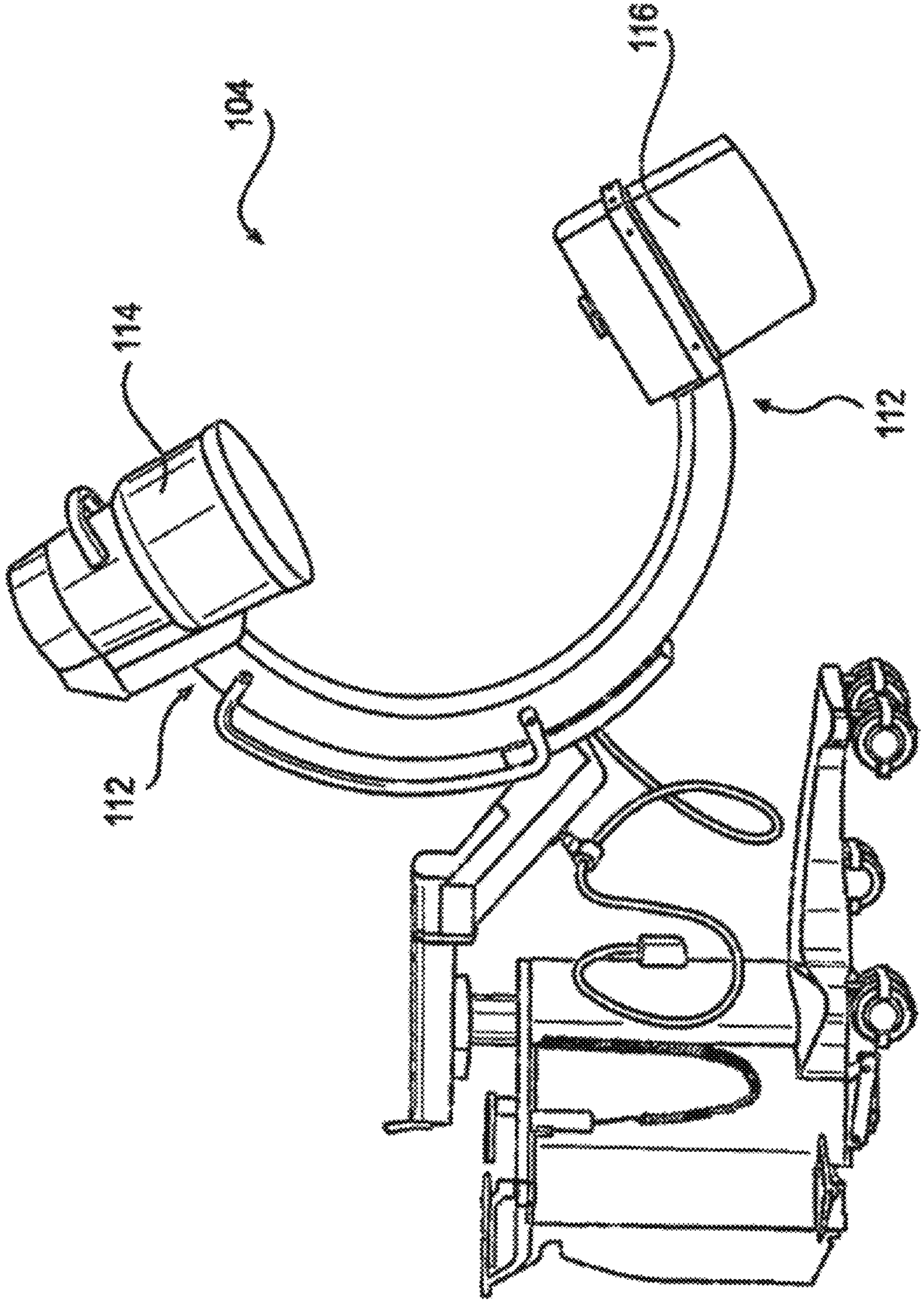
FIG. 10 illustrates an embodiment of a C-Arm imaging device that can be used in combination with the surgical robot and passive end effector in accordance with some embodiments of the present disclosure.
Figure 11:
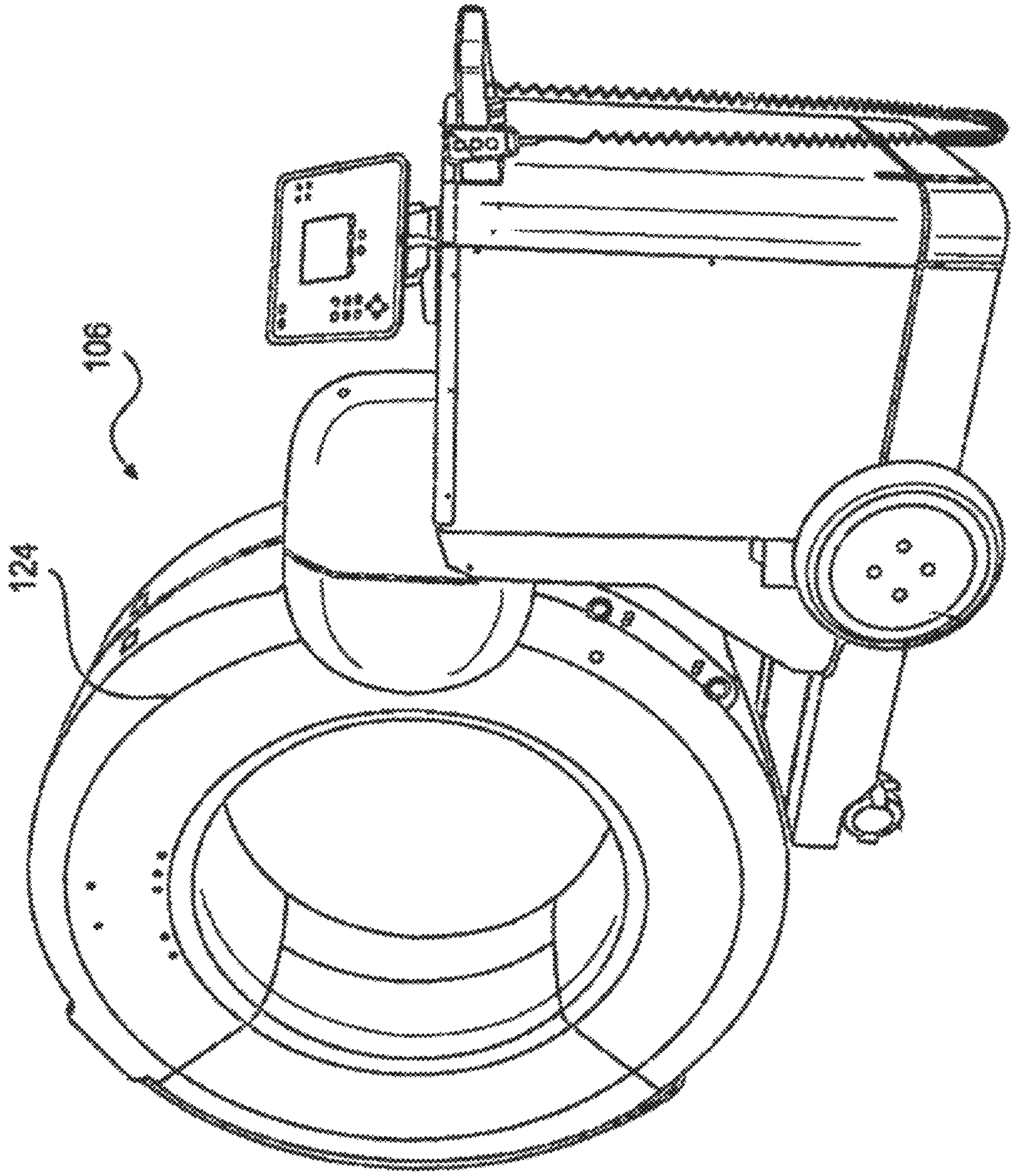
FIG. 11 illustrates an embodiment of an O-Arm imaging device that can be used in combination with the surgical robot and passive end effector in accordance with some embodiments of the present disclosure.

An automated imaging system can be used in conjunction with the surgical planning computer 910 and/or the surgical system 2 to acquire pre-operative, intra-operative, post-operative, and/or real-time image data of a patient. Example automated imaging systems are illustrated in FIGS. 10 and 11. In some embodiments, the automated imaging system is a C-arm 104 (FIG. 10) imaging device or an O-arm® 106 (FIG. 11). (O-arm® is copyrighted by Medtronic Navigation, Inc. having a place of business in Louisville, Colo., USA) It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 104 may be used as automated imaging system to scan a patient and send information to the surgical system 2.

Images captured by the automated imaging system can be displayed a display device of the surgical planning computer 910, the surgical robot 800, and/or another component of the surgical system 2.

Various embodiments of passive end effectors that are configured for use with a surgical system are now described in the context of FIGS. 12-19.

As will be explained in further detail below, the various passive end effectors illustrated in FIGS. 12-19 each include a base, a first planer mechanism, and a second planner mechanism. The base is configured to attach to an end effector coupler (e.g., end effector coupler 22 in FIGS. 4 and 5) of a robot arm (e.g., robot arm 18 in FIGS. 1 and 2) positioned by a surgical robot. Various clamping mechanisms may be used to firmly attach the base to the end effector coupler, removing backlash and ensuring suitable stiffness. Irreversible clamping mechanisms which may be used to attach the base to the end effector coupler can include but are not limited to toggle joint mechanisms or irreversible locking screw(s). A user may use an additional tool, such as but not limited to, a screwdriver, torque wrench, or driver to activate or tighten the clamping mechanism. The first mechanism extends between a rotatable connection to the base of a two and a rotatable connection to a tool attachment mechanism. The second mechanism extends between a rotatable connection to the base and a rotatable connection to the tool attachment mechanism. The first and second mechanisms pivot about the rotatable connections. The rotatable connections may be pivot joints allowing 1 degree-of-freedom (DOF) motion, universal joints allowing 2 DOF motions, or ball joints allowing 3 DOF motions. When pivot joints are used the first and second mechanisms can be configured to constrain movement of the tool attachment mechanism to a range of movement within a working plane. The tool attachment mechanism is configured to connect to a surgical saw having a saw blade that is configured to oscillate for cutting. The first and second mechanisms may be configured, e.g., via pivot joints having 1 DOF motion, to constrain a cutting plane of the saw blade to be parallel to the working plane. The tool attachment mechanism may connect to the surgical saw or saw blade through various mechanisms that can include, but are not limited to, a screw, nut and bolt, clamp, latch, tie, press fit, or magnet. A DRA can be connected to the tool attachment mechanism or the surgical saw to enable tracking of a pose of the saw blade by the camera tracking system 6 (FIG. 3).

As explained above, a surgical system (e.g., surgical system 2 in FIGS. 1 and 2) includes a surgical robot (e.g., surgical robot 4 in FIGS. 1 and 2) and a tracking system (e.g., camera tracking system 6 in FIGS. 1 and 3) that is configured to determine a pose of an anatomical structure that is to be cut by the saw blade and to determine a pose of the saw blade. The surgical robot includes a robot base, a robot arm that is rotatably connected to the robot base and configured to position the passive end effector. At least one motor is operatively connected to move the robot arm relative to the robot base. At least one controller is connected to the at least one motor and configured to perform operations that include determining a pose of a target plane based on a surgical plan defining where the anatomical structure is to be cut and based on the pose of the anatomical structure, where the surgical plan may be generated by the surgical planning computer 910 of FIG. 9 based on input from an operator, e.g., surgeon or other surgery personnel. The operations further include generating steering information based on comparison of the pose of the target plane and the pose of the surgical saw. The steering information indicates where the passive end effector needs to be moved to position the working plane of the passive end effector so the cutting plane of the saw blade is aligned with the target plane.

In some further embodiments, the operations performed by the at least one controller further include controlling movement of the at least one motor based on the steering information to reposition the passive end effector so the cutting plane of the saw blade becomes aligned with the target plane and the saw blade becomes positioned a distance from the anatomical structure to be cut that is within the range of movement of the tool attachment mechanism of the passive end effector.

The operations may include providing the steering information to a display device for display to guide operator movement of the passive end effector so the cutting plane of the saw blade becomes aligned with the target plane and so the saw blade becomes positioned a distance from the anatomical structure, which is to be cut, that is within the range of movement of the tool attachment mechanism of the passive end effector.

As explained above, some surgical systems can include head-mounted display devices that can be worn by a surgeon, nurse practitioner, and/or other persons assisting with the surgical procedure. The surgical systems can display information that allows the wearer to position the passive end effector more accurately and/or to confirm that it has been positioned accurately with the saw blade aligned with the target plane for cutting a planned location on an anatomical structure. The operation to provide the steering information to the display device, may include configuring the steering information for display on a head-mounted display device having a see-through display screen that displays the steering information as an overlay on the anatomical structure that is to be cut to guide operator movement of the passive end effector so the cutting plane of the saw blade becomes aligned with the target plane and the saw blade becomes positioned the distance from the anatomical structure within the range of movement of the tool attachment mechanism of the passive end effector.

The operation to configure the steering information for display on the head-mounted display device, may include generating a graphical representation of the target plane that is displayed as an overlay anchored to and aligned with the anatomical structure that is to be cut, and generating another graphical representation of the cutting plane of the saw blade that is displayed as an overlay anchored to and aligned with the saw blade. A wearer may thereby move the surgical saw to provide visually observed alignment between the graphically rendered target plane and the graphically rendered cutting plane.

The operation to configure the steering information for display on the head-mounted display device, may include generating a graphical representation a depth of cut made by the saw blade into a graphical representation of the anatomical structure being cut. Thus, the wearer can use the graphical representation of depth of cut to better monitor how the saw blade is cutting through bone despite direct observation of the cutting being obstructed by tissue or other structure.

The tracking system can be configured to determine the pose of the anatomical structure that is to be cut by the saw blade based on determining a pose of tracking markers, e.g., DRAs, that are attached to the anatomical structure, and can be configured to determine a pose of the surgical saw based on determining a pose of tracking markers connected to at least one of the surgical saw and the passive end effector. The tracking system can be configured to determine the pose of the surgical saw based on rotary position sensors which are configured to measure rotational positions of the first and second mechanisms during movement of the tool attachment mechanism within the working plane. As explained above, position sensors may be directly connected to at least one joint of the passive end effector structure, but may also be positioned in another location in the structure and remotely measure the joint position by interconnection of a timing belt, a wire, or any other synchronous transmission interconnection. Additionally the pose of the saw blade can be determined based on the tracking markers attached to the structure base, position sensors in the passive structure and kinematic model of the structure.

Figure 12:
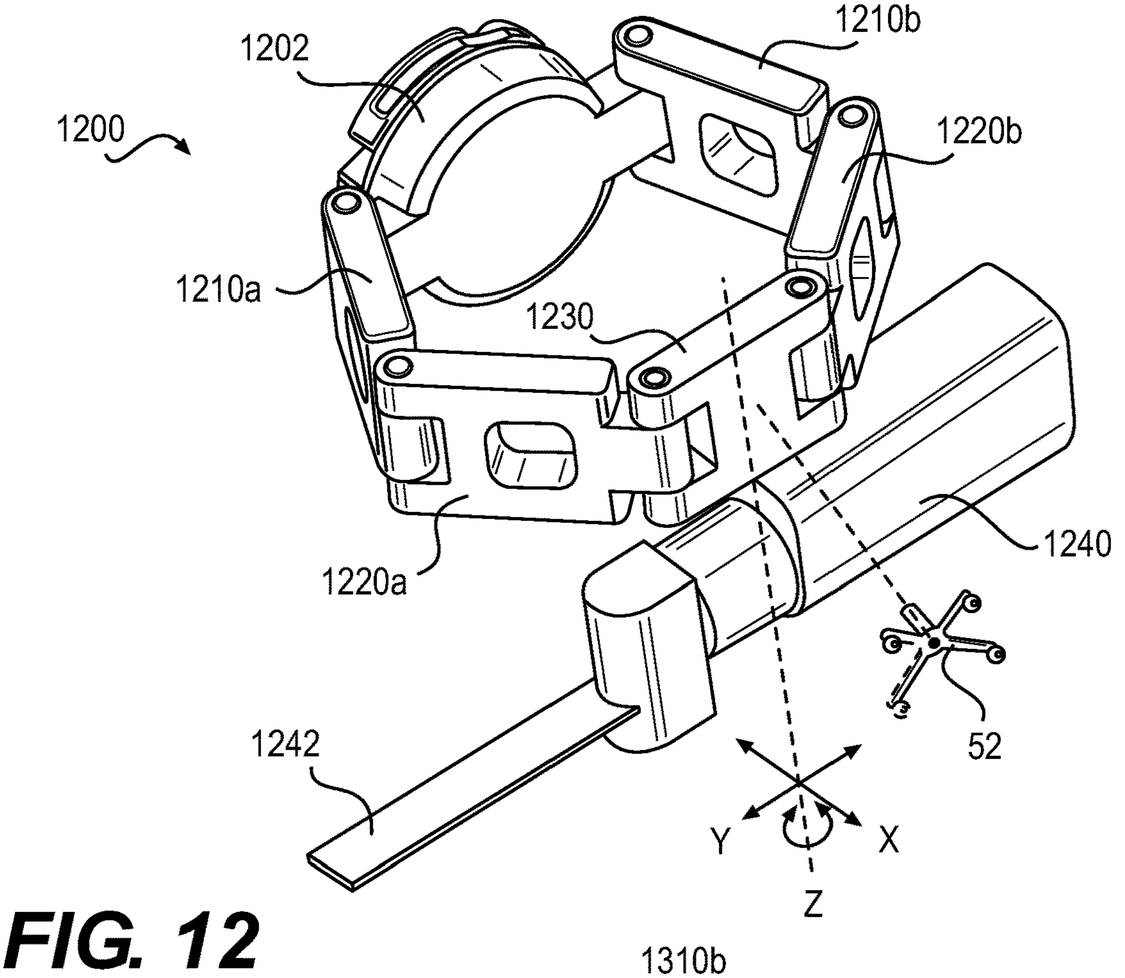
FIGS. 12-19 illustrate alternative embodiments of passive end effectors which are configured in accordance with some embodiments of the present disclosure.

The various passive end effectors disclosed herein can be sterilizable or non-sterile (covered by a sterile drape) passive 3 DOF (Degree Of Freedom) mechanical structures allowing mechanical guidance of a surgical saw or saw blade, such as a sagittal saw, along two translations in a plane parallel to the saw blade (defining the cut plane), and one rotation perpendicular to this cut plane (instrument orientation). During the surgery, the surgical robot 4 moves the end effector coupler 22, and the passive end effector and surgical saw attached there, automatically to a position close to a knee or other anatomical structure, so that all bone to be cut is within the workspace of the passive end effector. This position depends on the cut to be made and the surgery planning and implant construction. The passive end effector can have 3 DOF to guide sagittal saw or saw blade on the cutting plane providing two translation (X and Y directions) and a rotation (around Z axis) as shown in FIG. 12.

When the surgical robot 4 achieves a planned position, it holds the position (either on brakes or active motor control) and does not move during the particular bone cut. It is the passive end effector that allows movement of the saw blade of the surgical saw along the planned target plane. Such planar cuts are particularly useful for classical total knee arthroplasty where all bone cuts are planar. In partial knee arthroplasty there are special types of implants, called "onlay" which can be used in conjunction with saw-prepared bone surfaces. The various passive end effectors have mechanical structure that can ensure precision of guidance during cuts, with higher precision than classical jigs, and provide sufficient range of workspace range to cut all the bone that is planned and while provide sufficient transverse stiffness (corresponding to locked DOF) despite possibly significant amount of vibrations originating from the surgical saw in addition to forces applied by the surgeon and bone reactionary forces.

As the same time, it is preferable to measure the passive end effector position because it enables the surgical robot 4 to inform the surgeon how much bone has been removed (procedure advancement). One way to provide real-time information on bone removal is for the surgical robot 4 to measure where the saw blade passed in reference to the bone because the blade can pass only where the bone has been cut. To measure saw blade position a DRA can be mounted to the surgical saw and/or the passive end effector. This enables direct or indirect measurement of the saw position in 3D space. An alternative way to measure saw blade position is to integrate position (rotation or translation) sensors (e.g. encoders, resolvers) into position information of the passive end effector in order to calculate position of the saw blade using a mathematical model of a defined relationship between location of the passive end effector geometry and the tip of the saw blade.

In one embodiment, a conventional sagittal saw mechanism can be used with the surgical system computer platform 900 with little or no changes. The potential changes would involve adapting an external shield to enable easy attachment of the surgical saw to the passive end effector but would not necessarily involve changes in the internal mechanics. The passive end effector may be configured to connect to a conventional sagittal saw provided by, for example, DeSoutter company. In addition, the saw blade may be directly attached to the passive end effector without the saw handpiece.

To prevent the saw from unintentional passive end effector movement when the surgical robot 4 positions the passive end effector, e.g., to prevent the surgical saw from falling on the patient due to gravitational forces, the passive end effector can include a lock mechanism that moves between engaged and disengaged operations. While engaged, the lock mechanism prevents movement of the saw blade with respect to the robot end effector coupler, either directly by locking the degree of freedoms (DOFs) of the surgical saw, or indirectly by braking or locking specifics joints of the passive end effector. While disengaged, the first and second mechanisms of the passive end effector can be moved relative to the base without interference from the lock mechanism. The lock mechanism may also be used when a surgeon holds the surgical saw and controls the surgical robot 4 movement by applying forces and torques to the surgical saw. The surgical robot 4, using the load cell 64 of FIGS. 6 and 7 integrated in the distal end of the robot arm 22, measures forces and torques that are applied and generates responsive forces and torques on the robot arm 22 so the surgeon can more easily move the passive end effector back and forth, left and right, apply rotations around various axes.

A first embodiment of a passive end effector is shown in FIG. 12. Referring to FIG. 12, the passive end effector 1200 includes a base 1202 configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1200 further includes first and second mechanisms that extend between rotatable connections to the base 1202 and rotatable connections to a tool attachment mechanism. The rotatable connections may be pivot joints allowing 1 degree-of-freedom (DOF) motion, universal joints allowing 2 DOF motions, or ball joints allowing 3 DOF motions. The first and second mechanisms form a parallel architecture that positions the surgical saw rotation axis in the cut plane.

First and second link segments 1210*a* and 1220*a* form the first planer mechanism, and third and fourth link segments 1210*b* and 1220*b* form the second planner mechanism. The first link segment 1210*a* extends between a rotatable connection to a first location on the base 1202 and a rotatable connection to an end of the second link segment 1220*a*. The third link segment 1210*b* extends between a rotatable connection to a second location on the base 1202 and a rotatable connection to an end of the fourth link segment 1220*b*. The first and second locations on the base 1202 are spaced apart on opposite sides of a rotational axis of the base color to when rotated by the robot arm. The tool attachment mechanism is formed by a fifth link segment that extends between rotatable connections to distal ends of the second link segment 1220*a* and the fourth link segment 1220*b* relative to the base 1202. The first and second mechanisms (first and second link segments 1210*a*-1220*a* and third and fourth link segments 1210*b*-1220*b*) pivot about their rotatable connections to constrain movement of the tool attachment mechanism 1230 to a range of movement within a working plane. The tool attachment mechanism 1230 is configured to connect to a surgical saw 1240 having a saw blade 1242 that is configured to oscillate for cutting. The first and second mechanisms (first and second link segments 1210*a*-1220*a* and third and fourth link segments 1210*b*-1220*b*) may be configured, e.g., via pivot joints having 1 DOF motion, to constrain a cutting plane of the saw blade 1242 to be parallel to the working plane. The tool attachment mechanism 1230 may connect to the surgical saw 1240 through various mechanisms that can include, but are not limited to, a screw, nut and bolt, clamp, latch, tie, press fit, or magnet. A DRA 52 can be connected to the tool attachment mechanism 1230 or the surgical saw 1240 to enable tracking of a pose of the saw blade 1242 by the camera tracking system 6 (FIG. 3).

The passive end effector 1200 provides passive guidance of the surgical saw 1240 to constrain the saw blade 1242 to a defined cutting plane and reduce its mobility to three degrees of freedom (DOF): two translations Tx and Ty in a plane parallel to the cutting plane of the saw blade 1242; and one rotational Rz around an axis perpendicular to the cutting plane.

In some embodiments, a tracking system is configured to determine the pose of the saw blade 1242 based on rotary position sensors connected to the rotational joints of at least some of the link segments of the passive end effector 1200. The rotary position sensors are configured to measure rotational positions of the joined link segments during movement of the tool attachment mechanism within the working plane. For example, a rotary position sensor can be configured to measure rotation of the first link segment 1210*a* relative to the base 1202, another rotary position sensor can be configured to measure rotation of the second link segment 1220*a* relative to the first link segment 1210*a*, and another rotary position sensor can be configured to measure rotation of the tool attachment mechanism 1230 relative to the second link segment 1220*a*. The surgical saw 1240 can connected to have a fixed orientation relative to the tool attachment mechanism 1230. A serial kinematic chain of the passive end effector 1200 connecting the saw blade 1242 and the robot arm 22, having serialized link segments and pivoting joints, provides the required mobility to the surgical saw 1240. The position of the tip of the saw blade 1242 in the plane defined by the passive kinematic chain can be fully determined by the joint angles, sensed through the rotary position sensors, and the structural geometry of the interconnected link segments. Therefore, by measuring the relative angle between each connected link segment, for example along one or more interconnected paths between the base 1202 and the surgical saw 1240, the position of the tip of the saw blade 1242 in the cut space can be computed using the proposed forward kinematic model. When the position and orientation of robot arm 22 distal end position and orientation with respect to the bone is known, the position and orientation of the saw blade 1242 with respect to the bone can be computed and displayed as feedback to the surgeon. For exemplary implementations where the saw blade is directly attached to the passive end effector, the frequency of measurement provided by rotary position sensors may be at least two times higher than saw blade oscillation frequency in order to measure saw blade position even during oscillations.

Example types of rotary position sensors that can be used with passive end effectors herein can include, but are not limited to: potentiometers; optical; capacitive; rotary variable differential transformer (RVDT); linear variable differential transformer (LVDT); Hall effect; and incoder.

A potentiometer based sensor is a passive electronic component. Potentiometers work by varying the position of a sliding contact across a uniform resistance. In a potentiometer, the entire input voltage is applied across the whole length of the resistor, and the output voltage is the voltage drop between the fixed and sliding contact. To receive and absolute position, a calibration-position is needed. Potentiometers may have a measurement range smaller 360°.

An optical encoder can include a rotating disk, a light source, and a photo detector (light sensor). The disk, which is mounted on the rotating shaft, has patterns of opaque and transparent sectors coded into the disk. As the disk rotates, these patterns interrupt the light emitted onto the photo detector, generating a digital or pulse signal output. Through signal encoding on the disk absolute and relative as well as multi-turn measurements are possible.

A capacitive encoder detects changes in capacitance using a high-frequency reference signal. This is accomplished with the three main parts: a stationary transmitter, a rotor, and a stationary receiver. Capacitive encoders can also be provided in a two-part configuration, with a rotor and a combined transmitter/receiver. The rotor can be etched with a sinusoidal pattern, and as it rotates, this pattern modulates the high-frequency signal of the transmitter in a predictable way. The encoder can be multi-turn, but absolute measurement is difficult to realize. Calibration at startup is needed.

RVDT and LVDT sensors operate where the core of the transformer is in null position, the output voltages of the two, primary and secondary, windings are equal in magnitude, however opposite in direction. The overall output of the null position is always zero. An angular displacement from the null position is inducing a total differential output voltage. Therefore, the total angular displacement is directly proportional to the linear differential output voltage. The differential output voltages increase with clockwise and decrease with anti-clockwise direction. This encoder works in absolute measurement and may not be multi-turn compatible. Calibration during assembly is needed.

In a Hall effect sensors, a thin strip of metal has a current applied along it. In the presence of a magnetic field, the electrons in the metal strip are deflected toward one edge, producing a voltage gradient across the short side of the strip, i.e., perpendicular to the feed current. In its simplest form, the sensor operates as an analog transducer, directly returning a voltage. With a known magnetic field, its distance from the Hall plate can be determined. Using groups of sensors, the relative position of the magnet can be deduced. By combining multiple sensor elements with a patterned magnet-plate, position can be detected absolute and relative similar to optical encoders.

An incoder sensor works in a similar way to rotary variable transformer sensor, brushless resolvers or synchros. The stator receives DC power and produces a low power AC electromagnetic field between the stator and rotor. This field is modified by the rotor depending on its angle. The stator senses the resulting field and outputs the rotation angle as an analogue or digital signal. Unlike resolvers, incoders use laminar circuits rather than wound wire spools. This technology enables incoders compact form, low mass, low inertia and high accuracy without high precision installation. A signal (Z) to count one full rotation is transmitted. Multi-turn and absolute sensing is possible.

Figure 13:
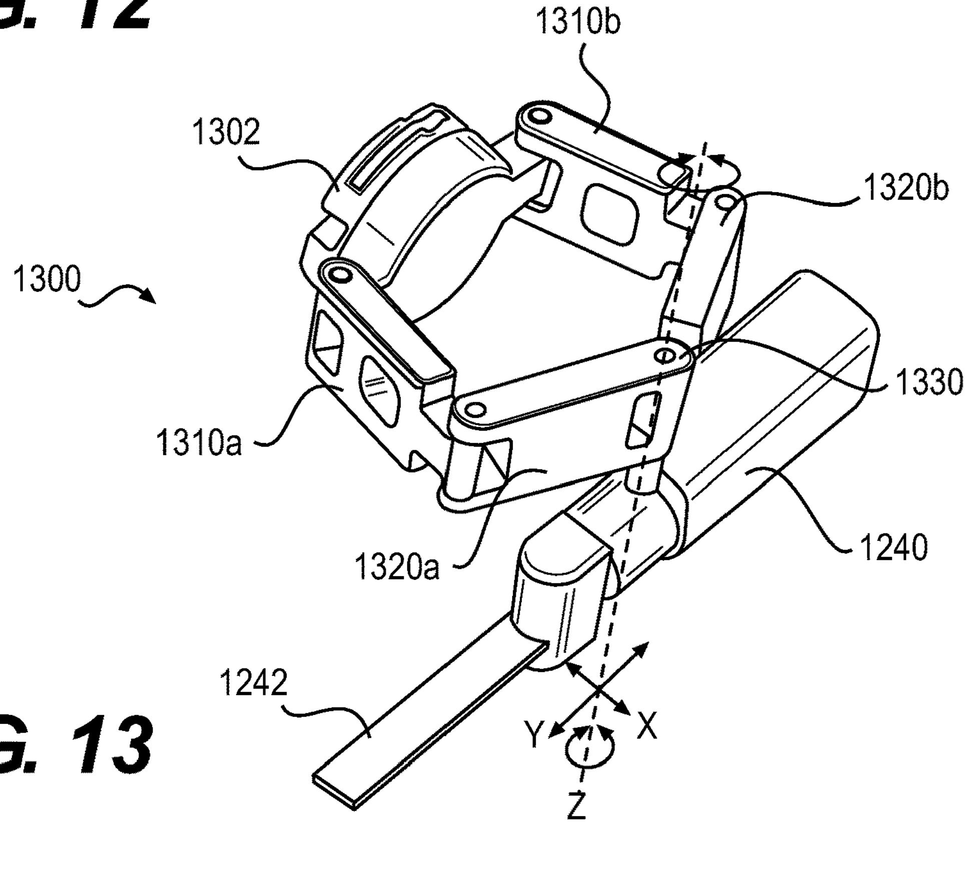

A second embodiment of a passive end effector is shown in FIG. 13. Referring to FIG. 13, the passive end effector 1300 includes a base 1302 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1300 further includes first and second mechanisms that extend between rotatable connections to the base 1302 and rotatable connections to a tool attachment mechanism. The rotatable connections may be pivot joints allowing 1 DOF motion, universal joints allowing 2 DOF motions, or ball joints allowing 3 DOF motions. First and second link segments **1310*a* and 1320*a* form the first planer mechanism, and third and fourth link segments 1310*b* and 1320*b* form the second planner mechanism. The first link segment 1310*a* extends between a rotatable connection to a first location on the base 1302 and a rotatable connection to an end of the second link segment 1320*a*. The third link segment 1310*b* extends between a rotatable connection to a second location on the base 1302 and a rotatable connection to an end of the fourth link segment 1320*b*. The first and second locations on the base 1302 are spaced apart on opposite sides of a rotational axis of the base color to when rotated by the robot arm. Distal ends of the second link segment 1320*a* and the fourth link segment 1320*b* from the base 1302 are rotatably connected to each other and to the tool attachment mechanism 1330. The first and second mechanisms (first and second link segments 1310*a*-1320*a* and third and fourth link segments 1310*b*-1320*b*) may be configured, e.g., via pivot joints having 1 DOF motion, to rotate about their rotatable connections to constrain movement of the tool attachment mechanism 1330 to a range of movement within a working plane. The tool attachment mechanism 1330 is configured to connect to a surgical saw 1240 having a saw blade 1242 that is configured to oscillate for cutting. The first and second mechanisms (first and second link segments 1310*a*-1320*a* and third and fourth link segments 1310*b*-1320*b*) constrain a cutting plane of the saw blade 1242 to be parallel to the working plane. The tool attachment mechanism 1330 may connect to the surgical saw 1240 through various mechanisms that can include, but are not limited to, a screw, nut and bolt, clamp, latch, tie, press fit, or magnet. A DRA can be connected to the tool attachment mechanism 1330 or the surgical saw 1240 to enable tracking of a pose of the saw blade 1242 by the camera tracking system 6 (FIG. 3**).

Figure 14:
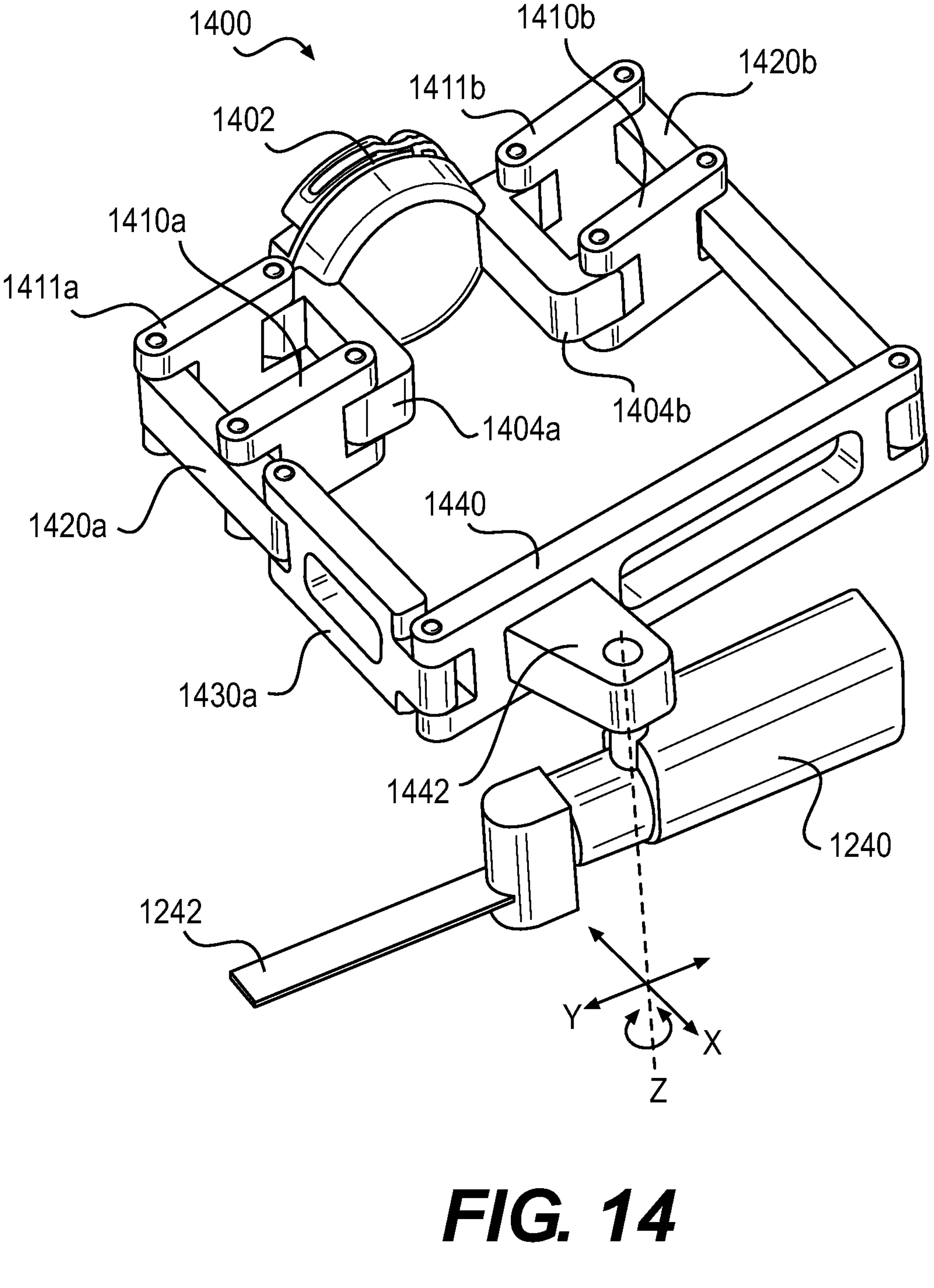

A third embodiment of a passive end effector is shown in FIG. 14. Referring to FIG. 14, the passive end effector 1400 includes a base 1402 that is configured to attach to an end effector coupler (e.g., end effector coupler 22 in FIGS. 4 and 5) of a robot arm (e.g., robot arm 18 in FIGS. 1 and 2) positioned by a surgical robot. The base 1402 includes first and second elongated base segments **1404*a* and 1404*b* that extend from spaced apart locations on opposite sides of a rotational axis of the base 1402 when rotated by the robot arm. The first and second elongated base segments 1404*a* and 1404*b* extend in a direction away from the end effector coupler of the robot arm when attached to the passive end effector 1400. The passive end effector 1400 further includes first and second mechanisms that extend between rotatable connections to the elongated base segments 1404***a* and 1404*b* and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions.

The first mechanism includes a first link segment 1411*a*, the second link segment 1410*a*, a third link segment 1420*a*, and a fourth link segment 1430*a*. The first and second link segments 1411*a* and 1410*a* extend parallel to each other between rotatable connections to spaced apart locations on the first elongated base segment 1404*a* and spaced apart locations on the third link segment 1420*a*. An end of the third link segment 1420*a* is rotatably connected to an end of the fourth link segment 1430*a*.

The second mechanism includes a fifth link segment 1411*b*, a sixth link segment 1410*b*, and a seventh link segment 1420*b*. The fifth and sixth link segments 1411*b* and 1410*b* extend parallel to each other between rotatable connections to spaced apart locations on the second elongated base segment 1404*b* and spaced apart locations on the seventh link segment 1420*b*. The tool attachment mechanism includes an eighth link segment 1440 that extends between rotatable connections to distal ends of the fourth and seventh link segments 1430*a* and 1420*b* from the base 1402. In a further embodiment, the eighth link segment 1440 of the tool attachment mechanism includes an attachment member 1442 that extends in a direction away from the base 1402 to a rotatable connector that is configured to connect to the surgical saw 1240. The attachment member 1442 extends from a location on the eighth link segment 1440 that is closer to the fourth link segment 1430*a* than to the seventh link segment 1420*b*.

The first and second mechanisms (set of link segments 1411*a*, 1410*a*, 1420*a*, 1430*a* and set of link segments 1411*b*, 1410*b*, 1420*b*) may be configured to pivot about their rotatable connections to constrain movement of the tool attachment mechanism 1440 to a range of movement within a working plane. The tool attachment mechanism 1440 is configured to connect to the surgical saw 1240 having the saw blade 1242 that is configured to oscillate for cutting. The first and second mechanisms may be configured, e.g., via pivot joints having 1 DOF motion, to constrain a cutting plane of the saw blade 1242 to be parallel to the working plane. The tool attachment mechanism 1440 may connect to the surgical saw 1240 through various mechanisms that can include, but are not limited to, a screw, nut and bolt, clamp, latch, tie, press fit, or magnet. A DRA can be connected to the tool attachment mechanism 1440, such as to the attachment member 1442, or the surgical saw 1240 to enable tracking of a pose of the saw blade 1242 by the camera tracking system 6 (FIG. 3).

The passive end effector 1400 of FIG. 14 has a parallel architecture enabling positioning of the surgical saw about a rotation axis in the cut plane. Synchronized and/or different motion of lateral parallelograms allow positioning of the surgical saw rotation axis in the cut plane.

Figure 15:
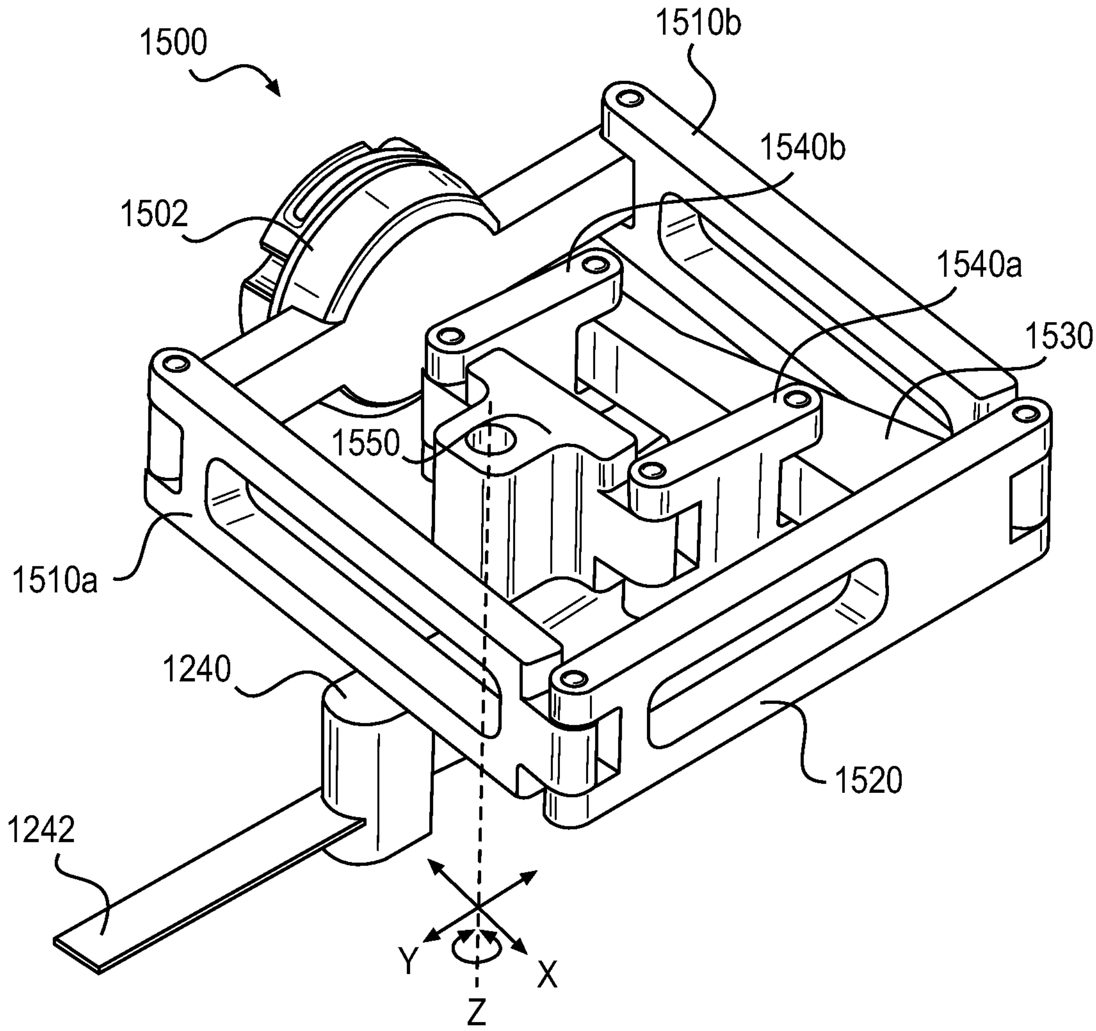

A fourth embodiment of a passive end effector is shown in FIG. 15. The passive end effector 1500 includes a base 1502 that is configured to attach to an end effector coupler (e.g., end effector coupler 22 in FIGS. 4 and 5) of a robot arm (e.g., robot arm 18 in FIGS. 1 and 2) positioned by a surgical robot. The base 1502 may include first and second elongated base segments that extend from spaced apart locations on opposite sides of a rotational axis of the base 1502 when rotated by the robot arm. The first and second elongated base segments extend away from each other. The passive end effector 1500 further includes first and second mechanisms that extend between rotatable connections to the base 1502 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions.

The first mechanism includes a first link segment 1510*a*. The second mechanism includes a second segment 1510*b*. The tool attachment mechanism includes a third link segment 1520, a fourth link segment 1530, a fifth link segment 1540*a*, a sixth link segment 1540*b*, and a seventh link segment 1550. The first and second link segments 1510*a* and 1510*b* extend between rotatable connections to first and second locations, respectively, on the base 1502, e.g., to first and second elongated base segments extending away from the base 1502, to rotatable connections at opposite ends of the third link segment 1520. The first and second locations on the base 1502 are spaced apart on opposite sides of a rotational axis of the base when rotated by the robot arm. The fourth link segment 1530 extends from the third link segment 1520 in a direction towards the base 1502. The fifth and sixth link segments 1540*a* and 1540*b* extend parallel to each other between rotatable connections to spaced apart locations on the fourth link segment 1530 and spaced apart locations on the seventh link segment 1550. The seventh link segment 1550 is configured to have a rotatable connector that is configured to connect to the surgical saw 1240.

The first through sixth link segments 1510*a-b*, 1520, 1530, and 1540*a-b* may be configured to pivot about their rotatable connections to constrain movement of the seventh link segment 1550 to a range of movement within a working plane. The seventh link segment 1550 is configured to connect to the surgical saw 1240 having the saw blade 1242 that is configured to oscillate for cutting. The first through sixth link segments 1510*a-b*, 1520, 1530, and 1540*a-b* may be configured to constrain a cutting plane of the saw blade 1242 to be parallel to the working plane, e.g., via pivot joints having 1 DOF motion. The seventh link segment 1550 may connect to the surgical saw 1240 through various mechanisms that can include, but are not limited to, a screw, nut and bolt, clamp, latch, tie, press fit, or magnet. A DRA can be connected to the seventh link segment 1550 or the surgical saw 1240 to enable tracking of a pose of the saw blade 1242 by the camera tracking system 6 (FIG. 3).

Figure 16:
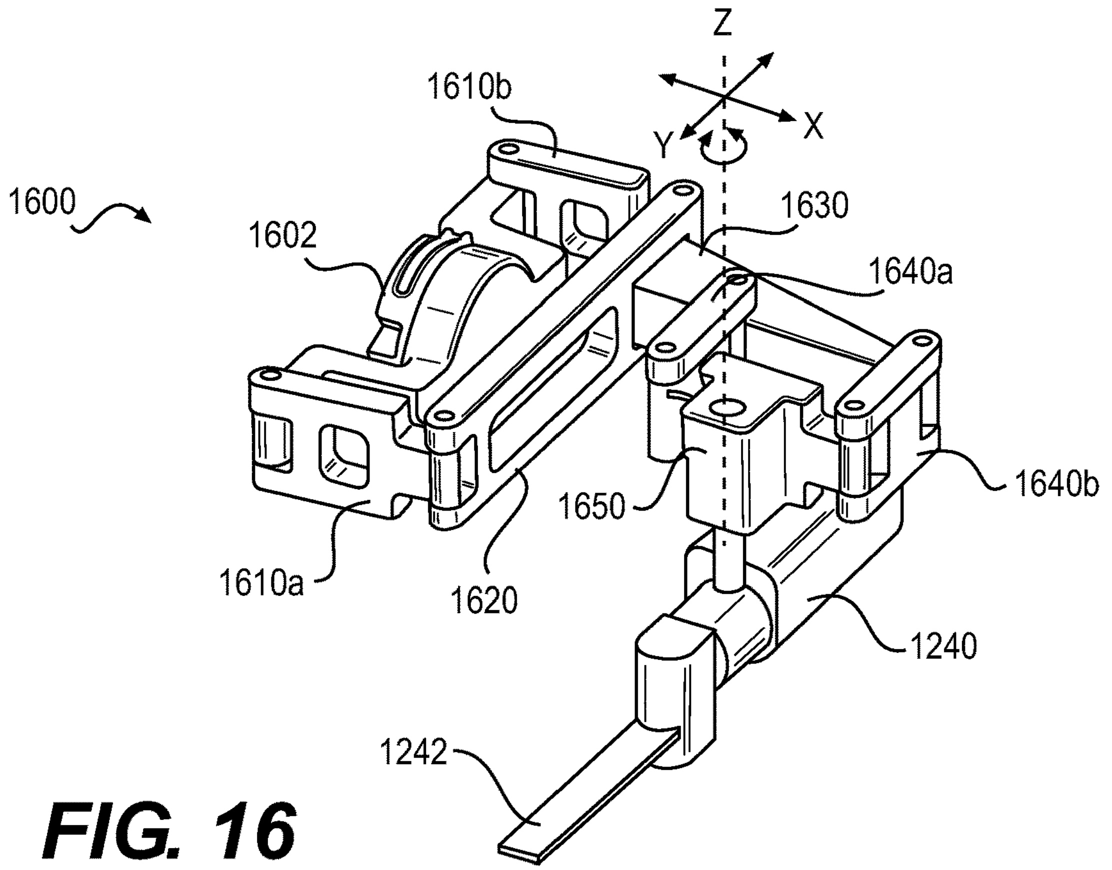

A fifth embodiment of a passive end effector is shown in FIG. 16. The passive end effector 1600 includes a base 1602 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1600 further includes first and second mechanisms that extend between rotatable connections to the base 1502 and rotatable connections to a tool attachment mechanism. The first mechanism includes a first link segment 1610*a*. The second mechanism includes a second segment 1610*b*. The tool attachment mechanism includes a third link segment 1620, a fourth link segment 1630, a fifth link segment 1640*a*, a sixth link segment 1640*b*, and a seventh link segment 1650. One or more of the rotatable connections disclosed for this embodiment may be pivot joints allowing 1 DOF motion, universal joints allowing 2 DOF motions, or ball joints allowing 3 DOF motions.

The first and second link segments 1610*a* and 1610*b* extend between rotatable connections to first and second locations, respectively, on the base 1602 to rotatable connections at opposite ends of the third link segment 1620. The first and second locations on the base 1602 are spaced apart on opposite sides of a rotational axis of the base 1602 when rotated by the robot arm. The fourth link segment 1630 extends from the third link segment 1620 in a direction away from the base 1602. The fifth and sixth link segments 1640*a* and 1640*b* extend parallel to each other between rotatable connections to spaced apart locations on the fourth link segment 1630 and spaced apart locations on the seventh link segment 1650. The seventh link segment 1650 is configured to have a rotatable connector that is configured to connect to the surgical saw 1240.

The first through sixth link segments 1610*a-b*, 1620, 1630, and 1640*a-b* may be configured to pivot about their rotatable connections to constrain movement of the seventh link segment 1650 to a range of movement within a working plane. The seventh link segment 1650 is configured to connect to the surgical saw 1240 having the saw blade 1242 that is configured to oscillate for cutting. The first through sixth link segments 1610*a-b*, 1620, 1630, and 1640*a-b* may be configured to pivot while constraining a cutting plane of the saw blade 1242 to be parallel to the working plane. The seventh link segment 1650 may connect to the surgical saw 1240 through various mechanisms that can include, but are not limited to, a screw, nut and bolt, clamp, latch, tie, press fit, or magnet. A DRA can be connected to the seventh link segment 1650 or the surgical saw 1240 to enable tracking of a pose of the saw blade 1242 by the camera tracking system 6 (FIG. 3).

The passive end effector 1600 provides two perpendicular translational movements for positioning the surgical saw rotation axis in the cutting plane, and where the two translations are implemented by parallelograms.

Figure 17:
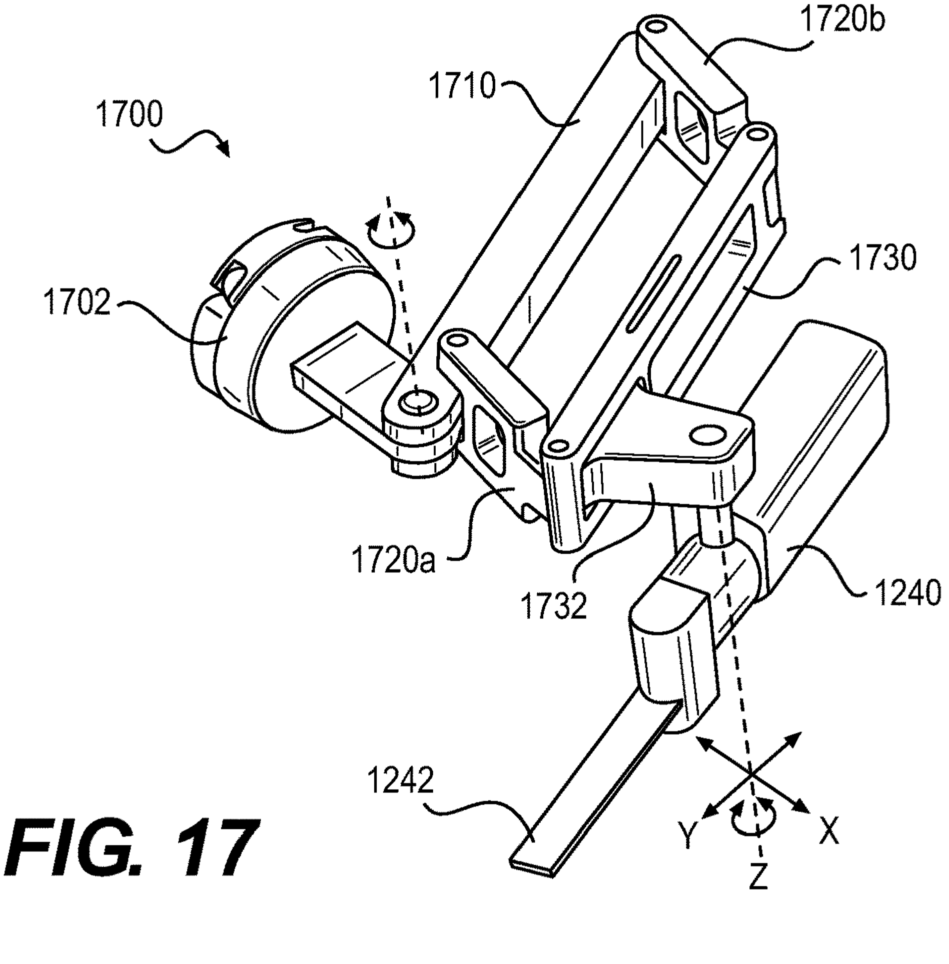

A sixth embodiment of a passive end effector is shown in FIG. 17. The passive end effector 1700 includes a base 1702 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1700 further includes first and second mechanisms that extend between rotatable connections to the base 1702 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions. The first and second mechanisms are connected to provide translation along the radius of a parallelogram. The first mechanism includes first and second link segments 1710 and 1720*b*. The first link segment 1710 extends between a rotatable connection to the base 1702 and a rotatable connection to an end of the second link segment 1720*b*. The second mechanism includes a third link segment 1720*a*. The tool attachment mechanism includes a fourth link segment 1730. The second and third link segments 1720*b* and 1720*a* extend away from the base 1702 and parallel to each other between rotatable connections to spaced apart locations on the first link segment 1710 and spaced apart locations on the fourth link segment 1730. The fourth link segment 1730 comprises an attachment member 1732 that extends in a direction away from the base to a rotatable connector that is configured to connect to the surgical saw 1240. The attachment member 1732 extends from a location on the fourth link segment 1730 that is closer to the third link segment 1720*a* than to the second link segment 1720*b*.

The first through third link segments 1710, 1720*b*, 1720*a* may be configured to pivot about their rotatable connections to constrain movement of the fourth link segment 1730 to a range of movement within a working plane. The fourth link segment 1730 is configured to connect to the surgical saw 1240 having the saw blade 1242 that is configured to oscillate for cutting. The first through third link segments 1710, 1720*b*, 1720*a* pivot and may be configured to constrain a cutting plane of the saw blade 1242 to be parallel to the working plane. The fourth link segment 1730, e.g., the attachment member 1732 thereof, may connect to the surgical saw 1240 through various mechanisms that can include, but are not limited to, a screw, nut and bolt, clamp, latch, tie, press fit, or magnet. A DRA can be connected to the fourth link segment 1730, e.g., to the attachment member 1732, or the surgical saw 1240 to enable tracking of a pose of the saw blade 1242 by the camera tracking system 6 (FIG. 3).

Figure 18:
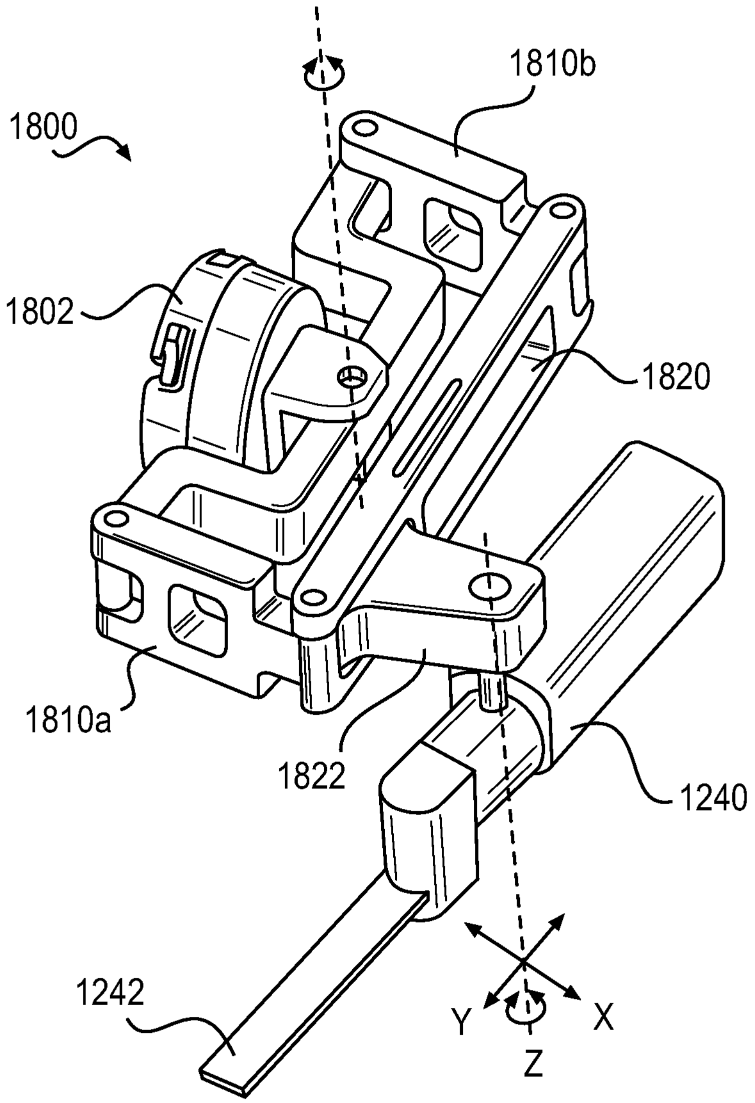

A seventh embodiment of a passive end effector is shown in FIG. 18. The passive end effector 1800 includes a base 1802 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1800 further includes first and second mechanisms that extend between rotatable connections to the base 1802 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions. The first mechanism includes a first link segment 1810*a*. The second mechanism includes a second link segment 1810*b*. The tool attachment mechanism includes a third link segment 1820. The first and second link segments 1810*a* and 1810*b* extend between rotatable connections to first and second locations, respectively, on the base 1802 to rotatable connections at opposite ends of the third link segment 1820. The first and second locations on the base 1802 are spaced apart on opposite sides of a rotational axis of the base 1802 when rotated by the robot arm. The third link segment 1820 includes an attachment member 1822 that extends in a direction away from the base 1802 to a rotatable connector that is configured to connect to the surgical saw 1240. The attachment member 1822 extends from a location on the third link segment 1820 that is closer to the first link segment 1810*a* than to the second link segment 1810*b*. One or more of the rotatable connections disclosed for this embodiment may be pivot joints allowing 1 DOF motion, universal joints allowing 2 DOF motions, or ball joints allowing 3 DOF motions.

The first and second link segments 1810*a* and 1810*b* may be configured to pivot about their rotatable connections between the base 1802 and the third link segment 1820 to constrain movement of the attachment member 1822 to a range of movement within a working plane. In some other embodiments one or more of the rotatable connections can be universal joints allowing 2 DOF motions or ball joints allowing 3 DOF motions such that the movement is not constrained to the working plane. The attachment member 1822 is configured to connect to the surgical saw 1240 having the saw blade 1242 that is configured to oscillate for cutting. The first and second link segments 1810*a* and 1810*b* pivot while constraining a cutting plane of the saw blade 1242 to be parallel to the working plane. The attachment member 1822 may connect to the surgical saw 1240 through various mechanisms that can include, but are not limited to, a screw, nut and bolt, clamp, latch, tie, press fit, or magnet. A DRA can be connected to the third link segment 1820, e.g., to the attachment member 1822, or the surgical saw 1240 to enable tracking of a pose of the saw blade 1242 by the camera tracking system 6 (FIG. 3).

Figure 19:
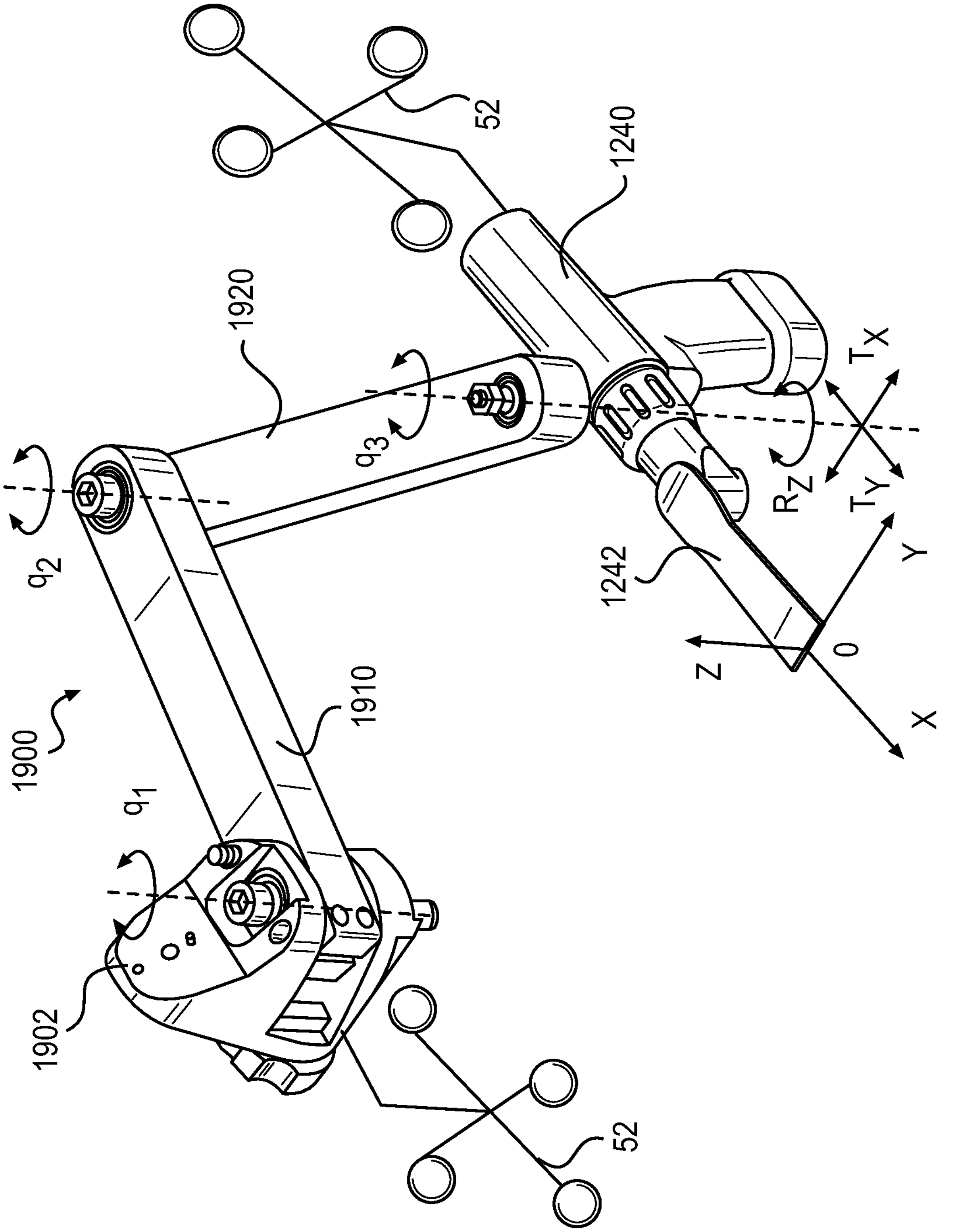

An eighth embodiment of a passive end effector is shown in FIG. 19. The passive end effector 1900 includes a base 1902 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1900 further includes a first link segment 1910 and a second link segment 1920. The first link segment 1910 extends between a rotatable connection to the base 1902 and a rotatable connection to one end of the second link segment 1920. Another end of the second link segment 1920 is rotatably connected to a tool attachment mechanism. The rotational axes q1, q2 and q3 are parallel to each other so as to provide a planar cutting plane for the blade 1242. Thus, the 3 DOF motion of the saw 1240 includes x-direction Tx, y-direction Ty and rotational direction about z-axis Rz. One or more of the rotatable connections disclosed for this embodiment may be pivot joints allowing 1 DOF motion, universal joints allowing 2 DOF motions, or ball joints allowing 3 DOF motions.

The tracking markers 52 attached to the end effector base 1902 and the saw 1240 along with the tracking markers on the bones (e.g., tibia and femur) can be used to precisely and continuously monitor the real-time location of the blade 1242 and blade tip relative to the patient bone being cut. Although not explicitly shown in other figures, the tracking markers can be attached to the saw 1240 and all end effectors 1902 in all embodiments to track the location of the blade relative to the patient bone being cut. Although not shown, alternatively or in addition to the tracking markers, encoders can be positioned in each of the link segments 1910 and 1920 to determine precisely where the saw blade tip is at all times.

Example Surgical Procedure

An example surgical procedure using the surgical robot 4 in an Operating Room (OR) can include:

Optional step: surgery is pre-operatively planned based on medical images

1. The surgical robot 4 system is outside the Operating Room (OR). The nurse brings the system to the OR when patient is being prepared for the surgery.
2. The nurse powers on the robot and deploys the robot arm. Nurse verifies precision of robotic and tracking systems.
3. In the case of a sterilized passive end effector, the scrub nurse puts a sterile drape on the robot arm and mounts the passive end effector with the sagittal saw on the robot arm. The scrub nurse locks the passive end effector with a lock mechanism. Scrub nurse attached DRAs to passive structure through the drape (if necessary). For a non-sterilized passive end effector, the drape is placed after attachment of the passive end effector on the robot arm, the DRAs are attached to the passive end effector with the drape intervening therebetween, and a sterile saw or saw blade is attached to the passive end effector with the drape intervening therebetween. The lock mechanism is engaged, in order to fix position of the saw blade with respect to the end effector coupler.
4. The surgeon attaches navigation markers to the patient's bone(s), e.g., tibia and femur. The bones are registered with the camera tracking system 6 using, e.g., Horn point-to-point algorithm, surface matching or other algorithms. A soft-tissue balance assessment may be performed, whereby the system allows surgeon to assess balance of soft tissue in the operating room, e.g., by tracking relative movement of femur and tibia when surgeon applies forces in different directions (e.g. varus/valgus stress). Soft-tissue balance information can be used to alter surgical plan (e.g. move implant parts, change implant type etc.).
5. When surgeon is ready to cut the bone, the scrub nurse brings the surgical robot 4 to the operating table close to the knee to be operated and stabilizes the surgical robot 4 on the floor. The system may operate to guide nurse in finding robot 4 position so that all cut planes are in robot and passive structure workspace.
6. The surgeon selects on the screen of the surgical robot 4 the different parameters according to the planning of the surgery to do the first cut (bone to be cut, cutting plan desired, etc.).
7. The surgical robot 4 automatically moves the robot arm 22 to reposition the passive end effector so the cutting plane of the saw blade becomes aligned with the target plane and the saw blade becomes positioned a distance from the anatomical structure to be cut that is within the range of movement of the tool attachment mechanism of the passive end effector.
8. The surgeon unlocks the passive end effector.
9. The surgeon performs the cut constrained to the cutting plane provide by the passive end effector. The surgical robot 4 may provide real-time display of the tracked location of the saw blade relative to bone so the surgeon can monitor progress of bone removal. In one way, the tracking subsystem processes in real-time the location of the saw relative to the bone based on camera images and various tracking markers attached to the saw, robot arm, end effector, femur and tibia. The surgeon can then lock the passive end effector using the lock mechanism upon completion of the cut.
10. The surgeon selects on the screen the next cut to be executed and proceeds as before.
11. The surgeon may perform a trial implant placement and intermediate soft-tissue balance assessment and based thereon may change the implant plan and associated cuts.
12. Following completion of all cuts, the nurse removes the surgical robot 4 from the operating table and unmounts the passive end effector from the robot arm.
13. The surgeon places the implants and finishes the surgery.

In step 9 above, a physician may have a difficult time to visually confirm the progress of the cut due to tissue and ligaments around the bone and debris being created from the cut, and other surgical instruments near the bone. Even if the visual confirmation may be acceptable, there are areas of the bone the physician cannot see such as the posterior portion of the bone being cut.

Advantageously, one robotic system embodiment of the present invention provides a way for the physician to confirm the progress of the bone being cut in multiple dimensions. The camera tracking system 6 along with the tracking markers attached to the end effector base (1100, 1202, 1302, 1402, 1502, 1602, 1702, 1802, 1902), robotic arm 20 and saw (1140, 1240) allows the tracking subsystem 830 and the computer subsystem 820 to calculate in real-time the precise position of the saw blade relative to bone so the surgeon can monitor progress of bone removal.

Figure 20:
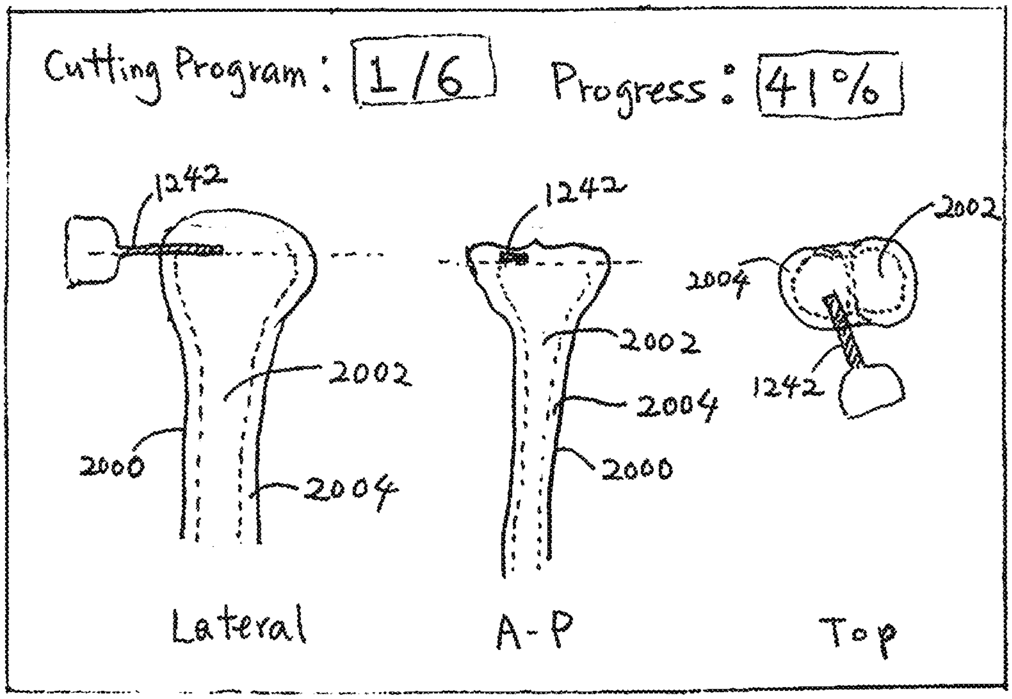
FIG. 20 is a screenshot of a display showing the progress of bone cuts during a surgical procedure.
Figure 21:
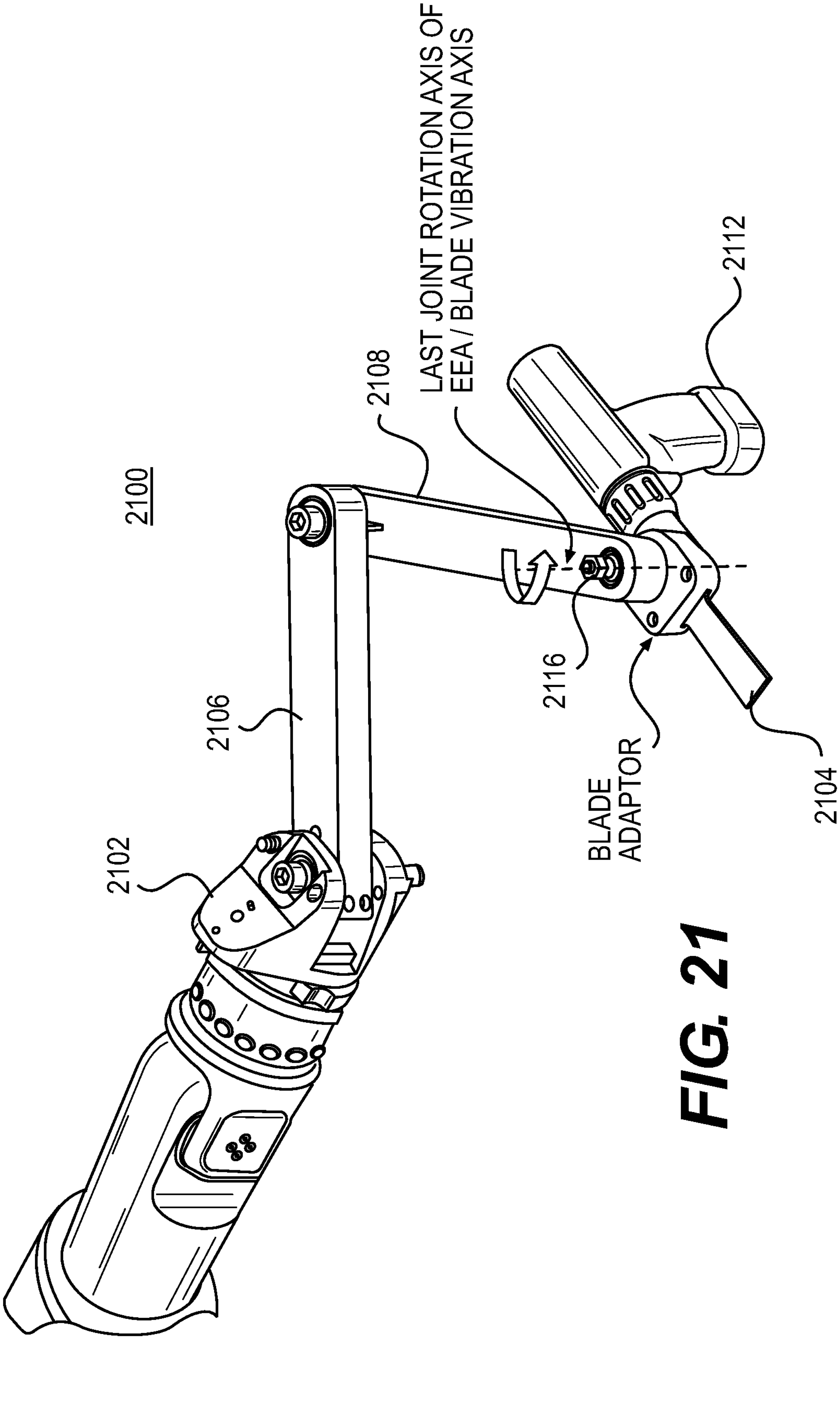
FIG. 21 illustrates an exemplary embodiment of a direct blade guidance system consistent with the principles of the present disclosure.

FIG. 20 is a screenshot of a display showing the progress of bone cuts during a surgical procedure. FIG. 20 shows the subsystems 830 and 820 displaying three images: lateral, A-P and top views. In each image, the real-time location of the saw blade 1242 relative to the bone (e.g., tibia 2000) is displayed on the display 34. The lateral and top views can be especially useful for the physician as they display the saw blade position which cannot be easily seen. At the top portion of the display, the computer subsystem 830, 820 displays the number of cutting programs and what program it is currently running. For example as the screenshot shows, the physician may have programmed 6 planar cuts and the current cutting program is the first one. Also, because the subsystems 830 and 820 can track with tracking markers where the blade may have travelled, it can determine how much of the bone cutting (area that was cut) for a particular cutting program has been completed and the percentage of progress is displayed in the display 34. The bone image itself is preferably derived from actual images of the patient's body for a more accurate representation. The bone image is augmented by the subsystem 820 with a contour line that shows the cortical bone 2004 and spongy bone 2002. This can be important for a physician as the amount of resistance to cutting varies greatly between the two types of bones.

If an augmented reality (AR) head-mounted display is used, the computer subsystem 820 can generate the same contour line showing the cortical and spongy bones and superimpose it over the actual leg continuously as the physician moves his/her head. The area that has been already cut can be overlaid over the actual bone in a dark shade. Moreover, the implant to be inserted over the cut area can also be overlaid on the bone to show the physician that the cutting is being done correctly along the plane of the implant. This is all possible because the subsystems 830 and 820 can track the position of the blade and history of its movement relative to the bone with the tracking markers and the camera subsystem.

Referring now to FIGS. 21-32, an exemplary embodiment of a direct blade guidance system in the context of orthopedic surgery is described. As shown in FIGS. 21, 22, 29, and 30 a direct blade guidance system 2100 may include a robotic system holding an end effector arm (EEA) 2102. EEA 2102 may include a base configured to attach to an end effector coupler of a robot arm. Other exemplary embodiments of an end effector arm consistent with the principles of this disclosure are described with regard to FIGS. 12-19. In order to achieve planar cuts, a saw blade 2104 should be guided in the plane in which it vibrates. Saw blade high vibration frequency (e.g. 200-300 Hz) makes it difficult to realize mechanical guidance. EEA 2102 may include several joints and linkages 2106, 2108 that may be used to realize movement on the plane of a tip 2110 of EEA 2102. Similar to embodiments of FIGS. 12-18, tip 2110 of EEA 2102 may have three (3) degrees of freedom: movement in two directions on the plane and rotation around the axis normal to that plane. EEA 2102 may allow planar cuts and approach the target bone from all angles. System 2100 may also include a handpiece 2112 and a blade adaptor 2114 each connected to EEA 2102 and blade 2104.

The concept of directly guiding saw blade 2104 includes aligning the rotation axis of a distal end of linkage 2110 (distal rotational joint 2116 of EEA 2102) with a blade vibration axis. Sagittal saws are in the majority of implementation mechanisms which generate small rotational movement of the saw blade (vibration/oscillation) around an axis close to the saw blade attachment. By aligning the rotation axis with the distal rotational joint 2116 of EEA 2102 (at a distal end of linkage 2108), joint 2116 may be configured to enable general saw handpiece rotation and enable saw blade vibration.

Figure 31:
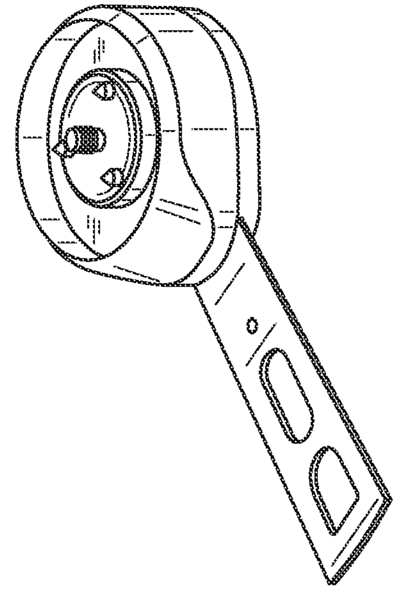
FIG. 31 illustrates an exemplary embodiment of a blade adapter consistent with the principles of the present disclosure.

Saw blade 2104 may be configured to be linked to the distal joint rotation axis of EEA 2102 by blade adaptor 2114. Blade adaptor 2114 may be configured to tighten saw blade 2104. By adapting the blade adaptor 2114, different sagittal saws can be integrated into system 2100. Exemplary configurations for blade adaptor 2114 consistent with the present disclosure are discussed below. An exemplary blade adaptor is illustrated in FIG. 31.

Permanent Fixation

In a permanent fixation configuration, blade 2104 may be permanently clamped to blade adaptor 2114. A user (e.g., a scrub nurse) can assemble blade 2104 to blade adaptor 2114 while a surgeon is preparing a surgical field. Exemplary permanent fixation configurations may include the following.

- Blade 2104 may be firmly clamped to blade adaptor 2114 using a component such as screws or spring loaded latches configured to provide a clamping force against blade 2104.
- Blade 2104 may include an interface, such as through holes, that are configured to fix blade 2104 to blade adapter 2114.
- Blade 2104 and blade adapter 2114 may be manufactured as a single reusable device that is then provided on EEA 2102. Example implementation involves a metal blade attached to a PEEK or Stainless steel blade adapter. Assembly of the blade to the blade adapter is performed by the scrub nurse.
- Blade 2104 and blade adapter may also be manufactured as a disposable (single use) device delivered sterile. Example implementation involves a metal blade which is overmolded using plastic injection molding technology.

Figure 22:
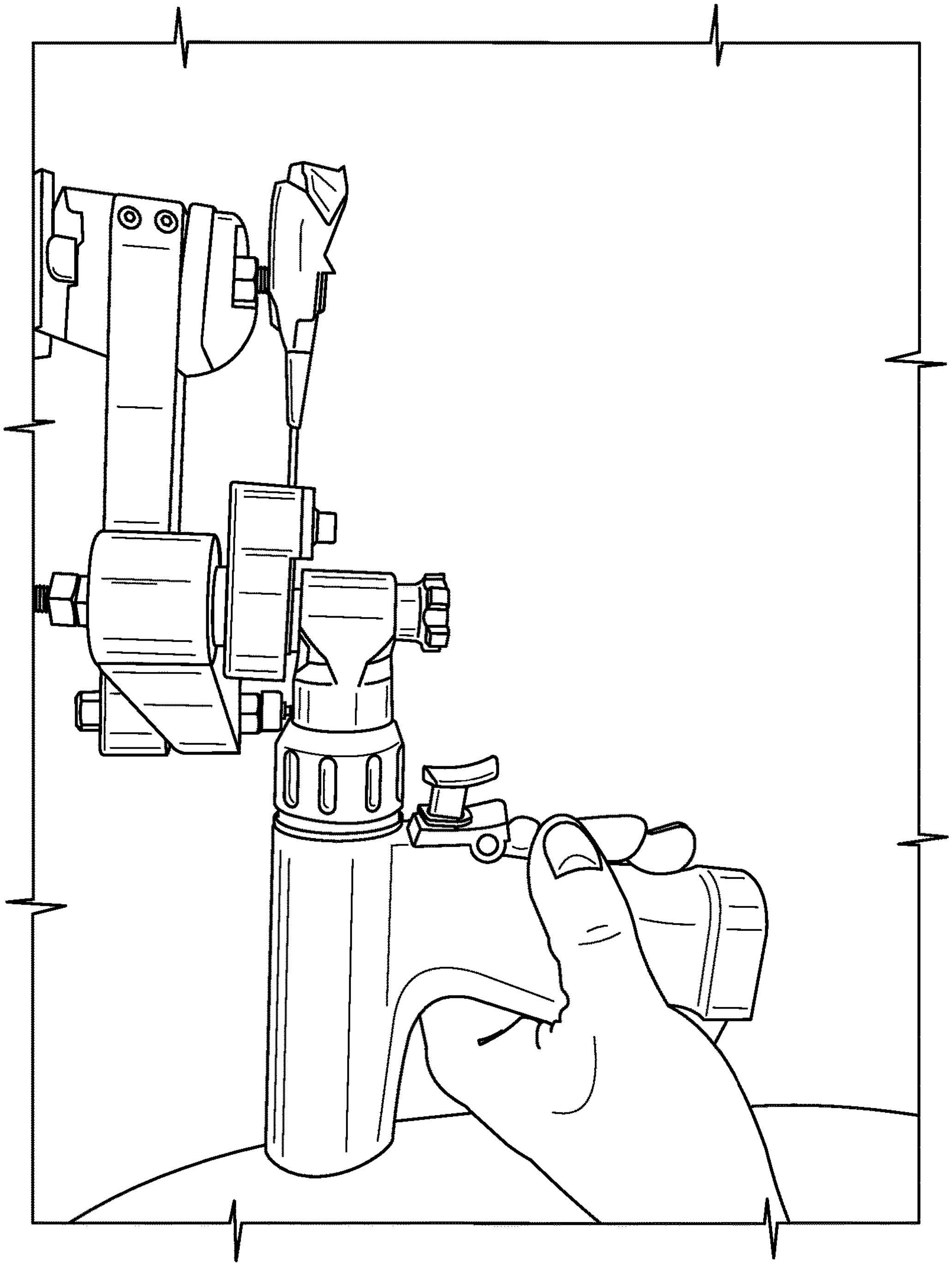
FIG. 22 illustrates an exemplary of a direct blade guidance system consistent with the principles of the present disclosure.
Figure 23:
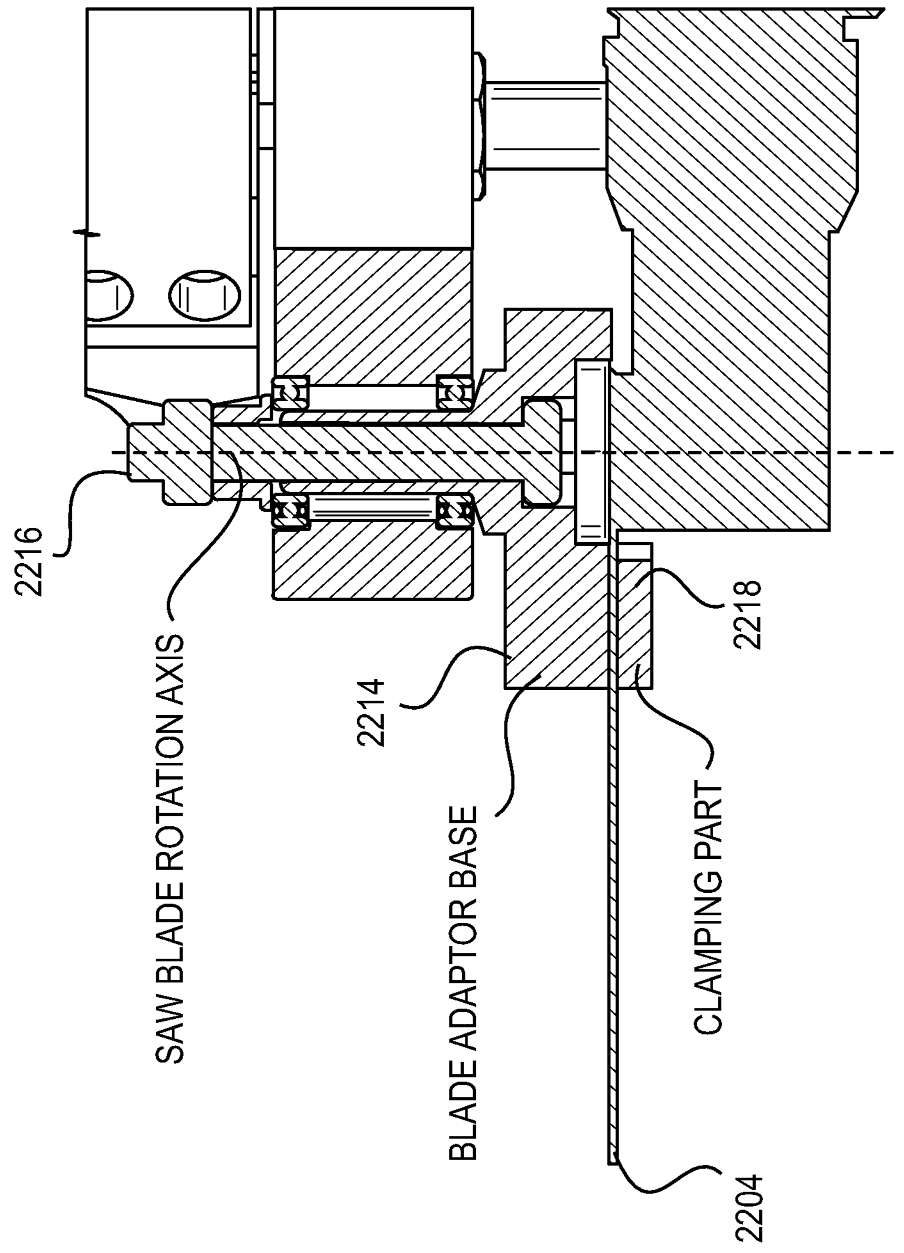
FIGS. 23-24 illustrate an exemplary embodiment of a portion of a direct blade guidance system consistent with the principles of the present disclosure.

FIG. 22 illustrates system 2200, which is an exemplary embodiment consistent with the principles of the present disclosure. In this embodiment, the blade adaptor is permanently affixed to the saw blade in a base that can rotate around the saw blade rotation axis and a clamping component that clamps the blade to the blade adaptor base by means of screws. FIG. 23 illustrates a blade 2204, a blade adaptor 2214, a distal rotational joint 2216, and a clamp 2218 consistent with this configuration. These components can be the same or similar to components previously described with regard to FIG. 21.

Detachable Fixation

In a detachable fixation configuration, the blade can be quickly attached to and detached from the blade adapter in the field. The blade adaptor integrates a clamping mechanism that might be either active (normally closed clamping mechanism that is open by electrical signal) or passive (quick-coupling and/or quick-release mechanism).

Moment of Inertia

Blade adapter 2114 may significantly increase the moment of inertia of the coupled "blade/blade adapter" rotating around blade rotation axis. As soon as blade adapter 2114 vibrates together with saw blade 2104, the unbalanced inertia generates dynamic forces and torques that are exported to the mechanical structure as well as a surgeon's hand. To optimize the implementation, the inertia of the vibrating elements around the vibration axis may be minimized. That means the lighter and closer the mass of the vibrating elements to the vibration axis, the better. The moment of inertia of the saw blade elements about the vibration axis for the handpiece guidance concept is:

$$I_h = I_d + MD^2$$

With D the distance between the blade vibration axis and the distal joint rotation axis, M the weight of the blade (weight of the saw blade elements) and $I_d$ the moment of inertia of the saw blade elements about the blade vibration axis. The moment of inertia is then reduced by $MD^2$ with the direct blade guidance concept, which is the minimum as the distance between the vibration axis and the blade vibration axis is 0 (the axes are combined).

Figure 24:
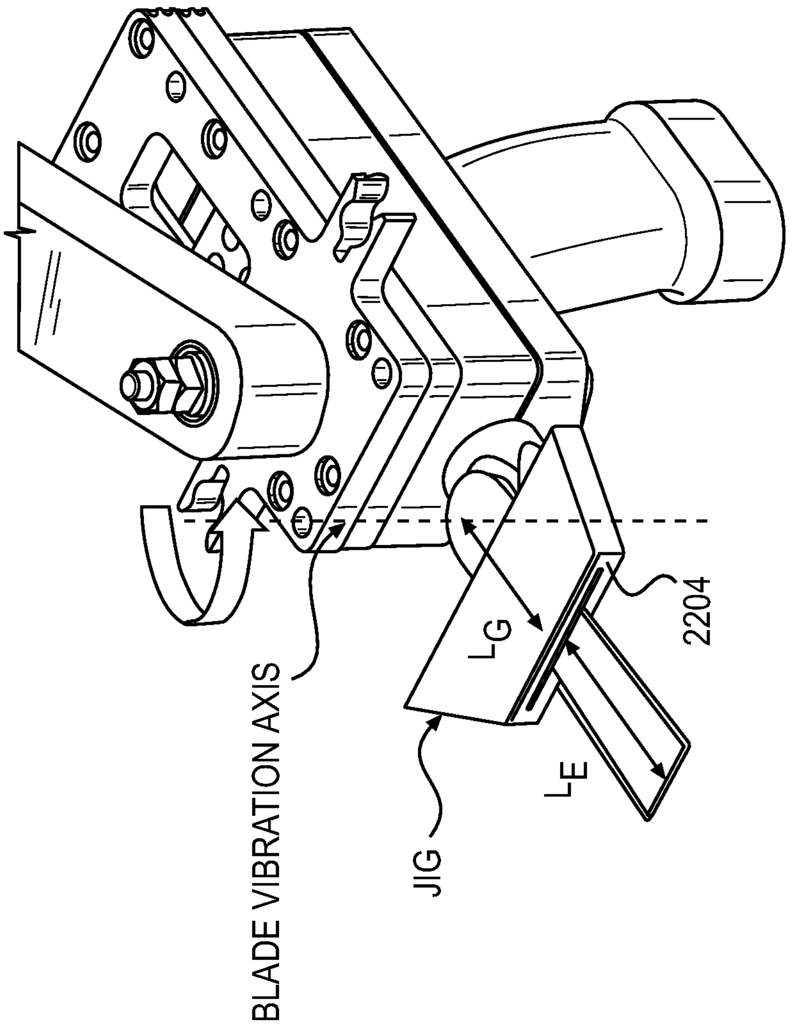

FIG. 24 illustrates a system using a standard jig 2402. Under the principles discussed herein, direct blade guidance may provide more blade effective cutting length than those provided by standard jigs, such as jig 2402 illustrated in FIG. 24. $L_G$ represents the guiding length (length on which the saw blade is guided) and $L_E$ represents the blade effective length. As the guiding length can be made shorter with the direct blade guidance concept, the blade effective length is consequently longer. This is may be more comfortable for a surgeon and the surgeon may cut through more bone.

The precision of the cut is given by the rigidity of the different elements composing the robotic system from the floor to the tip of the saw blade, including the robot system, EEA 2102, a handpiece sagittal saw, a saw blade oscillation mechanism (such as blade adaptor 2114 or 2214), and saw blade 2104, 2204. With the direct blade guidance, the backlash and imprecisions of the handpiece may be significantly minimized or prevented altogether because the saw blade is directly tightened with the blade adaptor.

Moreover, the direct blade guidance concept may be easier to integrate with various existing sagittal saws. There may be no need to build a component which is specific to the shape of the sagittal saw (manufacturer specific) because the blade adaptor is an element which only needs to tighten the saw blade whose shape may be simple. In addition, the blade adaptor is easy to sterilize. It is a small, light and relatively simple mechanical element which can be made in such a way that it does not have any narrow spaces and can be easily disassembled. As previously mentioned, blade including blade adaptor might be delivered as single reusable device.

Tracking

Figure 25:
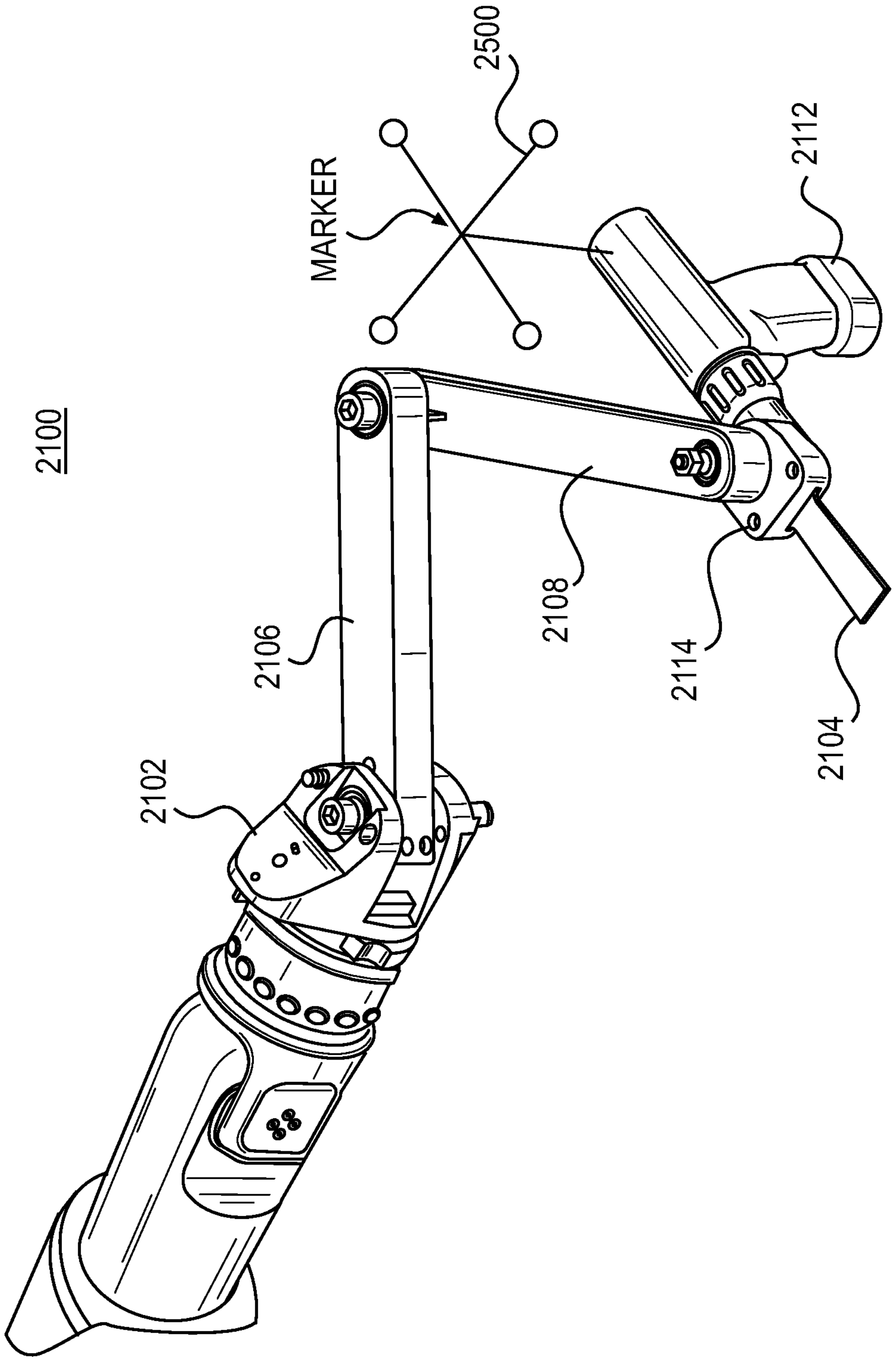
FIG. 25 illustrates an exemplary embodiment of a direct blade guidance system consistent with the principles of the present disclosure.

FIG. 25 illustrates a direct blade guidance system 2100 that may include a navigation marker or array of markers 2500 attached to handpiece 2112 of a sagittal saw. Marker 2500 allows the sagittal saw to be tracked by the camera, such as camera tracking system 6. Optical tracking enables measurement of the saw position but may it may be difficult to measure a direct saw blade position during cutting (high frequency of blade vibration). Moreover, the tracking would directly measure the deflection of the saw handpiece 2112 with respect blade 2104, due to the poor stiffness of the blade/saw handpiece connection.

Figure 26:
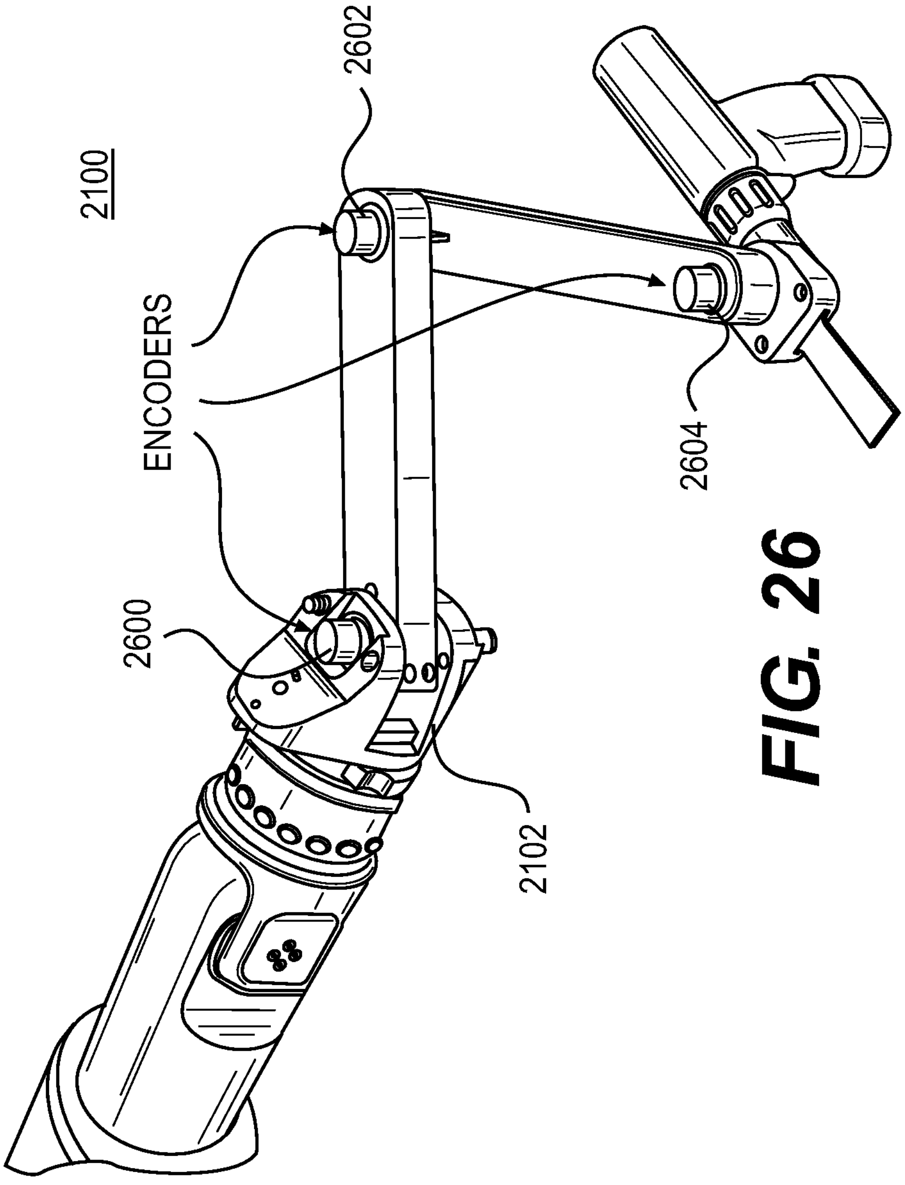
FIG. 26 illustrates an exemplary embodiment of a direct blade guidance system consistent with the principles of the present disclosure.

To measure a direct saw blade position, FIG. 26 illustrates system 2100 with encoders 2600, 2602, and 2604 integrated to the joints of EEA 2102. Encoder measurement can be usually made at higher frequency and rotational precision than using optical tracking. For example, the measurement frequency can be at least two times higher than saw blade oscillation. With a blade position signal, additional useful information may be extracted, such as saw vibration frequency, on/off state, saw blade blocking in bone (for example by interpreting the signal and its derivatives) and others.

In exemplary embodiments consistent with the principles of this disclosure, vibrations of the sagittal saw handpiece held by the surgeon may be reduced. By decreasing vibrations of the handpiece, tactile feedback could be improved and cutting efficiency could be increased. As previously described, the vibrations exported to surgeon's hand result from the exported dynamic forces and torques generated by the unbalanced inertia of couple blade/blade adaptor around blade rotation axis.

Figure 27:
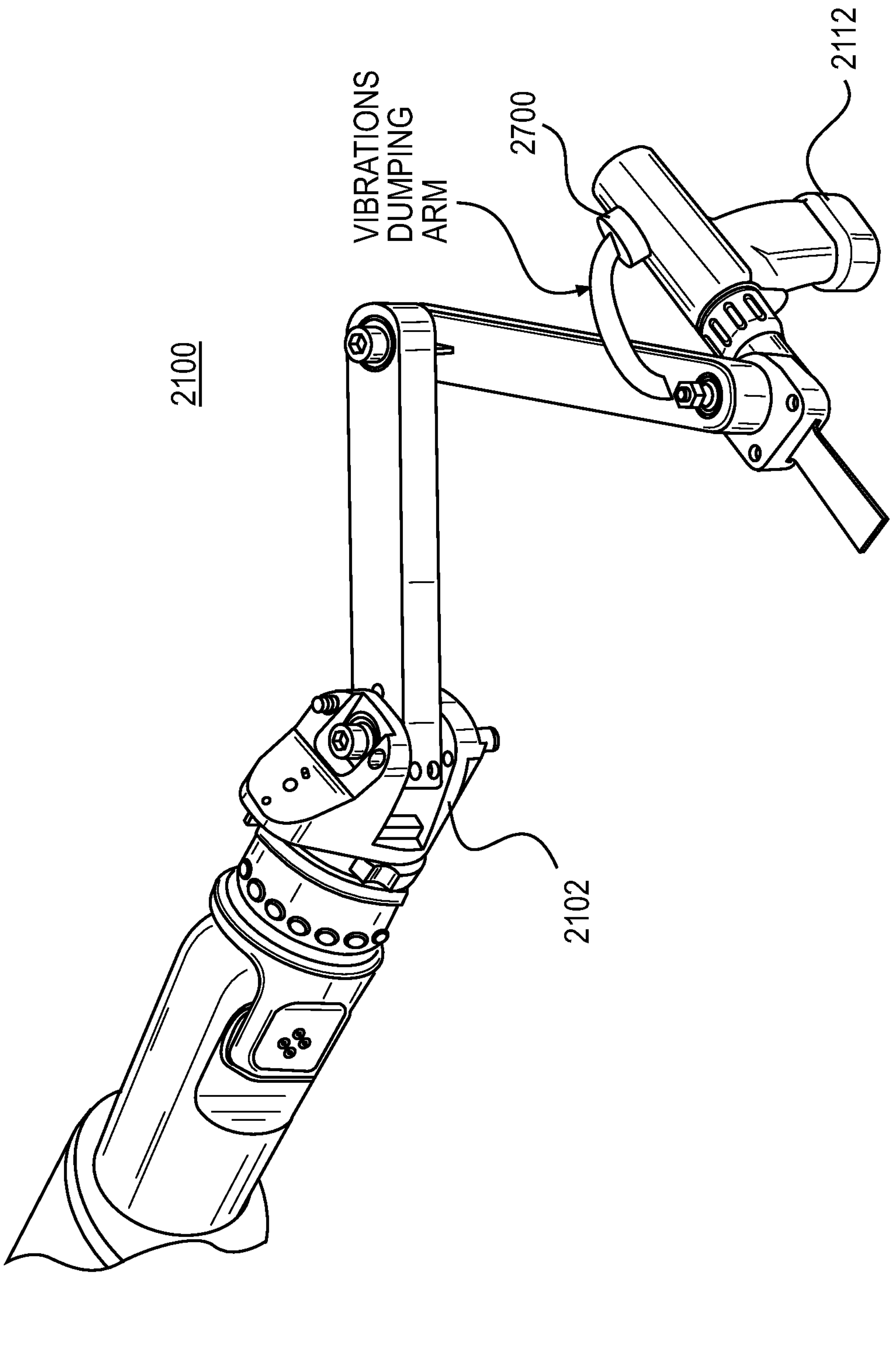
FIG. 27 illustrates an exemplary embodiment of a direct blade guidance system consistent with the principles of the present disclosure.

One approach to reduce the vibrations may be achieved by filtering the vibrations. In FIG. 27, a damping element 2700 may be connected between handpiece 2112 and the EEA 2102. This might be implemented using pieces of rubber, pneumatic or hydraulic cylinder.

Figure 28:
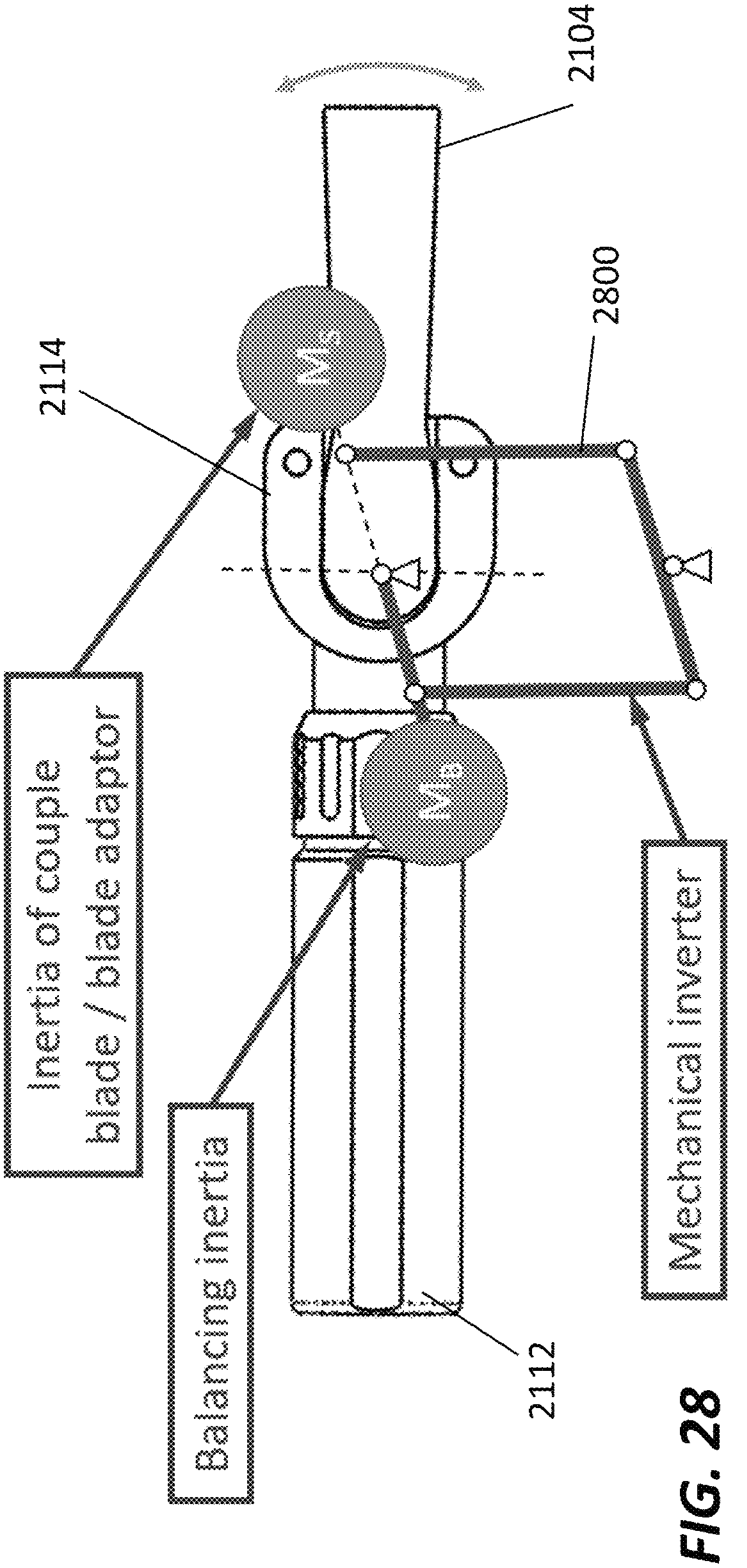
FIG. 28 illustrates an exemplary embodiment of a portion of a direct blade guidance system consistent with the principles of the present disclosure.
Figure 29:
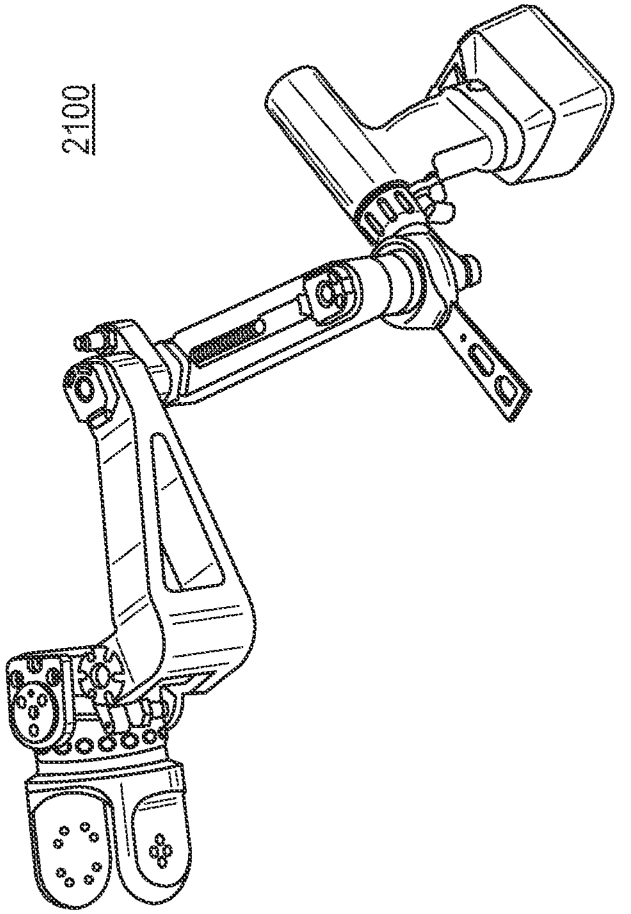
FIGS. 29-30 illustrate an exemplary embodiment of a direct blade guidance system consistent with the principles of the present disclosure.
Figure 30:
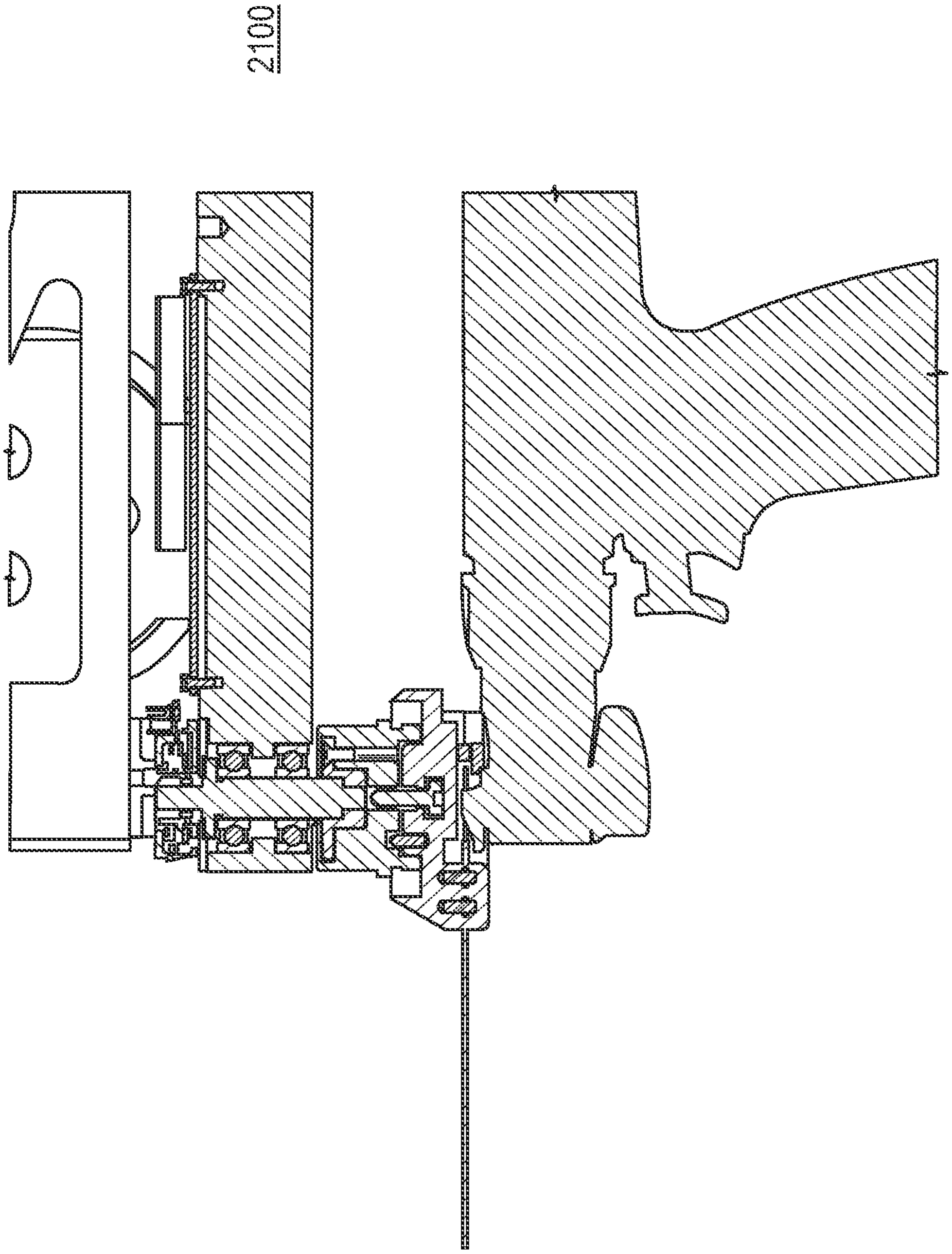
Figure 32:
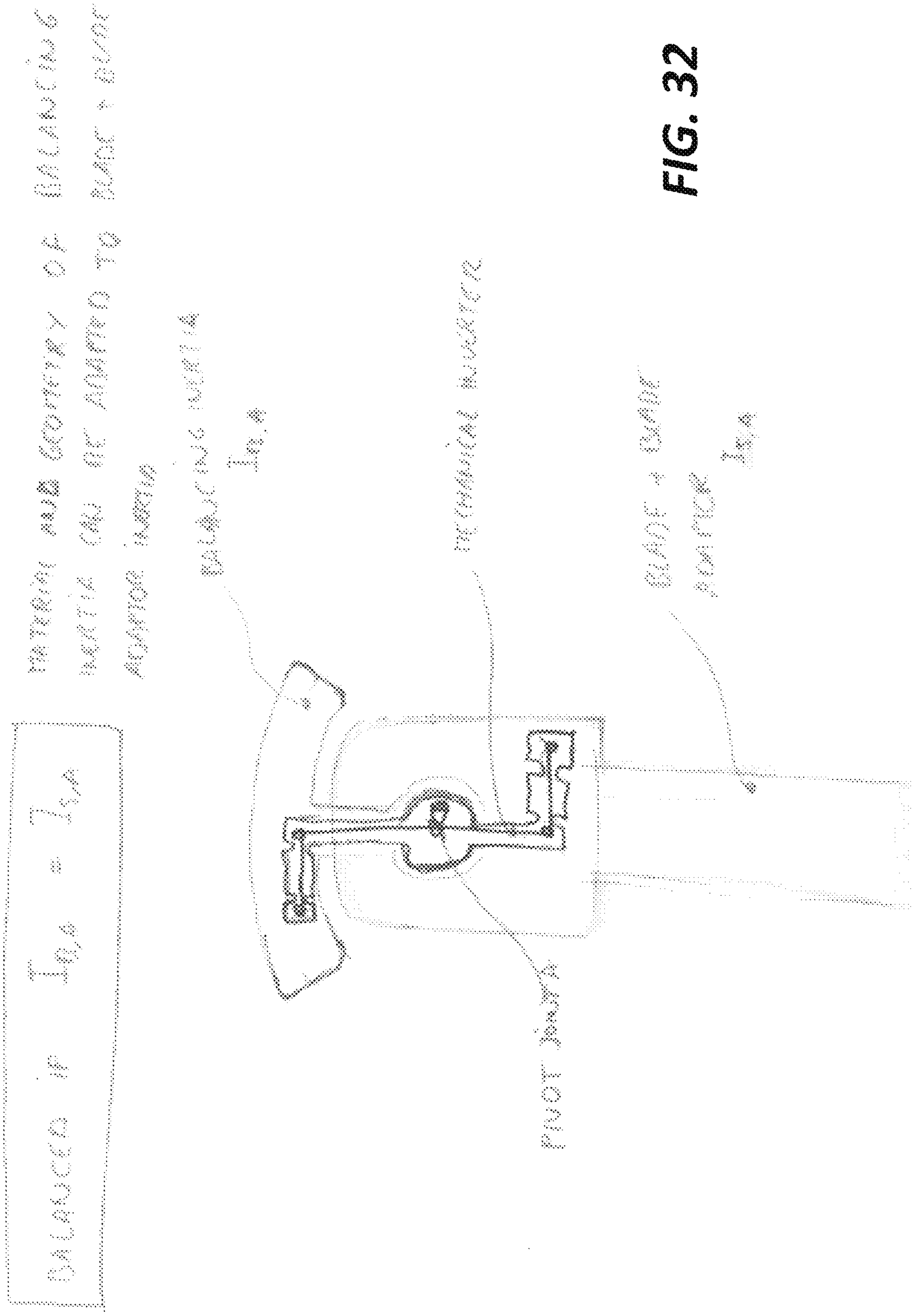
FIG. 32 illustrates an exemplary embodiment of a direct blade guidance system consistent with the principles of the present disclosure.

Another approach to reduce the vibrations may be achieved by dynamically balancing the inertia of the coupled saw/saw adaptor around the saw rotation axis. This can be implemented by dynamically compensating the exported forces and torques generated by the vibrating saw blade using a compensation inertia that performs the exact opposite movement with the same dynamics. FIGS. 28 and 32 illustrates exemplary embodiments where compensation inertia can be coupled to the main inertia to be balanced using a mechanical inverter 2800.

Referring now to FIGS. 33-45, consistent with the principles of the present disclosure, a navigated pin guide driver with a handle and an attached reference element may be used to obviate the need for using a placement instrument and navigating a placement instrument. For example, a surgeon may hold the handle and the navigation system may track the reference element. The navigation system provides real-time feedback on the placement of the pins and a visual representation of the cuts, or a visual representation of the cut block with respect to the patient anatomy. The surgeon may use the navigated pin handle free hand or in conjunction with the passive end effector as previously described herein.

Figure 33:
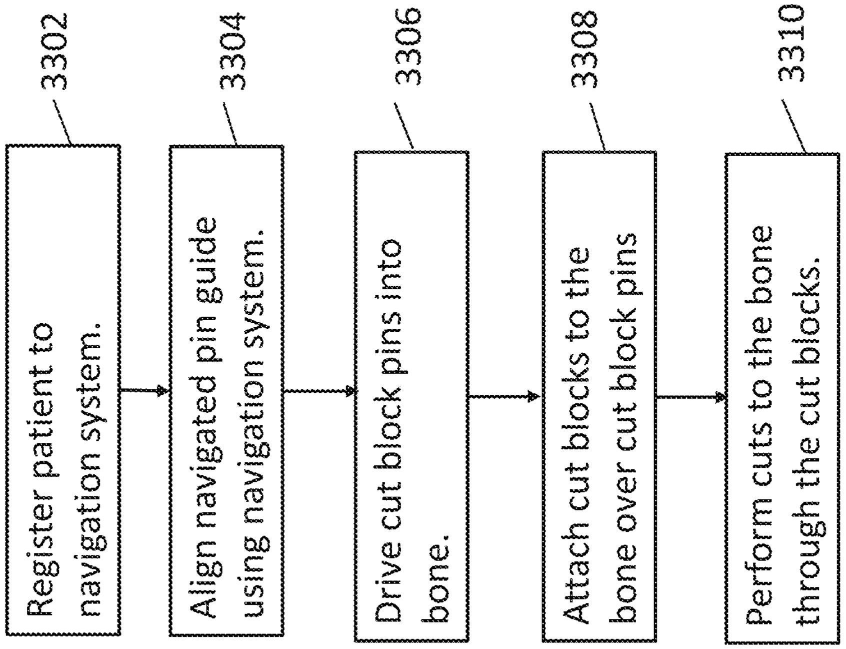
FIG. 33 illustrates a flowchart for a method of performing a knee surgery consistent with the principles of the present disclosure.

A proposed workflow consistent with the principles of the present embodiment is illustrated in FIG. 33 as method 3300. At step 3302, a patient may be registered to the navigation system. At step 3304, a navigated pin guide driver system is aligned to a targeted area of a bone using navigation system feedback. At step 3306, cut block pins are driven into bone. At step 3308, cut blocks are attached to the bone over the cut block pins and at step 3310 cuts are performed through the cut blocks.

Figure 34:
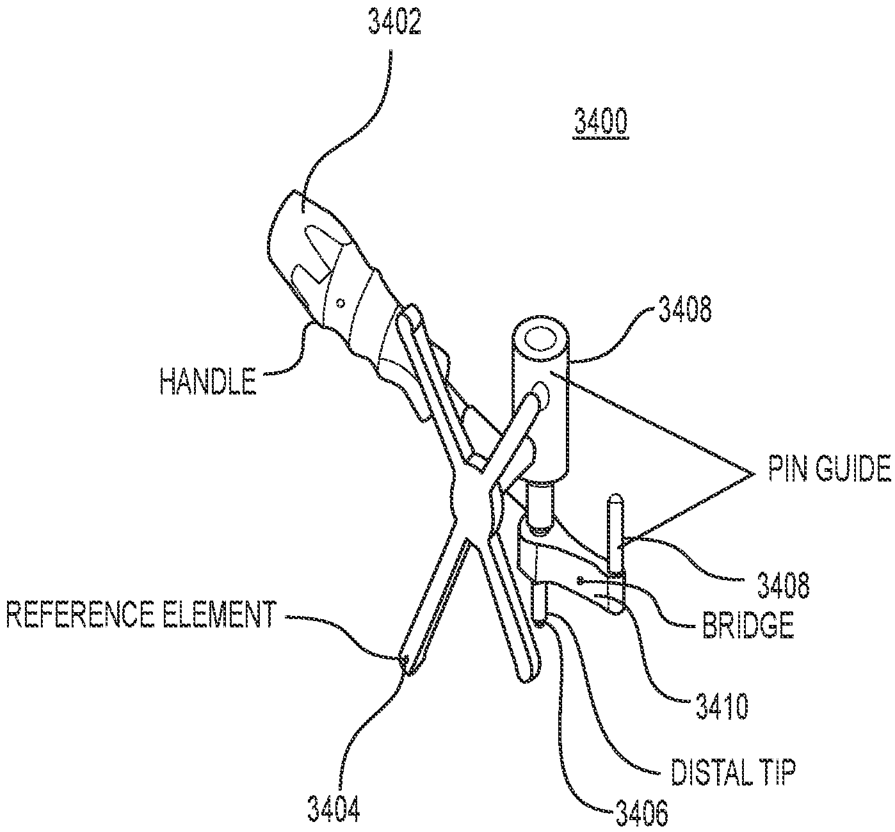
FIGS. 34-37 illustrate a navigated pin guide driver system consistent with the principles of the present disclosure.
Figure 35:
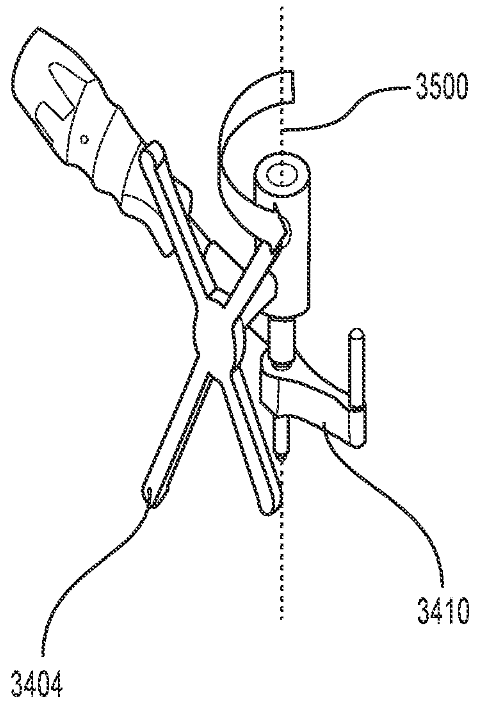

Referring to FIG. 34, an exemplary schematic of a navigated pin driver system 3400 is illustrated. Navigated pin guide driver system 3400 may include a handle 3402 for the user to hold, a reference element 3404, a distal tip 3406 for docking onto cortical bone, and 2 parallel pin guides (or guide tubes) 3408 separated by a bridge 3410. Bridge 3410 maintains spacing to ensure that pin spacing matches that of the corresponding cut block. While FIG. 34 is illustrated with a single instrument that has two parallel pin guides 3408, system 3400 may be constructed with only one pin guide 3408. In order to optimize the viewing angle and ergonomics for a user, bridge 3410 and reference element 3404 can be rotated about an axis 3500 as shown in FIG. 35. Reference element may include markers configured to be tracked by a navigation system, for example, optical markers detectable by an infrared camera.

Figure 36:
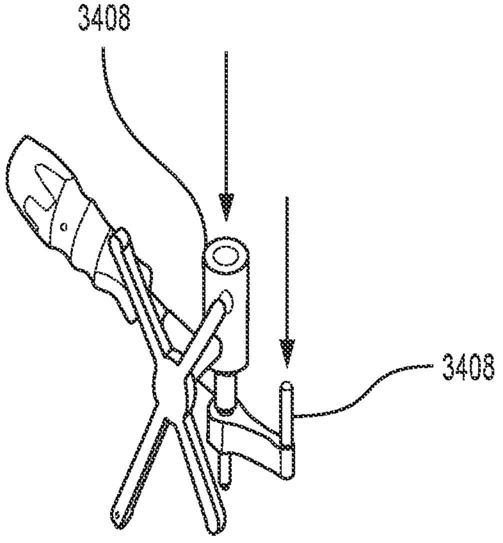

When using system 3400, a user may register the patient to a navigation system and make an initial incision to expose the knee joint. Once exposed the user can position the navigated pin driver system as indicated by the navigation system. The user may then insert cut block pins, which can be conventional style pins, through pin guide tubes 3408 as shown in FIG. 36.

Figure 37:
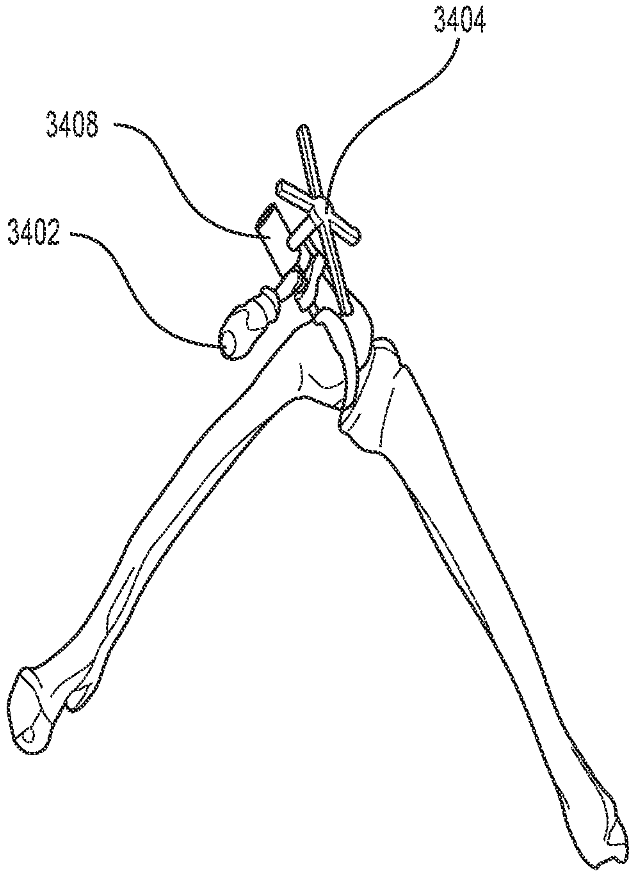
Figure 38:
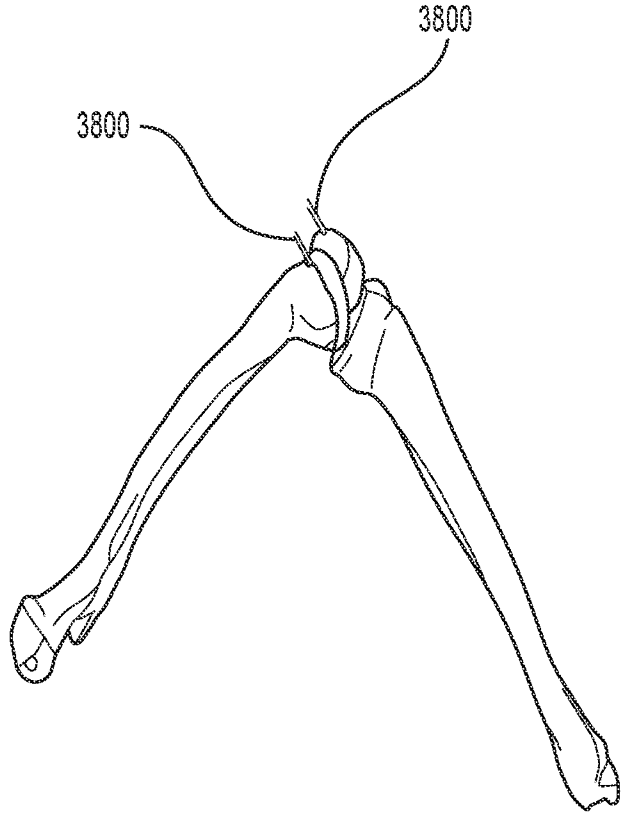
FIG. 38 illustrates cut block pin inserted using a navigated pin guide driver system consistent with the principles of the present disclosure.

An example of how the navigated pin guide driver system 3400 can be used clinically is as follows: (1) plan the implant placement; (2) register the patient to the navigation system; (3) expose the knee; and (4) use the navigated pin driver system 3500 to insert pins 3800 for the distal femur cut block as shown in FIGS. 37-38.

Figure 39:
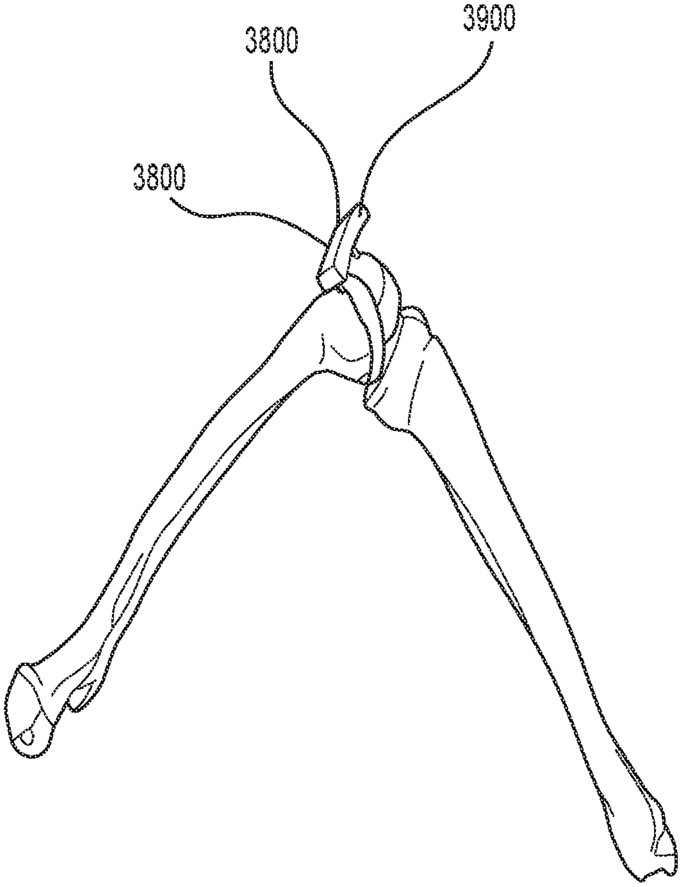
FIGS. 39-40 illustrates a cut block inserted using a navigated pin guide driver system consistent with the principles of the present disclosure.
Figure 40:
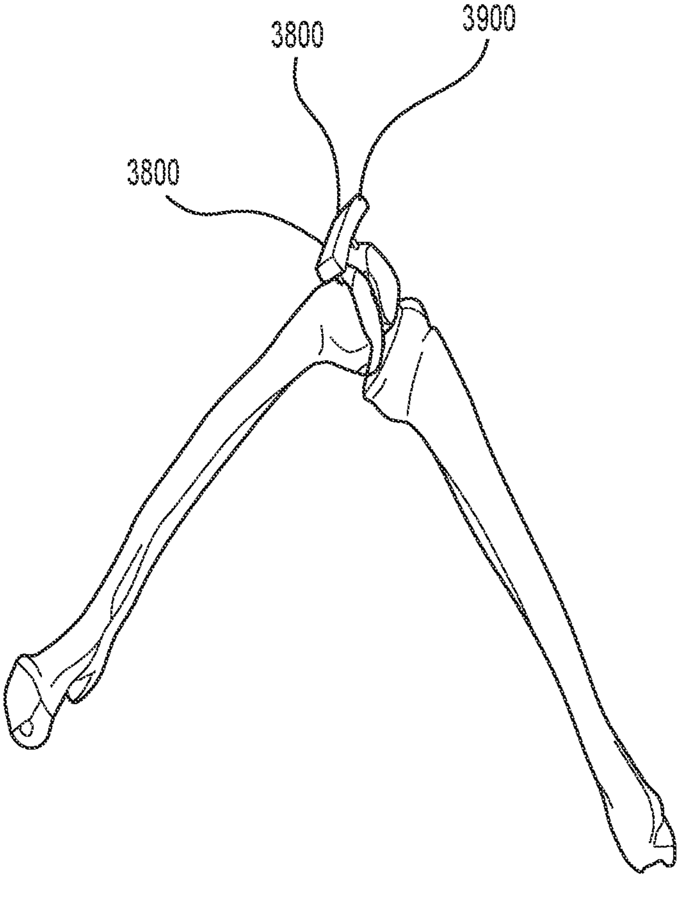
Figure 41:
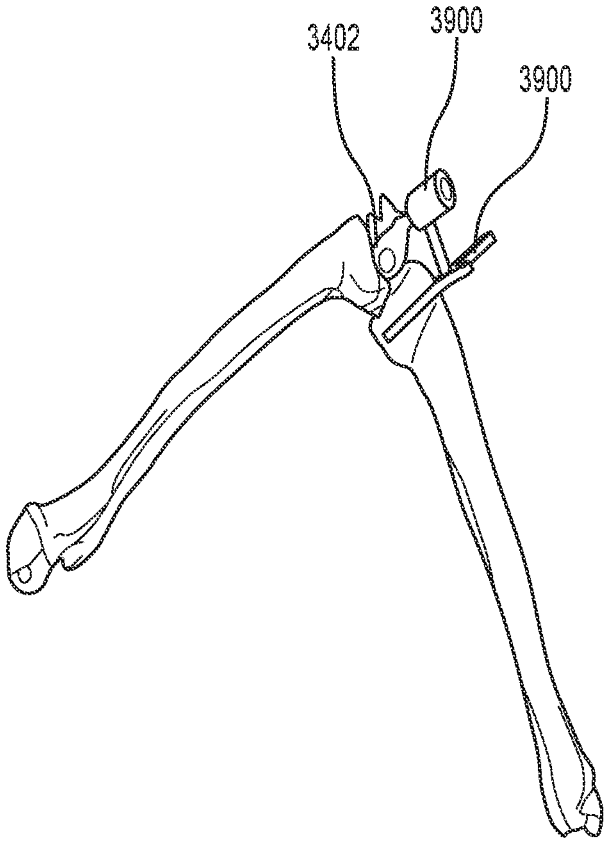
FIG. 41 illustrates a navigated pin guide driver system consistent with the principles of the present disclosure.
Figure 42:
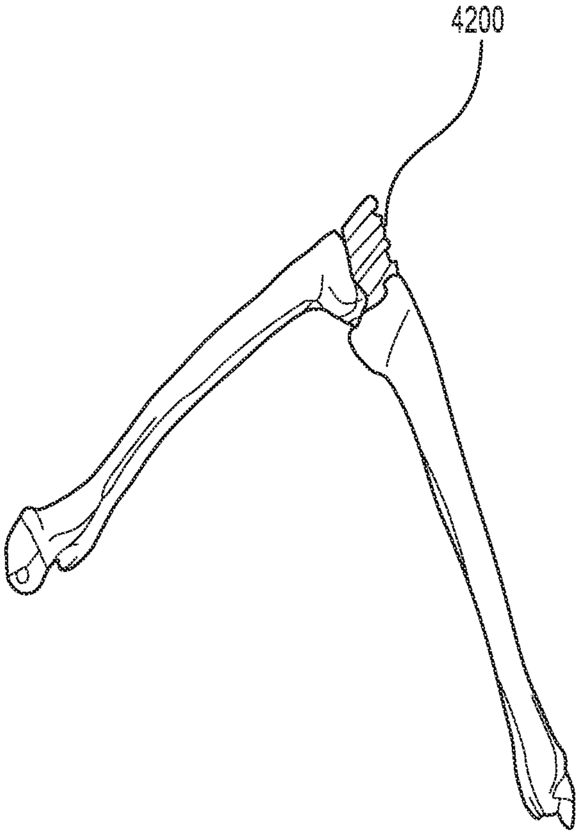
FIG. 42 illustrates a cut block inserted using a navigated pin guide driver system consistent with the principles of the present disclosure.
Figure 43:
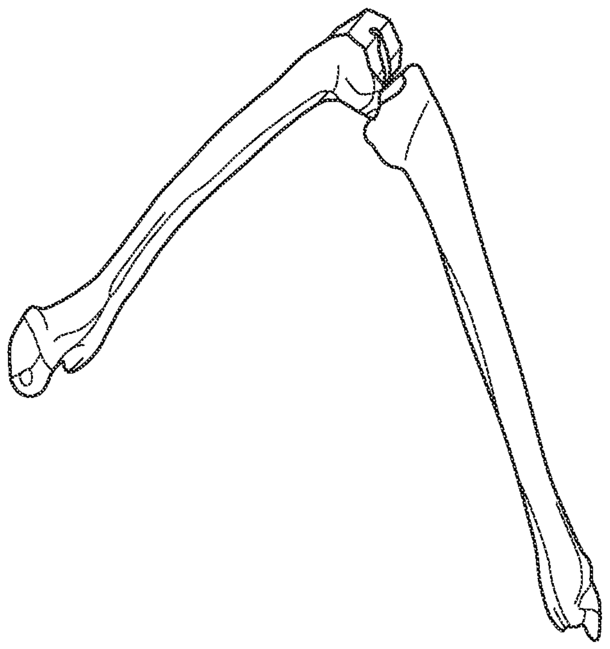
FIG. 43 illustrates a resected knee joint using a navigated pin guide driver system consistent with the principles of the present disclosure.
Figure 44:
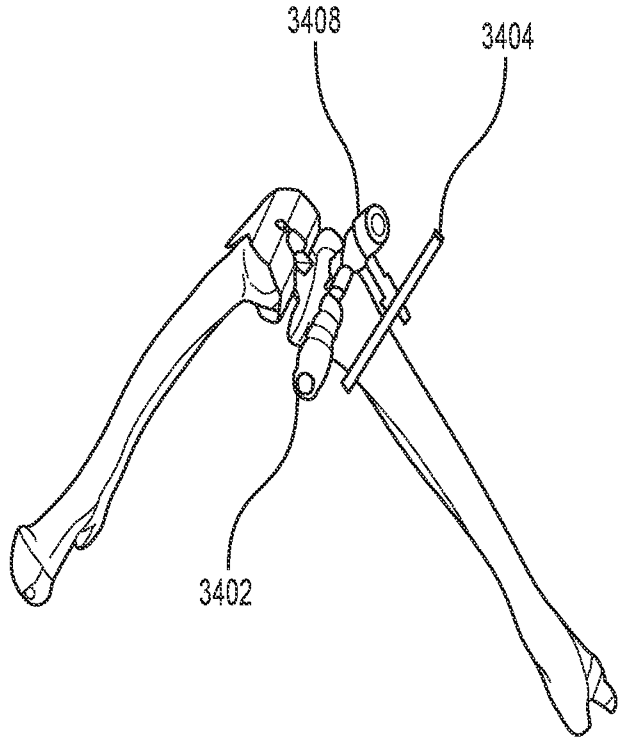
FIG. 44 illustrates a navigated pin guide driver system consistent with the principles of the present disclosure.
Figure 45:
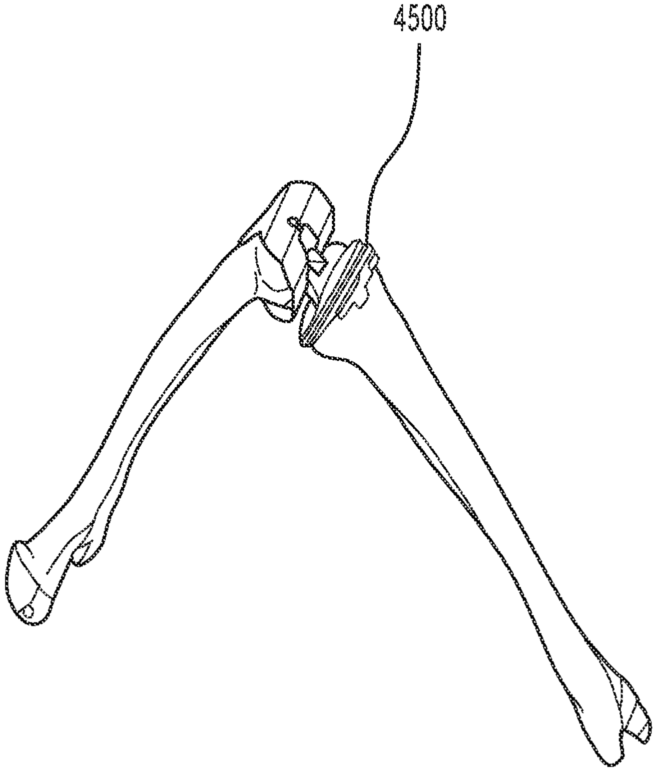
FIG. 45 illustrates a cut block inserted using a navigated pin guide driver system consistent with the principles of the present disclosure.

After steps (1)-(4) noted above, at step (5) a distal cutting block 3900 may be attached over pins 3800 as shown in FIG. 39. As shown in FIG. 40, at step (6) a distal resection may be performed. Shown in FIG. 41, at step (7), using system 3400, pins are inserted or holes created for localizing a 4 in 1 cut block 4200 which is attached to the resected section at step (8) and shown in FIG. 42.

After the 4 in 1 cut block 42 is attached, at step (9), anterior femoral, femoral chamfer, posterior femoral, posterior chamfer resections are made using 4 in 1 cut block 4200. At step (10), using navigated pin guide driver system 3400, pins are placed for proximal tibial cut block 4500. At step (11), proximal tibial cut block 4500 is put in place and a resection is performed. At step (12), the total knee arthroplasty may be completed by inserting the appropriate implants. Alternatively and without departing from the principles of this disclosure, resection may be performed on the tibia prior to resection of the femur.

Consistent with the principles of the present disclosure, navigated pin driver system 3500 may include a conforming style gripper instead of a serrated distal tip. The gripper may use granular jamming and be activated by a vacuum already present in the operating room.

In an alternative for the user to directly position the pin guide and to simplify navigated pin guide placement, software may assist the user as explained in the following workflow.

(1) Showing, via software, the target position of one pin guide (e.g. distal tip) on the bone to the user, for example a computer screen, an augmented reality (AR) headset, and a laser pointer.
   (a) Showing only a position or entry point, i.e. correct instrument rotation is not required at this stage.
   (b) Distal tip teeth/sharp edges help user for finding and maintaining correct entry point.
   (c) Once the position of instrument distal tip is within predefined safety limit from the target one (e.g. 1 mm), indicating to the user via software (e.g. showing green color) and moving to the next step.
(2) Showing, via software, a target rotation of the pin guide allowing the user to find a correct trajectory for the first pin.
(3) User places first pin.
(4) Showing, via software, a target rotation around the first pin to define the correct trajectory for the second pin.
(5) User places second pin and retracts guide along the pins.

Figure 46:
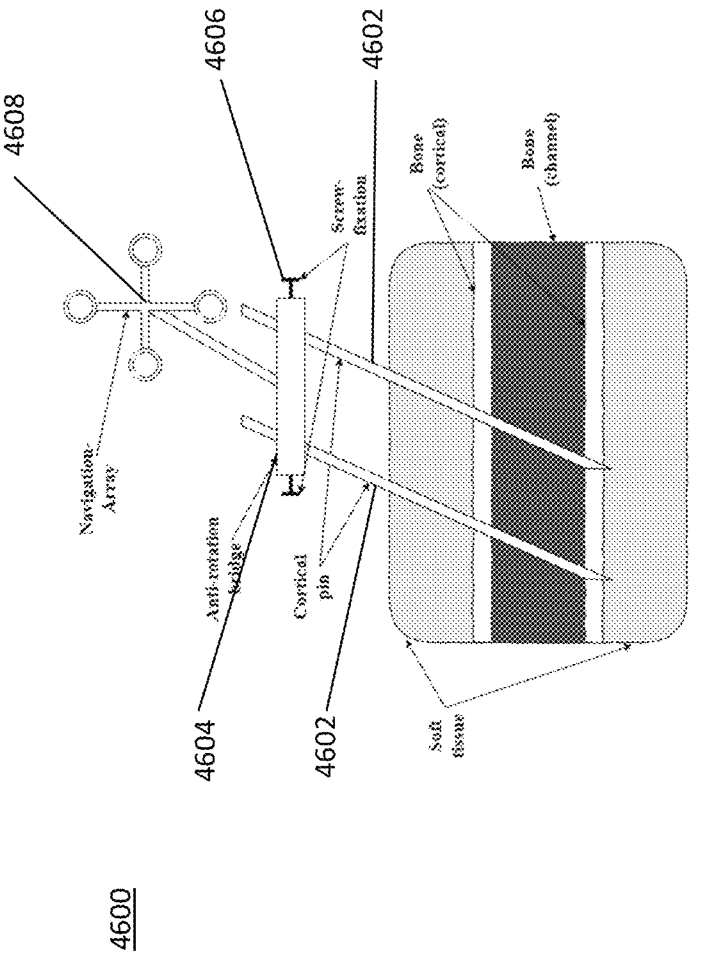
FIG. 46 illustrates a fixation device for a navigation array consistent with the principles of the present disclosure.

Referring now to FIGS. 46-52, exemplary fixation devices and methods relating to optical navigation arrays attached to a bony structure will be described. FIG. 46 illustrates an exemplary fixation device 4600 having dual cortical pins 4602 with a connection bridge 4604. Two standard, round, and auto-piercing cortical pins 4602 are drilled through soft tissue and through both bone cortical and the bone channel. Drilling distance between pins 4602 is indicated by a drilling guide (not shown) and the depth and orientation may be determined by a surgeon based on personal preference. A rigid bridge 4604 is attached to the pins 4602 (e.g., by closing a fixation screw 4606), blocking rotation of and serving as primary connection point to the navigation array 4608. The connection of the array 4608 to the bridge 4604 is adjustable in two orthogonal rotational and one translational DOF. Removal of pins 4602 is done by turning and pulling them from the leg. A suture of the incisions left from piercing the skin is done.

Figure 47:
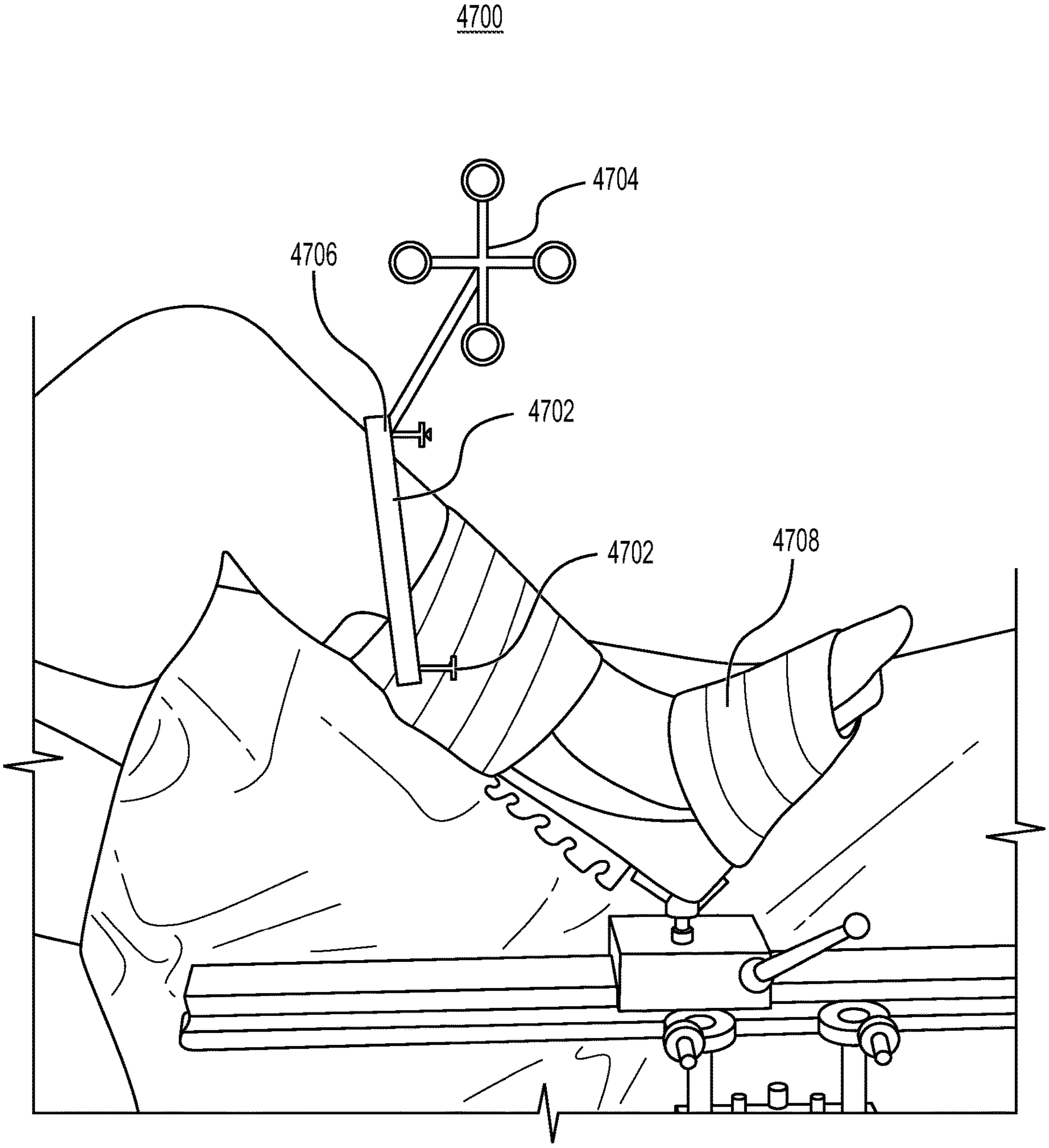
FIG. 47 illustrates a fixation device for a navigation array consistent with the principles of the present disclosure.

FIG. 47 illustrates an exemplary external foot fixation device 4700. Device 4700 is rigidly connected to a foot-orthosis/guidance. The foot and tibia are locked in the orthosis by attaching both malleoli with an adjustable screw 4702 pushing against both anatomical landmarks and closing the kinematic chain. This guarantees a coupling of both tibia and foot rotation. A navigation array 4704 is connected to a rod 4706 adjustable in length and angle (in both axis orthogonal to the rod's center axis) and the foot orthosis 4708. For a navigation array to track the femur, other fixation devices described herein may be used. For removal of the array, no surgical intervention is needed. Soft tissue and bone are kept unharmed.

Figure 48:
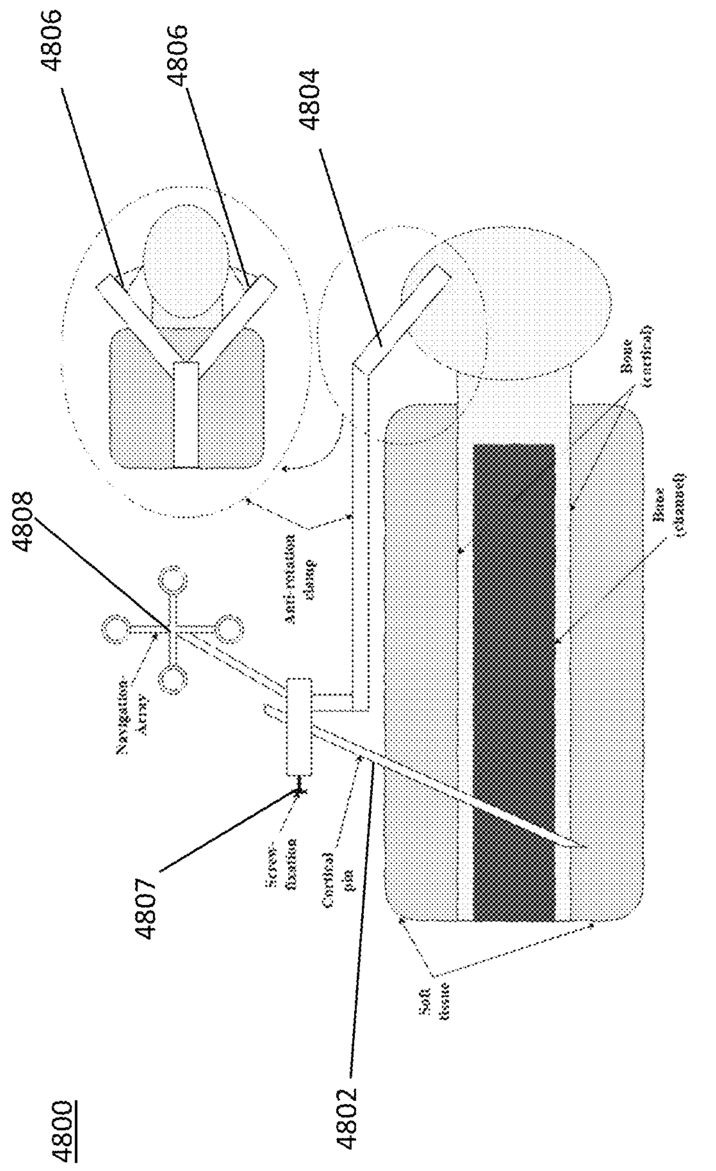
FIG. 48 illustrates a fixation device for a navigation array consistent with the principles of the present disclosure.

FIG. 48 illustrates an exemplary fixation device 4800 having a cortical pin 4802 with an anti-rotation clamp 4804. An external rigid anti-rotation clamp 4804 is connected with two spikes 4806 to a bony surface intra-incision. One cortical pin 4802 is inserted through an incision into the bone, using the anti-rotation clamp as jig 4804. Together they form a rigid anchor/connection point to the bone. Clamp 4804 is connected to the cortical pin by an adjustment screw 4807 and form fit, blocking all remaining DOF. The anti-rotation clamp 4804 does not pierce the bone cortical but is clamped rigidly by means of force fit. A navigation array 4808 is connected to a structure, such as described in FIG. 46, with possibilities of adjustment in different planes. Removal is performed by opening the anti-rotation clamp and pulling the cortical pin from the leg.

Figure 49:
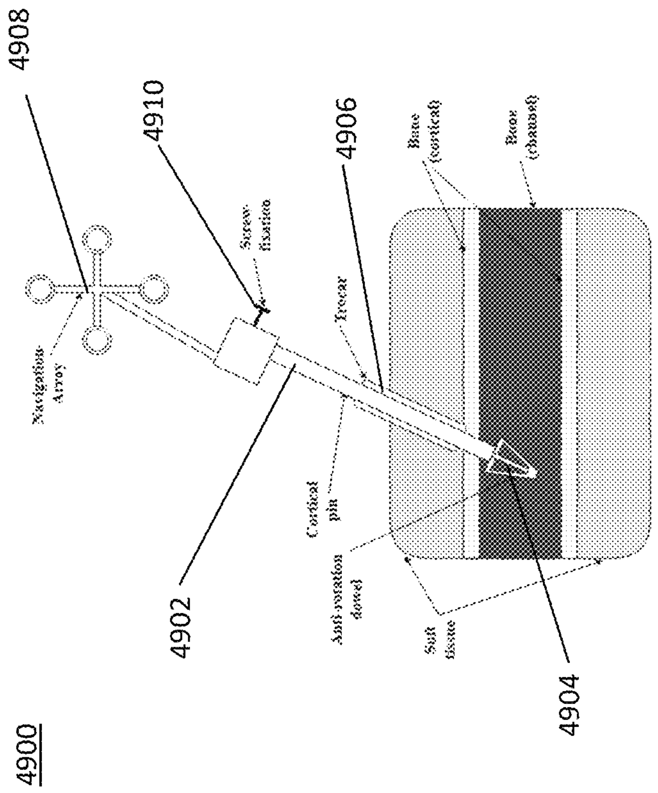
FIG. 49 illustrates a fixation device for a navigation array consistent with the principles of the present disclosure.

FIG. 49 illustrates an exemplary fixation device 4900 having a cortical pin 4902, an anti-rotation dowel 4904, a trocar 4906, a navigation array 4908, and screw 4910. FIGS. 50A-C and 51A-C illustrates exemplary embodiments of anti-rotation dowels that may be used with fixation device 4900. In an exemplary method, a hollow shaft (trocar) 4906 is inserted through an incision in the soft tissue onto the bone. A pin 4902 is inserted through trocar 4906 and penetrates the first bone cortical until a predefined end-stop on pin 4902 indicates the correct depth. The tip of pin 4902 is equipped with a "dry-wall-dowel" anchor-like structure, able to open and close freely in the bone canal. Navigation array 4908 may be attached to cortical pin 4902 via screw 4910.

Examples of the anti-rotation dowels are illustrated in FIGS. 50A-51C. An example includes an anchor device 5002 shown in FIG. 50A. Device 5002 includes at least two wings 5004 that pivot around one common axis at the tip of pin 4902 and that can translate orthogonal to the pin's center/longitudinal axis (e.g., by employing a linear guided fixation). Device 5002 may be opened/closed by lengthening/shortening a center screw/center pin changing distance of pivot to the fixation.

Figure 50A:
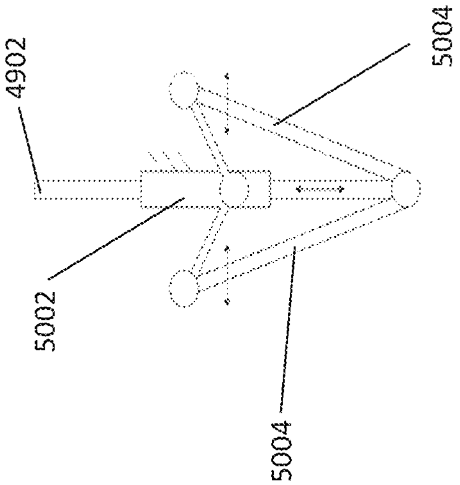
FIGS. 50A-51C illustrate exemplary anti-rotation dowels consistent with the principles of the present disclosure.
Figure 50B:
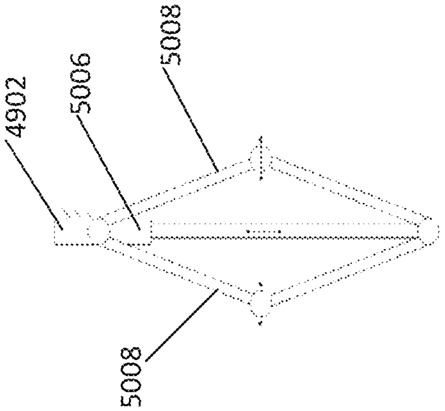

Another example is a morning star device 5006 shown in FIG. 50B. Morningstar device 5006 may have at least two wings 5008 connected that are able to pivot in their respective center when a distance between the endpoints (fixed to a center screw or rod and pin 4902) is shortened. Morningstar device 5006 may be opened/closed by lengthening/shortening a center screw/center pin changing distance of pivot to the fixation.

Figure 50C:
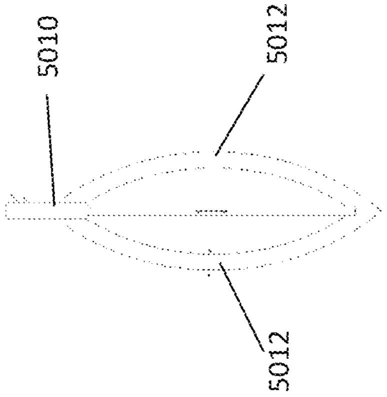

A further example is a morning star device 5010 shown in FIG. 50C. Morningstar device 5010 may have at least two wings 5012 that bend into a round shape by shortening the distance between the endpoints (fixed to a center screw or rod and pin 4902). Device 5010 may be opened/closed by lengthening/shortening a center screw/center pin changing distance of pivot to the fixation.

Figure 51C:
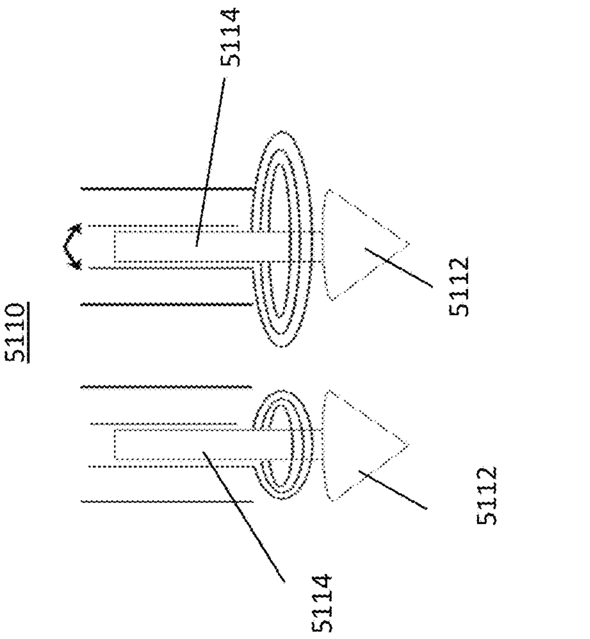
Figure 51B:
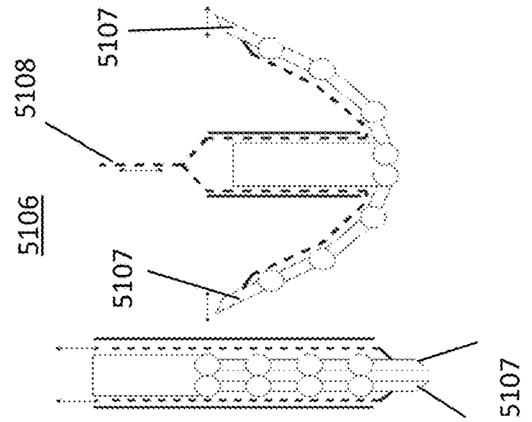
Figure 51A:
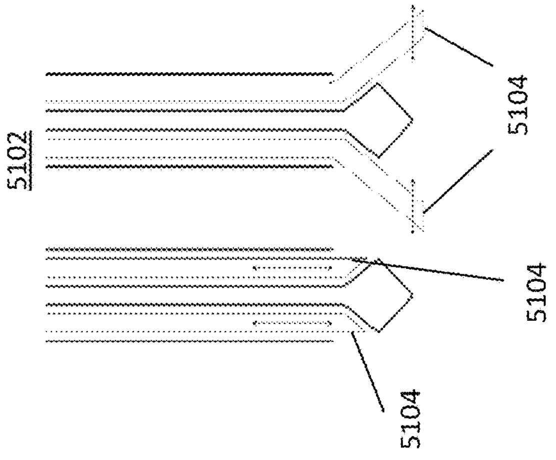

FIG. 51A illustrates an exemplary inverse gripper device 5102. Device 5102 may have at least two wires 5104 (e.g. nitinol) and one center piece form pin 4902. The center piece ends in a shape constraining wires 5104 to be pushed away from the center (longitudinal) axis and thus forming an anchor. Device 5102 may be opened/closed by lengthening/shortening the free wire length FIG. 51B illustrates a device 5106 that may shaped like Origami/Octopus-fingers. Device 5106 may have at least two origami structures 5107 (series of flexible hinge joints) form pin 4902. A wire/cable 5108 is routed through the structure and enables opening. The end of the origami structure is made of a "cutting" surface. In deployed configuration, a double hook like structure is formed. This device may be opened/closed by pulling/releasing cable 5108.

FIG. 51C illustrates an unwinding spring device 5110. Device 5110 may include at least one torsion-spring like structure 5112 that is connected to the end of pin 4902 on one side, and to an inner pin/screw 5114 on the other side, increasing the surface and locking the array by unwinding. This device may be opened/closed by turning the inner pin/screw clockwise/anti-clockwise By opening any of the dowels described, all possible translations and rotations are locked. A rigid connector as an attachment point for the navigation array is attached to pin 4902 (e.g., by closing a fixation screw and form fit). The connection of the array to the connector is adjustable in two orthogonal rotational and one translational DOF. Removal of pin 4902 is done by reversion of the installation steps.

Figure 52:
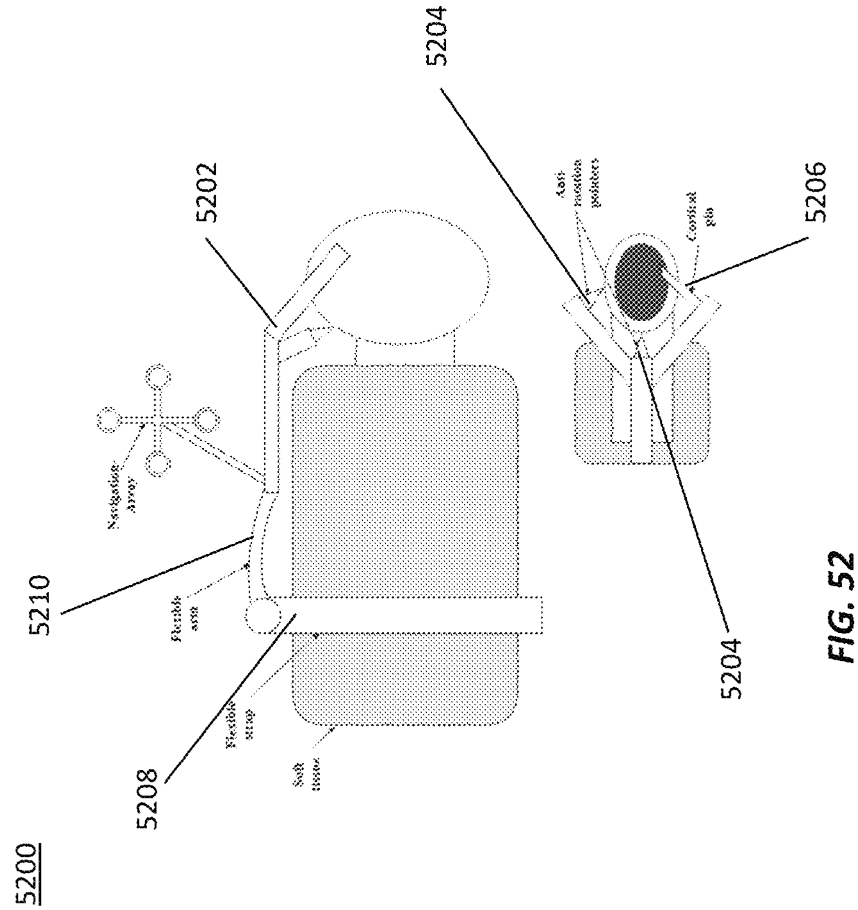
FIG. 52 illustrates a fixation device for a navigation array consistent with the principles of the present disclosure.

FIG. 52 illustrates an exemplary tripod fixation device 5200. An external rigid anti-rotation clamp 5202 is connected with 2 spikes 5204 to a bony surface intra-incision. One cortical pin 5206 is placed intra-incision to prevent rotation. A fixation band 5208 is tightened around the leg to allow for increased stability and is connected via a flexible/elastic 5210 arm to the anti-rotation clamp 5202. The flexible/elastic arm ensures that controlled force is applied to cortical pin 5206 when the leg is moved (during leg movement skin can move up to 2 cm in reference to bone). All DOF are locked. Spikes 5204 do not pierce the bone cortical but are clamped rigidly by means of force fit. The navigation array is connected to the arm 5210 with possibilities of adjustment in different planes (2 rotational and one translational DOF). Removal is performed by opening anti-rotation clamp 5202 and fixation band 5208 as well as pulling cortical pin 5206 from the leg. Suture at the cortical pin position is not needed as it lies intra-incision.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A fixation device for securing a navigation array to a bony structure for use in a robotic-assisted surgery, comprising:

a trocar;

a cortical pin, having a first longitudinal axis, configured to be inserted into the trocar;

a dowel configured to be attached to the cortical pin, wherein the dowel is configured to prevent rotation of the cortical pin in the bony structure, and wherein a distal end of the dowel defines a distal end of the fixation device in an open configuration; and a navigation array configured to be removably attached to the cortical pin, wherein the navigation array has a second longitudinal axis that is offset from the first longitudinal axis, and wherein the dowel includes first and second wing structures forming a pin, each wing structure having a series of flexible hinge joints, the first and second wing structures extending proximally and radially outwardly from each other from the distal end of the dowel and each extended wing structure having a proximal end in which the entire length from the distal end of the dowel to the proximal end of the each extended wing structure is not in contact with the other extended wing structure;

wherein the dowel is opened and closed by pulling or releasing a cable.

2. The fixation device of claim 1, wherein the dowel is configured to be inserted into cortical bone and a bone channel.

3. The fixation device of claim 1, wherein the navigation array includes optical markers visible to an infrared camera system.

4. The fixation device of claim 1, wherein the dowel is configured to be deployed via a wire pushing through the cortical pin.

5. The fixation device of claim 1, wherein the fixation device is configured to be fixated to a bony structure of a patient to perform knee arthroplasty robotic- assisted surgery.

6. The fixation device of claim 1, wherein a distal end of each of the wing structures points in a proximal direction.

7. A fixation device for securing a navigation array to a bony structure for use in a robotic-assisted surgery, comprising:

a trocar;

a navigation array;

a single cortical pin configured to be inserted into the trocar and into a bone structure and adapted to be removably attach to the navigation array;

an anti-rotation device attached to a distal portion of the cortical pin and configured to prevent rotation of the inserted cortical pin in the bony structure, the anti-rotation device having first and second wing structures, each wing structure having a series of hinge joints that are interconnected to each other and deployable into an open position such that the first and second wing structures extend proximally and radially outwardly from each other from a distal end of the anti-rotation device and each extended wing structure having a proximal end in which the entire length from the distal end of the anti-rotation device to the proximal end of the each extended wing structure is not in contact with the other extended wing structure.

* * * * *